(12) United States Patent
Oida et al.

(10) Patent No.: US 6,300,357 B1
(45) Date of Patent: Oct. 9, 2001

(54) TRIAZOLE ANTIFUNGAL AGENT

(75) Inventors: Sadao Oida; Teruo Tanaka, both of Yokohama; Yawara Tajima, Kuki; Toshiyuki Konosu, Kawasaki; Atsushi Somada, Ohmiya; Takeo Miyaoka, Funabashi; Hiroshi Yasuda, Yokohama, all of (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/241,369

(22) Filed: Feb. 1, 1999

Related U.S. Application Data

(62) Division of application No. 08/944,304, filed as application No. PCT/JP96/00932 on Apr. 5, 1996, now abandoned.

(30) Foreign Application Priority Data

Apr. 6, 1995 (JP) .................................................. 7-81052

(51) Int. Cl.$^7$ ..................... C07D 249/08; C07D 401/12; C07D 403/12; C07D 405/12; A01N 43/653
(52) U.S. Cl. .................. 514/383; 514/255.05; 514/256; 514/269; 514/340; 514/374; 514/376; 514/377; 514/365; 514/369; 514/370; 544/405; 544/333; 544/324; 544/331; 544/310; 546/276; 548/225; 548/235; 548/233; 548/236; 548/182; 548/202; 548/193; 548/204; 548/205; 548/203; 548/194; 548/266.2; 548/266.6; 548/267.2; 548/268.6
(58) Field of Search ............................. 514/383, 255.05, 514/340, 377, 370; 548/267.2, 268.6, 266.2, 266.6, 203, 225, 233; 546/276; 544/405, 331

(56) References Cited

U.S. PATENT DOCUMENTS

| | | | |
|---|---|---|---|
| 4,505,919 | 3/1985 | Cooper et al. | 514/340 |
| 4,507,484 | 3/1985 | Gymer et al. | 546/210 |
| 4,661,507 | 4/1987 | Gymer et al. | 548/262 |
| 5,081,139 | 1/1992 | Saji et al. | 514/383 |
| 5,089,640 | 2/1992 | Böckmann et al. | 549/563 |
| 5,177,094 | 1/1993 | Itoh et al. | 514/383 |
| 5,387,599 | 2/1995 | Itoh et al. | 514/383 |
| 5,389,663 | 2/1995 | Itoh et al. | 514/383 |
| 5,393,769 | 2/1995 | Oida et al. | 514/383 |
| 5,489,606 | 2/1996 | Oida et al. | 514/383 |

FOREIGN PATENT DOCUMENTS

| | | |
|---|---|---|
| 0 140 154 | 5/1985 | (EP) . |
| 0 150 036 | 7/1985 | (EP) . |
| 178533 | 4/1986 | (EP) . |
| 180136 | 5/1986 | (EP) . |
| 0 332 387 | 9/1989 | (EP) . |
| 421210 | 4/1991 | (EP) . |
| 473387 | 3/1992 | (EP) . |
| 510700 | 10/1992 | (EP) . |
| 61-85369 | 4/1986 | (JP) . |
| 6-247944 | 9/1994 | (JP) . |

*Primary Examiner*—John M. Ford
(74) *Attorney, Agent, or Firm*—Frishauf, Holtz, Goodman, Langer & Chick, P.C.

(57) ABSTRACT

A triazole compound having the formula:

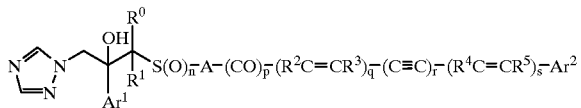

wherein Ar$^1$ represents a phenyl group which may be substituted, Ar$^2$ represents a heterocyclic group which may be substituted, R$^0$ represents a hydrogen atom or a lower alkyl; R$^1$ represents a lower alkyl; R$^2$ to R$^5$ each represent a hydrogen atom or an unsubstituted or halo substituted alkyl; n represents 0 to 2; p represents 0 or 1; q, r and s each represent 0 to 2; A represents a 4- to 7-membered carbon ring or a 4- to 7-membered heterocyclic group. The compound of the present invention exhibits an excellent antifungal activity.

43 Claims, No Drawings

TRIAZOLE ANTIFUNGAL AGENT

This application is a divisional application of application Ser. No. 08/944,304, filed Oct. 6 1997 (U.S. Pat. No. 5,977,152), which a continuation-in-part application of International application PCT/JP96/00932 filed Apr. 5, 1996, now abandoned which is hereby incorporated in its entirety.

The present invention relates to a 1,2,4-triazole compound represented by the formula (I) which is particularly effective for mycotic disease of a human being and an animal.

BACKGROUND OF THE INVENTION

In the Japanese Unexamined Patent Publication (KOKAI) No. Sho 61-85369, it is described that an analogous compound of the compound of the present invention, in which the following moiety (which corresponds to the right hand moiety of formula (I) which starts with —A—):

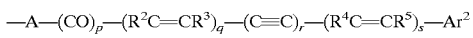

$$-A-(CO)_p-(R^2C=CR^3)_q-(C\equiv C)_r-(R^4C=CR^5)_s-Ar^2$$

is bonded to an alkyl, a cycloalkylalkyl group or a cycloalkyl group, has antifungal activities.

However, the present inventors made intensive studies in order to find a more excellent antifungal agent and found that the compound of the present invention is an excellent antifungal agent to accomplish the present invention.

SUMMARY OF THE INVENTION

The present invention relates to a compound having the formula (I):

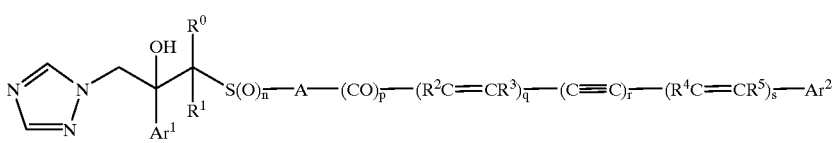

wherein $Ar^1$ represents a phenyl group or a phenyl group having 1 to 3 substituent(s), (the substituent(s) represent(s) a halogen atom or a trifluoromethyl group);

$Ar^2$ represents a phenyl group, a 5- or 6-membered aromatic heterocyclic group (the aromatic heterocyclic group has at least one nitrogen, oxygen or sulfur atom) or a phenyl group or a 5- or 6-membered aromatic heterocyclic group having 1 to 3 substituents (the substituent(s) represent(s) a lower alkyl group, a lower alkoxy group, a halogen atom, a lower alkyl group substituted with a halogen atom or halogen atoms, a lower alkoxy group substituted with a halogen atom or halogen atoms, a nitro group, a cyano group, a $S(O)_mR^6$ group ($R^6$ represents a lower alkyl group which may be substituted with a halogen atom or halogen atoms and m represents 0, 1 or 2) or a —$NECOR^7$ group ($R^7$ represents a lower alkyl group) and the aromatic heterocyclic group has at least one nitrogen, oxygen or sulfur atom];

$R^0$ represents a hydrogen atom or a lower alkyl group;

$R^1$ represents a lower alkyl group;

$R^2$, $R^3$, $R^4$ and $R^5$ may be the same or different and represent a hydrogen atom, a lower alkyl group or a lower alkyl group substituted with a halogen atom or halogen atoms and, where q and/or s represent 2, each of $R^2$, $R^3$, $R^4$ and $R^5$ represents independently a group which is the same or different from the other $R^2$, $R^3$, $R^4$ and $R^5$ respectively;

n represents 0, 1 or 2;

p represents 0 or 1;

g, r and s represent 0, 1 or 2; and

A represents a 4- to 7-membered aliphatic carbocyclic group comprising 4 to 7 carbon atoms or a 4- to 7-membered aliphatic heterocyclic group having at least one nitrogen, oxygen or sulfur atom, or a pharmacologically acceptable salt thereof.

The above-mentioned halogen atom is, for example, a fluorine, chlorine or bromine atom, preferably a fluorine or chlorine atom.

The lower alkyl group is, for example, a methyl, ethyl, propyl, isopropyl, butyl, isobutyl, sec-butyl or tert-butyl group, preferably a methyl, ethyl, propyl or isopropyl group.

The lower alkoxy group is, for example, a methoxy, ethoxy, propoxy, isopropoxy, butoxy, isobutoxy, sec-butoxy or tert-butoxy group, preferably a methoxy, ethoxy, propoxy or isopropoxy group.

The 5- or 6-membered aromatic heterocyclic group of $Ar^2$ is, for example, a furyl, thienyl, pyrrolyl, pyrazolyl, imidazolyl, oxazolyl, thiazolyl, pyridyl, pyrimidyl or pyrazyl group, preferably a furyl, thienyl, pyrrolyl or pyridyl group.

The 4- to 7-membered aliphatic carbocyclic group comprising 4 to 7 carbon atoms of A is, for example, a cyclobutane, cyclopentane, cyclohexare or cyclobutane ring, preferably a cyclobutane, cyclopentane or cyclohexane ring.

The 4- to 7-membered aliphatic heterocyclic group having at least one nitrogen, oxygen or sulfur atom of A is, for example, an azetidine, pyrrolidine, piperidine, homopiperidine, oxetane, tetrahydrofuran, tetrahydropyran, thietane, tetrahydrothiophene, pentamethylenesulfide, 1,4,5,6-tetrahydropyrimidine, 1,3-dioxane, 1,3-dithiane, dihydroxazine, tetrahydroxazine, dihydrothiazine or tetrahydrothiazine ring, preferably an azetidine, piperidine, 1,3-dioxane, 1,4,5,6-tetrahydropyrimidine, tetrahydroxazine or 1,3-dithiane ring.

The preferable compound having the formula (I) is the compound in which:

$Ar^1$ is a dichlorophenyl, difluorophenyl, chlorophenyl, fluorophenyl, (trifluoromethyl)phenyl or fluoro (trifluoromethyl)phenyl group, preferably a 2,4-dichlorophenyl, 2,4-difluorophenyl, 4-chlorophenyl, 4-fluorophenyl, 4-(trifluoromethyl)phenyl or 2-fluoro-4-(trifluoromethyl)phenyl group, particularly preferably a 2,4-dichlorophenyl, 2,4-difluorophenyl or 4-(trifluoromethyl)phenyl group;

$Ar^2$ is a fluorophenyl, chlorophenyl, difluorophenyl, dichlorophenyl, (trifluoromethyl)phenyl, (trichloromethyl)phenyl, fluoro-(trifluoromethyl) phenyl, (difluoromethoxy)phenyl, (trifluoromethoxy) phenyl, (2,2,2-trifluoroethoxy)phenyl, (1,1,2,2-tetrafluoroethoxy)phenyl, (2,2,3,3-tetrafluoropropoxy)

phenyl, fluoro-(2,2,3,3-tetrafluoropropoxy)phenyl, nitrophenyl, fluoro-nitrophenyl, cyanophenyl, chloro-cyanophenyl, (methylthio)phenyl, (methylsulfinyl)phenyl, (methylsulfonyl)phenyl, (trifluoromethylthio)phenyl, (trifluoromethylsulfinyl)phenyl, (trifluoromethylsulfonyl)phenyl, chloropyridyl, (trifluoromethyl)pyridyl, (2,2,3,3-tetrafluoropropoxy)pyridyl, (trifluoromethyl)furyl, chlorothienyl or (trifluoromethyl)thienyl group, preferably a 4-fluorophenyl, 4-chlorophenyl, 2,4-difluorophenyl, 2,4-dichlorophenyl, 4-(trifluoromethyl)phenyl, 4-(trichloromethyl)phenyl, 2-fluoro-4-(trifluoromethyl)phenyl, 4-(difluoromethoxy)phenyl, 3-(trifluoromethoxy)phenyl, 4-(trifluoromethoxy)phenyl, 4-(2,2,2-trifluoroethoxy)phenyl, 4-(1,1,2,2-tetrafluoroethoxy)phenyl, 4-(2,2,3,3-tetrafluoropropoxy)phenyl, 2-fluoro-4-(2,2,3,3-tetrafluoropropoxy)phenyl, 4-nitrophenyl, 2-fluoro-4-nitrophenyl, 4-cyanophenyl, 2-chloro-4-cyanophenyl, 4-(methylthio)phenyl, 4-(methylsulfinyl)phenyl, 4-(methylsulfonyl)phenyl, 4-(trifluoromethylthio)phenyl, 4-(trifluoromethylsulfinyl)phenyl, 4-(trifluoromethylsulfonyl)pheryl, 6-chloro-3-pyridyl, 6-(trifluoromethyl)-3-pyridyl, 5-chloro-2-pyridyl, 6-(2,2,3,3-tetrafluoropropoxy)-3-pyridyl, 5-(trifluoromethyl)-2-furyl, 5-chloro-2-thienyl or 5-(trifluoromethyl)-2-thienyl group, particularly preferably a 4-chlorophenyl, 4-(trifluoromethylthio)phenyl, 4-(trifluoromethylsulfonyl)phenyl, 4-(trifluoromethyl)phenyl, 4-(trifluoromethoxy)phenyl or 4-(2,2,3,3-tetrafluoropropoxy)phenyl group;

$R^0$ is a hydrogen atom, a methyl, ethyl or propyl group, preferably a hydrogen atom, a methyl or ethyl group, particularly preferably a hydrogen atom or a methyl group;

$R^1$ is a methyl, ethyl or propyl group, preferably a methyl or ethyl group, particularly preferably a methyl group;

$R^2$, $R^3$, $R^4$ and $R^5$ may be the same or different and are a hydrogen atom, a methyl, ethyl, propyl or trifluoromethyl group, preferably a hydrogen atom, a methyl or trifluoromethyl group, particularly preferably a hydrogen atom or a trifluoromethyl group;

n is 0, 1 or 2, particularly preferably 0;

p is 0 or 1, particularly preferably 0;

q is 0, 1 or 2, particularly preferably 1;

r is 0, 1 or 2, particularly preferably 0 or 1;

s is 0, 1 or 2, particularly preferably 1;

A is a cyclobutane, cyclopentane, cyclohexane, azetidine, pyrrolidine, piperidine, tetrahydrofuran, tetrahydropyran, tetrahydrothiophene, 1,3-dioxane, 1,3-dithiane, tetrahydroxazine or tetrahydrothiazine ring, preferably a cyclobutane, cyclohexane, azetidine, piperidine, 1,3-dioxane, 1,3-dithiane, tetrahydroxazine or tetrahydrothiazine ring, particularly preferably a cyclohexane, piperidine, 1,3-dioxane or 1,3-dithiane ring.

The preferable compound (I) can be exemplified by the compound in which $Ar^1$ is a 4-chlorophenyl, 2,4-difluorophenyl, 2,4-dichlorophenyl or 4-(trifluoromethyl)phenyl group; $R^0$ is a hydrogen atom or a methyl group; $R^1$ is a methyl group; and the moiety represented by the formula:

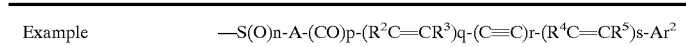

is a group as shown in Table 1.

TABLE 1

| Example | 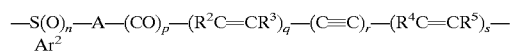 |
|---|---|
| 1 | 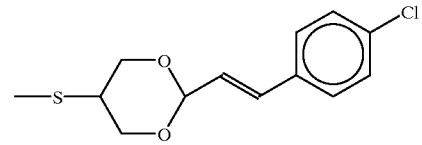 |
| 2 | 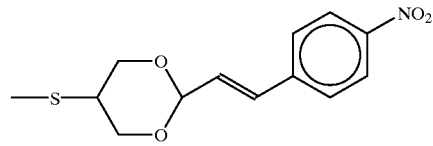 |
| 3 | 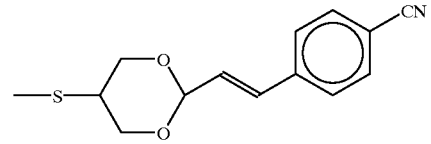 |
| 4 | 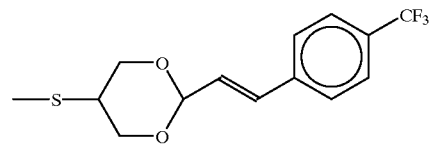 |

TABLE 1-continued
| Example | —S(O)n-A-(CO)p-(R$^2$C=CR$^3$)q-(C≡C)r-(R$^4$C=CR$^5$)s-Ar$^2$ |
|---|---|
| 5 | 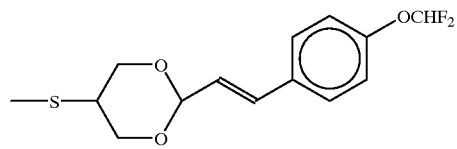 |
| 6 | 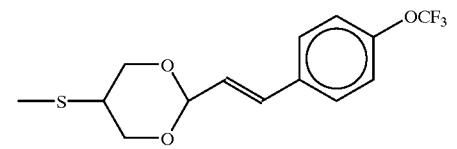 |
| 7 | 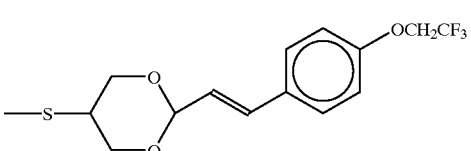 |
| 8 | 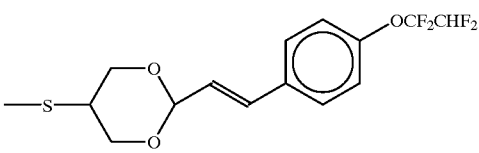 |
| 9 | 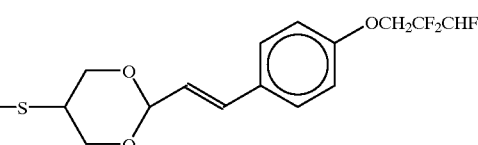 |
| 10 | 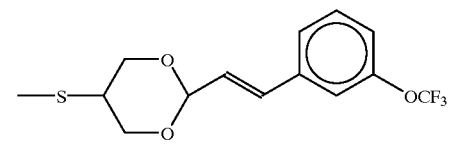 |
| 11 | 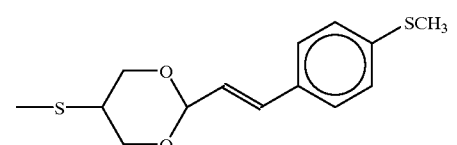 |
| 12 | 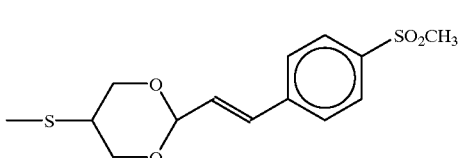 |
| 13 | 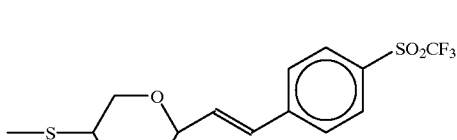 |

TABLE 1-continued

| Example | —S(O)n-A-(CO)p-(R$^2$C=CR$^3$)q-(C≡C)r-(R$^4$C=CR$^5$)s-Ar$^2$ |
|---|---|
| 14 | 1,3-dioxan-2-yl-CH=CH-(3,5-difluorophenyl), 5-methylthio |
| 15 | 1,3-dioxan-2-yl-C(CH$_3$)=CH-(4-trifluoromethylphenyl), 5-methylthio |
| 16 | 1,3-dioxan-2-yl-CH=C(CF$_3$)-(4-chlorophenyl), 5-methylthio |
| 17 | 1,3-dioxan-2-yl-CH=CH-(6-chloropyridin-3-yl), 5-methylthio |
| 18 | 1,3-dioxan-2-yl-CH=CH-(6-trifluoromethylpyridin-3-yl), 5-methylthio |
| 19 | 1,3-dioxan-2-yl-CH=CH-(5-trifluoromethylpyridin-2-yl), 5-methylthio |
| 20 | 1,3-dioxan-2-yl-CH=CH-(5-trifluoromethylfuran-2-yl), 5-methylthio |
| 21 | 1,3-dioxan-2-yl-CH=CH-(5-chlorothien-2-yl), 5-methylthio |
| 22 | 1,3-dioxan-2-yl-CH=CH-(5-trifluoromethylthien-2-yl), 5-methylthio |

TABLE 1-continued

| Example | —S(O)n-A-(CO)p-(R²C=CR³)q-(C≡C)r-(R⁴C=CR⁵)s-Ar² |
|---|---|
| 23 | CH₃-S-[1,3-dioxane-5-yl]-CH=CH-[thiophene-2-yl]-5-NO₂ |
| 24 | CH₃-S(O)-[1,3-dioxane-5-yl]-CH=CH-[phenyl]-4-CF₃ |
| 25 | CH₃-SO₂-[1,3-dioxane-5-yl]-CH=CH-[phenyl]-4-OCF₃ |
| 26 | CH₃-S-[tetrahydropyran-5-yl]-CH=CH-[phenyl]-4-CF₃ |
| 27 | CH₃-S-[tetrahydrothiopyran-5-yl]-CH=CH-[phenyl]-4-OCHF₂ |
| 28 | CH₃-S-[tetrahydrothiopyran-5-yl]-CH=C(CF₃)-[phenyl]-4-Cl |
| 29 | CH₃-S-[1,3-dithiane-5-yl]-CH=CH-[phenyl]-4-OCH₂CF₂CHF₂ |
| 30 | CH₃-S-[1,3-dithiane-5-yl]-CH=CH-[phenyl]-2-CH₃-4-CF₃ |
| 31 | CH₃-S-[1,3-dithiane-5-yl]-CH=CH-[phenyl]-2-OCH₃-4-CF₃ |

TABLE 1-continued

| Example | —S(O)n-A-(CO)p-(R²C=CR³)q-(C≡C)r-(R⁴C=CR⁵)s-Ar² |
|---|---|
| 32 | [structure: methylthio-1,3-dithiane with vinyl linker to 2-(trifluoromethoxy)pyridin-5-yl] |
| 33 | [structure: methylthio-1,3-dithiane with C(CF₃)=CH linker to 4-(difluoromethoxy)phenyl] |
| 34 | [structure: methylthio-1,3-oxathiane with vinyl linker to 2,4-difluorophenyl] |
| 35 | [structure: methylthio-1,3-oxathiane with vinyl linker to 4-(OCF₂CHF₂)phenyl] |
| 36 | [structure: methylthio-1,3-oxathiane with vinyl linker to 5-(trifluoromethyl)thiophen-2-yl] |
| 37 | [structure: methylthio-1,3-dioxane with C(=O)-CH=CH linker to 4-(trifluoromethyl)phenyl] |
| 38 | [structure: methylthio-1,3-dioxane with diene linker to 4-chlorophenyl] |
| 39 | [structure: methylthio-1,3-dioxane with diene linker to 2,4-difluorophenyl] |
| 40 | [structure: methylthio-1,3-dioxane with diene linker to 4-(trifluoromethyl)phenyl] |

TABLE 1-continued
| Example | —S(O)n-A-(CO)p-(R²C=CR³)q-(C≡C)r-(R⁴C=CR⁵)s-Ar² |
|---|---|
| 41 | 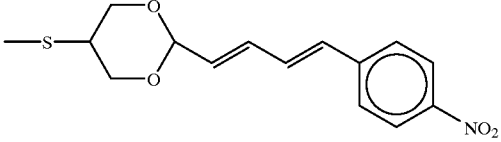 |
| 42 | 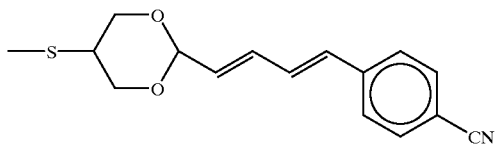 |
| 43 | 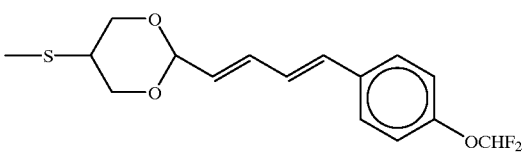 |
| 44 | 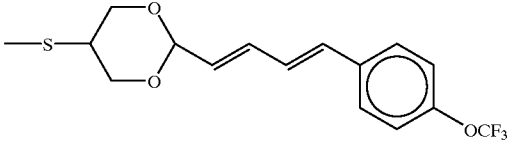 |
| 45 | 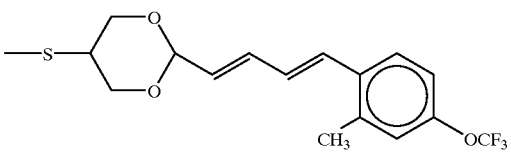 |
| 46 | 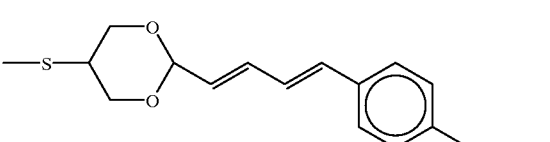 |
| 47 | 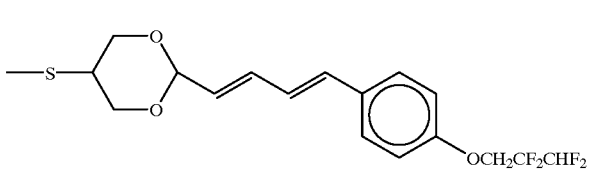 |
| 48 | 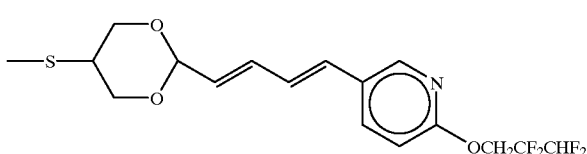 |
| 49 | 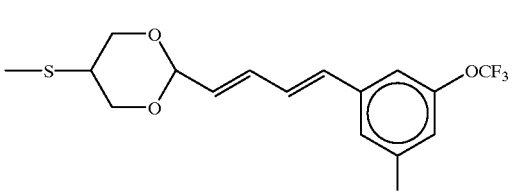 |

TABLE 1-continued
| Example | —S(O)n-A-(CO)p-(R²C=CR³)q-(C≡C)r-(R⁴C=CR⁵)s-Ar² |
|---|---|
| 50 | 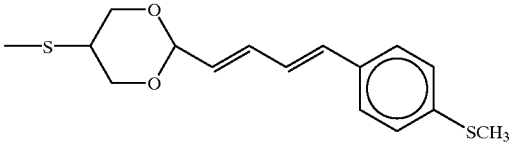 |
| 51 | 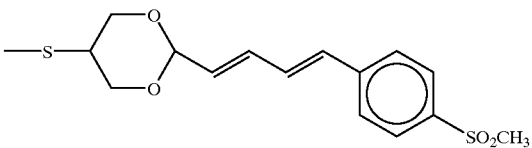 |
| 52 | 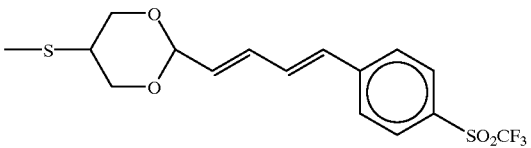 |
| 53 | 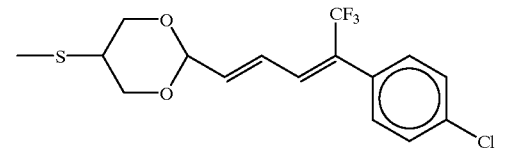 |
| 54 | 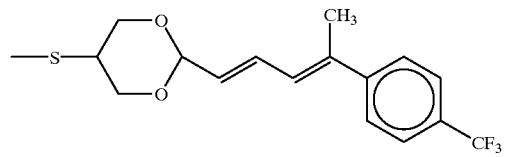 |
| 55 | 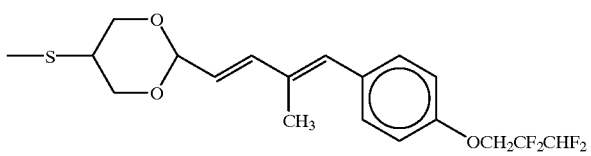 |
| 56 | 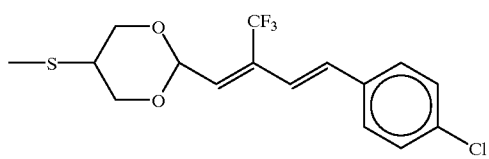 |
| 57 | 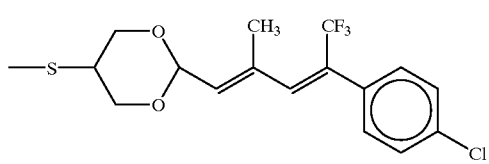 |
| 58 | 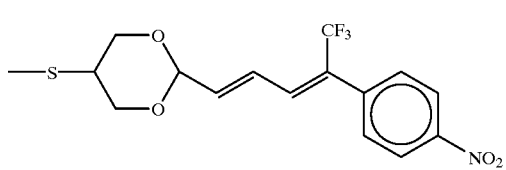 |

TABLE 1-continued

| Example | —S(O)n-A-(CO)p-(R²C=CR³)q-(C≡C)r-(R⁴C=CR⁵)s-Ar² |
|---|---|
| 59 | 1,3-dioxane-CH=CH-C(CF₃)=CH-(2-OCHF₂-pyridin-5-yl), S-substituted |
| 60 | 1,3-dioxane-CH=CH-C(CF₃)=CH-(4-OCH₂CF₂CHF₂-phenyl), S-substituted |
| 61 | 1,3-dithiane-CH=CH-CH=CH-(4-CF₃-phenyl), S-substituted |
| 62 | 1,3-dithiane-CH=CH-C(CF₃)=CH-(4-Cl-phenyl), S-substituted |
| 63 | 1,3-dithiane-CH=CH-CH=CH-(4-OCH₂CF₂CHF₂-phenyl), S-substituted |
| 64 | 1,3-dioxane-CH=CH-CH=CH-(2-Cl-pyridin-5-yl), S-substituted |
| 65 | 1,3-dioxane-CH=CH-CH=CH-(5-SO₂CF₃-thiophen-2-yl), S-substituted |
| 66 | 1,3-dioxane-CH=CH-CH=CH-(5-CF₃-thiophen-2-yl), S-substituted |
| 67 | 1,3-dioxane-CH=CH-C(CF₃)=CH-(5-Cl-thiophen-2-yl), S-substituted |

TABLE 1-continued

| Example | —S(O)n-A-(CO)p-(R²C=CR³)q-(C≡C)r-(R⁴C=CR⁵)s-Ar² |
|---|---|
| 68 | |
| 69 | |
| 70 | |
| 71 | |
| 72 | |
| 73 | |
| 74 | |
| 75 | |
| 76 | |
| 77 | |
| 78 | |

TABLE 1-continued
| Example | —S(O)n-A-(CO)p-(R²C=CR³)q-(C≡C)r-(R⁴C=CR⁵)s-Ar² |
|---|---|
| 79 | 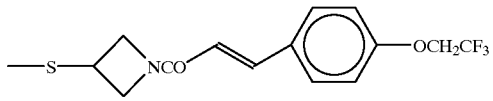 |
| 80 | 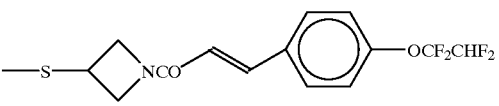 |
| 81 | 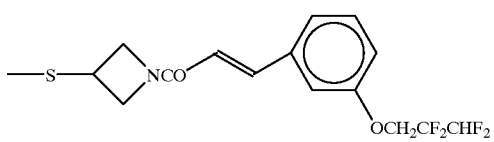 |
| 82 | 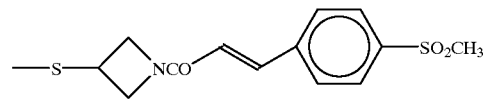 |
| 83 | 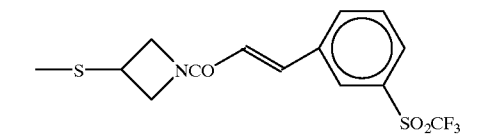 |
| 84 | 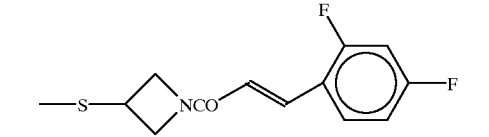 |
| 85 | 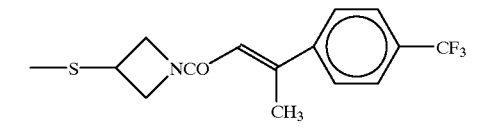 |
| 86 | 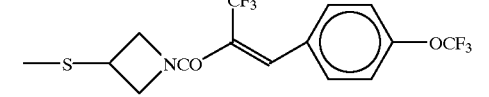 |
| 87 | 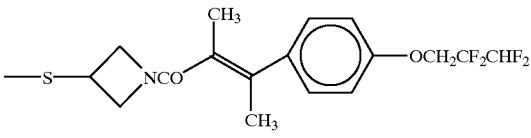 |
| 88 | 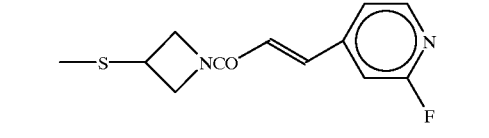 |
| 89 | 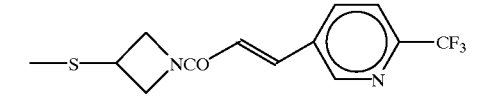 |

TABLE 1-continued

| Example | —S(O)n-A-(CO)p-(R²C=CR³)q-(C≡C)r-(R⁴C=CR⁵)s-Ar² |
|---|---|
| 90 | —S-[azetidine]-N-CO-O-C(CH₃)=CH-(pyridine)-OCF₃ |
| 91 | —S-[azetidine]-N-CO-O-C(CH₃)=CH-(furan)-CF₃ |
| 92 | —S-[azetidine]-N-CO-O-CH=C(CH₃)-(thiophene)-NO₂ |
| 93 | —S-[azetidine]-N-CO-O-C(CH₃)=CH-(thiophene)-CF₃ |
| 94 | —S-[azetidine]-N-CO-O-C(CF₃)=CH-(thiophene)-OCF₃ |
| 95 | —SO₂-[azetidine]-N-CO-O-CH=CH-(phenyl)-CF₃ |
| 96 | —S-[azetidine]-N-CO-O-CH=CH-CH=CH-(phenyl)-CF₃ |
| 97 | —S-[azetidine]-N-CO-O-CH=CH-CH=C(CF₃)-(phenyl)-OCF₃ |
| 98 | —S-[pyrrolidine]-N-CO-O-CH=CH-(phenyl)-F |
| 99 | —S-[pyrrolidine]-N-CO-O-CH=CH-(phenyl)-CN |
| 100 | —S-[pyrrolidine]-N-CO-O-CH=CH-(phenyl)-CF₃ |
| 101 | —S-[pyrrolidine]-N-CO-O-CH=CH-(phenyl)-OCF₃ |

TABLE 1-continued

| Example | —S(O)n-A-(CO)p-(R²C=CR³)q-(C≡C)r-(R⁴C=CR⁵)s-Ar² |
|---------|---------------------------------------------------|
| 102 | -S-[pyrrolidine]-NCO-CH=CH-C₆H₄-OCF₂CHF₂ |
| 103 | -S-[pyrrolidine]-NCO-CH=CH-C₆H₄-OCH₂CF₂CHF₂ |
| 104 | -S-[pyrrolidine]-NCO-CH=CH-(pyridyl)-CF₃ |
| 105 | -S-[pyrrolidine]-NCO-CH=CH-C₆H₄-SCH₃ |
| 106 | -S-[pyrrolidine]-NCO-CH=CH-C₆H₄-SO₂CH₃ |
| 107 | -S-[pyrrolidine]-NCO-CH=CH-C₆H₄-SO₂CF₃ |
| 108 | -S-[pyrrolidine]-NCO-CH=CH-C₆H₃(F)(CF₃) |
| 109 | -S-[pyrrolidine]-NCO-CH=C(CH₃)-C₆H₄-OCH₂CF₂CHF₂ |
| 110 | -S-[pyrrolidine]-NCO-C(CF₃)=CH-C₆H₃(Cl)(CF₃) |
| 111 | -S-[pyrrolidine]-NCO-CH=CH-(pyridyl)-Cl |
| 112 | -S-[pyrrolidine]-NCO-CH=CH-(pyridyl)-OCF₃ |

TABLE 1-continued

| Example | —S(O)n-A-(CO)p-(R²C=CR³)q-(C≡C)r-(R⁴C=CR⁵)s-Ar² |
|---------|--------------------------------------------------|
| 113 | |
| 114 | |
| 115 | |
| 116 | |
| 117 | |
| 118 | |
| 119 | |
| 120 | |
| 121 | |
| 122 | |
| 123 | |

TABLE 1-continued
| Example | —S(O)n-A-(CO)p-(R$^2$C=CR$^3$)q-(C≡C)r-(R$^4$C=CR$^5$)s-Ar$^2$ |
|---|---|
| 124 | 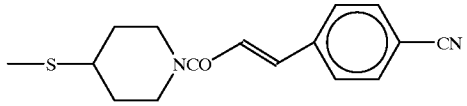 |
| 125 | 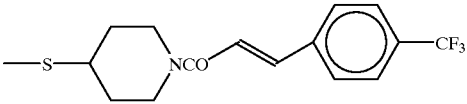 |
| 126 | 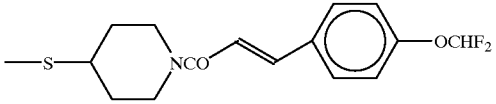 |
| 127 | 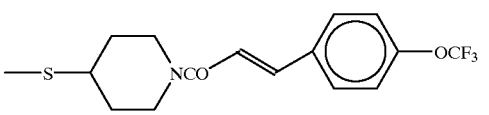 |
| 128 | 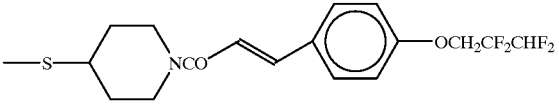 |
| 129 | 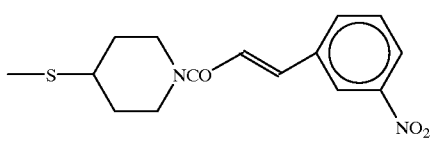 |
| 130 | 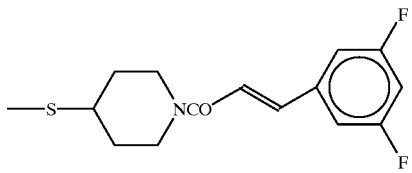 |
| 131 | 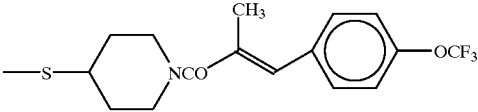 |
| 132 | 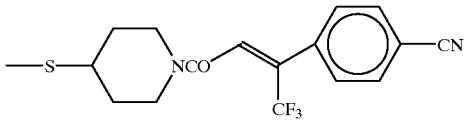 |
| 133 | 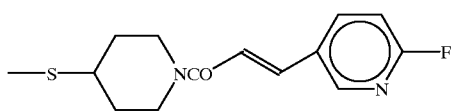 |
| 134 | 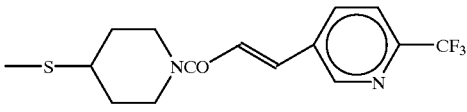 |

TABLE 1-continued
| Example | —S(O)n-A-(CO)p-(R²C=CR³)q-(C≡C)r-(R⁴C=CR⁵)s-Ar² |
|---|---|
| 135 | 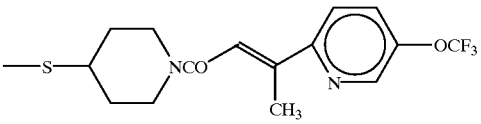 |
| 136 | 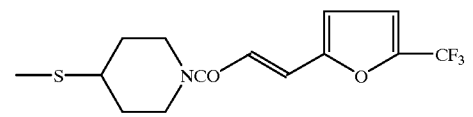 |
| 137 | 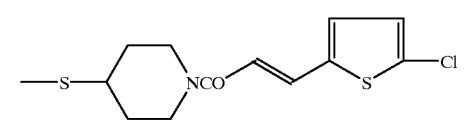 |
| 138 | 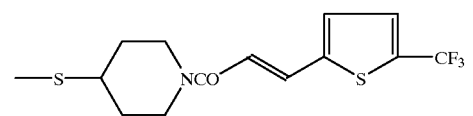 |
| 139 | 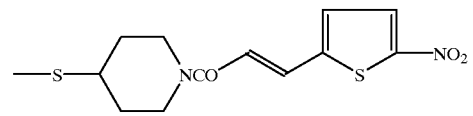 |
| 140 | 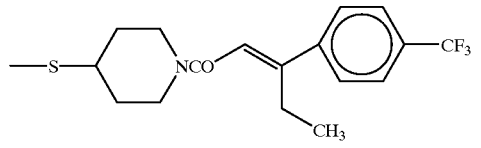 |
| 141 | 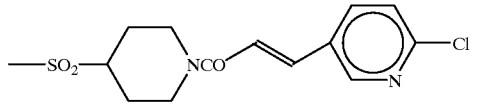 |
| 142 | 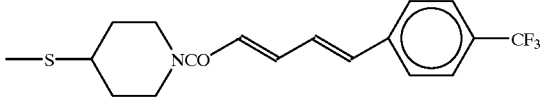 |
| 143 | 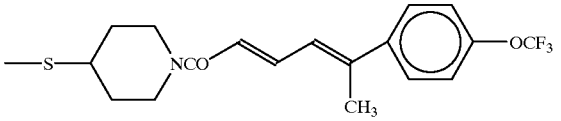 |
| 144 | 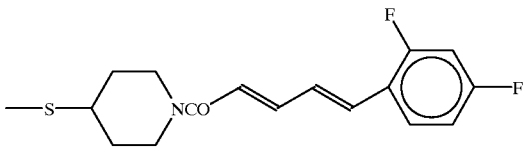 |
| 145 | 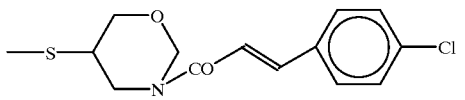 |

TABLE 1-continued

| Example | —S(O)n-A-(CO)p-(R²C═CR³)q-(C≡C)r-(R⁴C═CR⁵)s-Ar² |
|---|---|
| 146 | |
| 147 | |
| 148 | |
| 149 | |
| 150 | |
| 151 | |
| 152 | |
| 153 | |
| 154 | |
| 155 | |
| 156 | |

TABLE 1-continued

| Example | —S(O)n-A-(CO)p-(R²C=CR³)q-(C≡C)r-(R⁴C=CR⁵)s-Ar² |
|---|---|
| 157 | (structure: methylthio-dihydro-1,3-oxazine-CH=C(CH₃)-C₆H₄-OCF₃) |
| 158 | (structure: methylthio-dihydro-1,3-oxazine-CH=C(CH₃)-pyridine-CN) |
| 159 | (structure: methylthio-dihydro-1,3-oxazine-CH=C(CF₃)-furan-CF₃) |
| 160 | (structure: methylthio-dihydro-1,3-oxazine-C(CH₃)=C(CH₃)-thiophene-Cl) |
| 161 | (structure: methylthio-dihydro-1,3-oxazine-CH=C(CH₃)-CH=CH-C₆H₄-OCF₃) |
| 162 | (structure: methylthio-dihydro-1,3-oxazine-CH=CH-CH=CH-thiophene-CF₃) |
| 163 | (structure: methylthio-tetrahydropyrimidine-CH=CH-C₆H₄-F) |
| 164 | (structure: methylthio-tetrahydropyrimidine-CH=CH-C₆H₄-NO₂) |
| 165 | (structure: methylthio-tetrahydropyrimidine-CH=CH-C₆H₃(F)(CF₃)) |

TABLE 1-continued

| Example | —S(O)n-A-(CO)p-(R²C=CR³)q-(C≡C)r-(R⁴C=CR⁵)s-Ar² |
|---|---|
| 166 | |
| 167 | |
| 168 | |
| 169 | |
| 170 | |
| 171 | |
| 172 | |
| 173 | |
| 174 | |

TABLE 1-continued

| Example | —S(O)n-A-(CO)p-(R²C=CR³)q-(C≡C)r-(R⁴C=CR⁵)s-Ar² |
|---------|---------------------------------------------------|
| 175 | (1,3-dioxane-5-yl)-S-CH₃ with 2-position linked via CH=CH to 4-(S(O)CF₃)phenyl |
| 176 | (1,3-dioxane-5-yl)-S-CH₃ with 2-position linked via C≡C to 4-(CF₃)phenyl |
| 177 | (1,3-dioxane-5-yl)-S-CH₃ with 2-position linked via C≡C-CH=CH to 4-(CF₃)phenyl |
| 178 | (1,3-dioxane-5-yl)-S-CH₃ with 2-position linked via C≡C-CH=CH to 4-(OCH₂CF₂CHF₂)phenyl |
| 179 | (1,3-dioxane-5-yl)-S-CH₃ with 2-position linked via C≡C-CH=CH to 4-(SCF₃)phenyl |
| 180 | (1,3-dioxane-5-yl)-S-CH₃ with 2-position linked via CH=CH-C≡C to 4-(OCF₃)phenyl |
| 181 | (1,3-dioxane-5-yl)-S-CH₃ with 2-position linked via CH=CH-CH=CH to 4-(SCF₃)phenyl |
| 182 | (1,3-dioxane-5-yl)-S-CH₃ with 2-position linked via CH=CH-CH=CH to 4-(S(O)CF₃)phenyl |
| 183 | (1,3-dioxane-5-yl)-S-CH₃ with 2-position linked via CH=CH-CH=CH-CH=CH to 4-(CF₃)phenyl |
| 184 | (1,3-dioxane-5-yl)-S-CH₃ with 2-position linked via CH=CH-CH=CH-CH=CH to 4-(SCF₃)phenyl |

TABLE 1-continued

| Example | —S(O)n-A-(CO)p-(R²C=CR³)q-(C≡C)r-(R⁴C=CR⁵)s-Ar² |
|---|---|
| 185 | ![structure with —S-, 1,3-dioxane, triene, phenyl-OCF₃] |
| 186 | ![structure with —S-, 1,3-dioxane, triene, phenyl-OCH₂CF₂CHF₂] |
| 187 | ![structure with —S-, 1,3-dioxane, ene-yne-ene, phenyl-CF₃] |

Preferred compounds in Table 1 include those having the substituents of 4, 6, 7, 13, 16, 18, 22, 25, 32, 36, 40, 43, 44, 47, 52, 53, 61, 63, 71, 76, 96, 107, 123, 127, 142, 174, 176, 177, 178, 181, 182, 183 and 186, and particularly preferable compounds may include 2-(2,4-difluorophenyl)-3-[[2-[2-[4-(trifluoromethyl)phenyl]vinyl]-1,3-dioxan-5-yl]thio]-1-(H-1,2,4-triazol-1-yl)-2-butanol (the compound corresponding to Example 2), 2-(2,4-difluorophenyl)-1-(1H-1,2,4-triazol-1-yl)-3-[[2-[2-[4-(trifluoromethoxy)phenyl]vinyl]-1,3-dioxan-5-yl]thio]-2-butanol (the compound corresponding to Example 11), 2-(2,4-difluorophenyl)-1-((1H-1,2,4-triazol-1-yl)-3-[[2-[4-[4-(trifluoromethyl)phenyl]-1,3-butadien-1-yl]-1,3-dioxan-5-yl]thio]-2-butanol (the compound corresponding to Example 15), 2-(2,4-difluorophenyl)-3-[[2-[4-[4-(2,2,3,3-tetrafluoropropoxy)phenyl]-1,3-butadien-1-yl]-1,3-dioxan-5-yl]thio]-1-(1H-1,2,4-triazol-1-yl)-2-butanol (the compound corresponding to Example 16), 2-(2,4-difluorophenyl)-3-[[2-[4-[4-(chlorophenyl)-5,5,5-trifluoro-1,3-pentadien-1-yl]-1,3-dioxan-5-yl]thio]-1-(1H-1,2,4-triazol-1-yl)-2-butanol (the compound corresponding to Example 18), 2-(2,4-difluorophenyl)-3-[[1-[4-(trifluoromethoxy)cinnamoyl]piperidin-4-yl]thio]-1-(1H-1,2,4-triazol-1-yl)-2-butanol (the compound corresponding to Example 21), 2-(2,4-difluorophenyl)-3-[[1-[4-nitrocinnamoyl]piperidin-4-yl]thio]-1-(1H-1,2,4-triazol-1-yl)-2-butanol (the compound corresponding to Example 23), 2-(2,4-difluorophenyl)-1-(1H-1,2,4-triazol-1-yl)-3-[[1-[5-[4-(trifluoromethoxy)phenyl]-2,4-pentadienoyl]piperidin-4-yl]thio]-2-butanol (the compound corresponding to Example 24), 3-methyl-1-(1H-1,2,4-triazol-1-yl)-2-[4-(trifluoromethyl)phenyl]-3-[[2-[4-(trifluoromethyl)phenyl]-1,3-butadien-1-yl]-1,3-dioxan-5-yl]thio]-2-butanol (the compound corresponding to Example 31), 2-(2,4-difluorophenyl)-1-(1H-1,2,4-triazol-1-yl)-3-[[2-[4-(trifluoromethylthio)phenyl]-1,3-butadien-1-yl]-1,3-dioxan-5-yl]thio]-2-butanol (the compound corresponding to Example 32), 3-[[2-[4-[4-(2,2,3,3-tetrafluoropropoxy)phenyl]-1,3-butadien-1-yl]-1,3-dioxan-5-yl]thio]-1-(1H-1,2,4-triazol-1-yl)-2-[4-(trifluoromethyl)phenyl]-2-butanol (the compound corresponding to Example 33), 1-(1H-1,2,4-triazol-1-yl)-2-[4-(trifluoromethyl)phenyl]-3-[[2-[4-[4-(trifluoromethyl)phenyl]-1,3-butadien-1-yl]-1,3-dioxan-5-yl]thio]-2-butanol (the compound corresponding to Example 34), 2-(2,4-difluorophenyl)-1-(1H-1,2,4-triazol-1-yl)-3-[[2-[4-[4-(trifluoromethylsulfinyl)phenyl]-1,3-butadien-1-yl]-1,3-dioxan-5-yl]thio]-2-butanol (the compound corresponding to Example 35), 2-(2,4-difluorophenyl)-1-(1H-1,2,4-triazol-1-yl)-3-[[4-[4-(trifluoromethyl)phenyl]-1,3-butadien-1-yl]-cyclohexyl]thio]-2-butanol (the compound corresponding to Example 36), 2-(2,4-difluorophenyl)-1-(1H-1,2,4-triazol-1-yl)-3-[[2-[6-[4-(trifluoromethyl)phenyl]-1,3,5-hexatrien-1-yl]-1,3-dioxan-5-yl]thio]-2-butanol (the compound corresponding to Example 37), 2-(2,4-difluorophenyl)-3-methyl-1-(1H-1,2,4-triazol-1-yl)-3-[[2-[4-[4-(trifluoromethyl)phenyl]-1,3-butadien-1-yl]-1,3-dioxan-5-yl]thio]-2-butanol (the compound corresponding to Example 38) and 2-(2,4-difluorophenyl)-1-(1H-1,2,4-triazol-1-yl)-3-[[2-[4-[4-(trifluoromethyl)phenyl]-1-buten-3-yn-1-yl]-1,3-dioxan-5-yl]thio]-2-butanol (the compound corresponding to Example 39).

The triazole compound (I) of the present invention has at least two asymmetric carbon atoms, and optical isomers and diastereomers exist. In the optical isomer, both antipodes can be obtained by general optical resolution or asymmetric synthesis. Further, the diastereomers can be separated by conventional separation methods such as fractional recrystallization and chromatography. The compound (I) of the present invention includes one of these isomers or mixtures thereof.

The triazole compound (I) of the present invention can be used as an antifungal agent as such or in the form of a pharmacologically acceptable salt. The pharmacologically acceptable salt of the compound (I) includes, for example, a salt of inorganic acids such as hydrochloric acid, hydrobromic acid, sulfuric acid and nitric acid, a salt of carboxylic acids such as acetic acid, fumaric acid, maleic acid, oxalic acid, malonic acid, succinic acid, citric acid and malic acid, a salt of sulfonic acids such as methanesulfonic acid, ethanesulfonic acid, benzenesulfonic acid and toluenesulfonic acid and a salt of amino acids such as glutamic acid and aspartic acid, preferably a salt of carboxylic acids.

Incidentally, a hydrate of the compound (I) and a hydrate of the salt of the compound (I) are also included in the compound of the present invention.

The compound (I) and a pharmacologically acceptable salt thereof of the present invention exhibit excellent antifungal activities and in the case where the compound (I) and a pharmacologically acceptable salt thereof are used as an antifungal agent, they can be administered as such or as a mixture, for example, with a suitable pharmacologically acceptable excipient or diluent orally in the form of a tablet, a capsule, a granule, a powder or a syrup or parenterally in the form of injection preparations.

These preparations are prepared by the knowr method using additives such as excipients (for example, sugar derivatives such as lactose, sucrose, glucose, mannitol and sorbitol; starch derivatives such as corn starch, mashed potato starch, a-starch, dextrine and carboxymethyl starch; cellulose derivatives such as crystalline cellulose, low hydroxypropyl-substituted cellulose, hydroxypropylmethyl cellulose, carboxymethyl cellulose, carboxymethyl cellulose calcium and internally bridged carboxymethyl cellulose sodium; sum arabic; dextran; Pullulan; silicate derivatives such as light silicic acid anhydride, synthetic aluminum silicate and magnesium meta-silicic acid aluminate; phosphate derivatives such as calcium phosphate; carbonate derivatives such as calcium carbonate; and sulfate derivatives such as calcium sulfate), binders (for example, the above excipients; gelatin; polyvinylpyrrolidone; and Macrogol); disintegrating agents (for example, the above excipients; chemically modified starch-cellulose derivatives such as Crosscarmelose sodium, sodium carboxymethyl starch and bridged polyvinylpyrrolidone), lubricants (for example, talc; stearic acid; and metal stearates such as calcium stearate and magnesium stearate; colloidal silica; waxes such as beeswax and spermaceti; boric acid; glycol; carboxylic acid such as fumaric acid and adipic acid; sodium carboxylate such as sodium benzoate; sulfates such as sodium sulfate; leucine; lauryl sulfates such as sodium laurylsulfate and magnesium laurylsulfate; silicic acids such as silicic acid anhydride and silicic acid hydrate; and starch derivatives in the above excipients), stabilizers (for example, p-hydroxybenzoates such as methylparaben and propylparaben; alcohols such as chlorobutanol, benzyl alcohol and phenylethyl alcohol; benzalkonium chloride; phenols such as phenol and cresol; thimerosal; acetic anhydride; and sorbic acid); corrigents (for example, sweeteners, sour agents and perfumes conventionally used), suspending agents (for example, polysorbate 80 and carboxymethyl cellulose sodium), diluents and solvents for preparations (for example, water, ethanol and glycerin). While the dose varies depending on the condition and age of the patient to be treated, it is desirably administered 1 to 6 times daily depending on the condition: in the case of oral administration, the lower limit of 1 mg each time (preferably S mg) and the upper limit of 2000 mg (preferably 1000 mg) for an adult; and in the case of intravenous administration, the lower limit of 0.1 mg each time (preferably 0.5 mg) and the upper limit of 600 mg (preferably 500 mg) for an adult.

Among the compounds having the formula (I) of the present invention, the compound (Ia) in which $R^0$ is a hydrogen atom and n=0 can be prepared according to the process shown below:

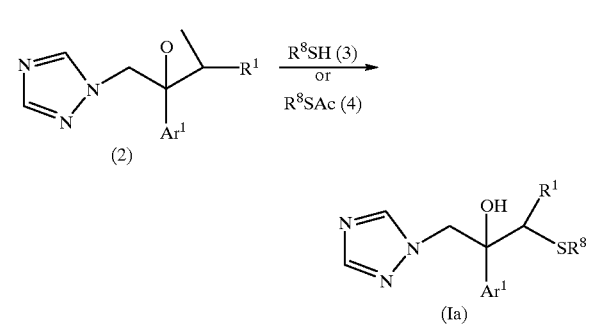

(wherein $Ar^1$ and $R^1$ have the same meanings as defined above and $R^8$ represents the formula:

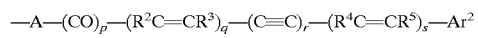

described above). More specifically, the desired compound (Ia) is prepared by reacting an epoxide compound (2) described in Japanese Unexamined Patent Publication (KOKAI) No. Hei 2-191262 (Jul. 27, 1990) with mercaptan (3) or an acetic acid ester derivative thereof under basic conditions. The solvent employable in the reaction includes preferably alcohols such as methanol, ethanol and propanol, aprotic solvents such as dimethylformamide, dimethylacetamide, dimethyl sulfoxide, acetonitrile and tetrahydrofuran. However, in the case where the reaction is carried out in the above aprotic solvent using an acetyl derivative (4), it is required to coexist alcohols or water. The base employable in the reaction includes sodium hydride, sodium methoxide, sodium ethoxide, lithium methoxide, potassium tert-butoxide, lithium hydroxide, sodium hydroxide and potassium hydroxide. The amount to be used is 0.1 to 2 molar equivalents based on the compound (2). Mercaptan (3) or the acetic acid derivative thereof (4) is used in 1 to 3 molar equivalents. The reaction temperature is room temperature to 1000C and the reaction time is 2 to 10 hours. The compound (Ia) can be obtained by treating the reaction mixture by conventional procedures (an oil obtained by extraction with an organic solvent and then evaporation of the solvent is purified by column chromatography or recrystallization).

Incidentally, $R^8SH$ (3) or $R^8SAc$ (4) used in the above reaction can be obtained according to the process shown below. More specifically, the compound (3) or (4) in which A in $R^8$ is a 1,3-dioxane ring and p=0 can be prepared using the known compound (5) [reference: O. E. van Lohuizen, P. E. Verkade, Rec. trav. chim., 78, 460 (1959)] as a starting material according to the scheme shown below (with respect to the reaction conditions and the isolation method in each step, see Reference examples 3, 4, 5, 6 and 7):

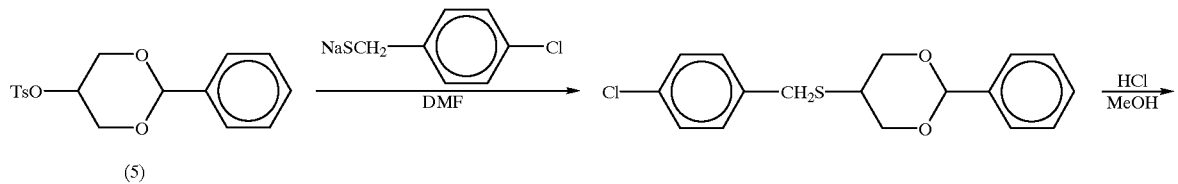

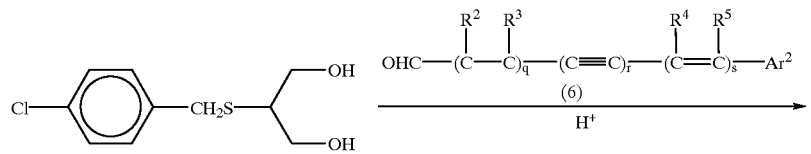

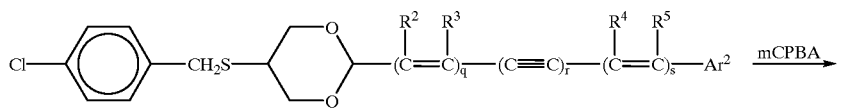

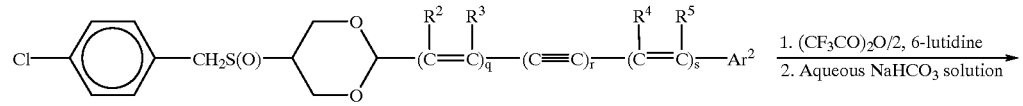

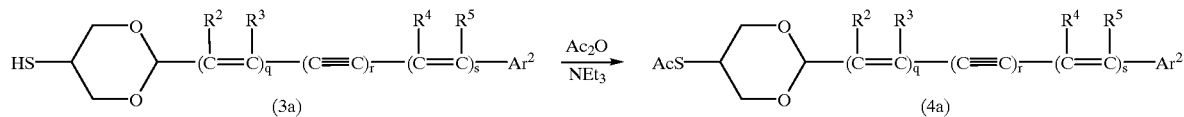

(wherein $R^2$, $R^3$, $R^4$, $R^5$, $Ar^2$, q, r and s have the same meanings as defined above). Among the unsaturated aldehydes (6) used in the above reaction, the compound (6a) in which r=0 can be generally obtained through an unsaturated ester (7a) according to the process shown below (with respect to the reaction conditions and the isolation method in each step, see Reference examples 8, 9, 10, 20, 21, 22, 23, 33 and 49):

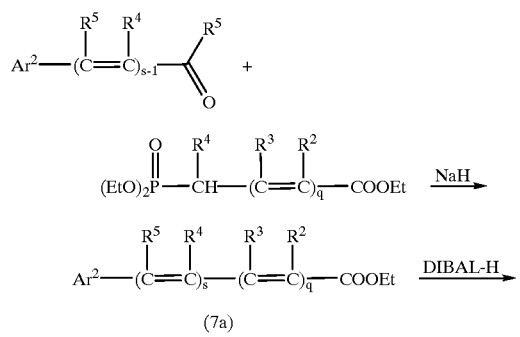

-continued

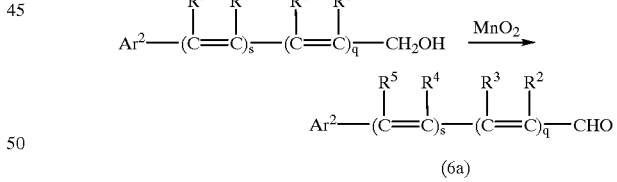

(wherein $R^2$, $R^3$, $R^4$, $R^5$, $Ar^2$, q and s have the same meanings as defined above and DIBAL-H represents diisobutyl aluminum hydride).

Among the unsaturated aldehydes (6), the compound (6b) in which r=1 or 2 can be generally obtained through an unsaturated ester (7b) according to the process shown below (with respect to the reaction conditions and the isolation method in each step, see Reference examples 44, 45, 46, 47 and 48):

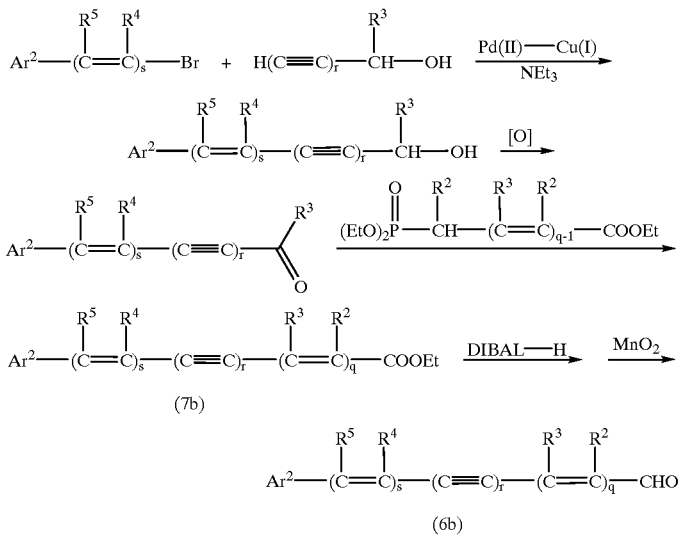

(wherein $R^2$, $R^3$, $R^4$, $R^5$, q, r and s have the same meanings as defined above and DIBAL-H represents diisobutyl aluminum hydride).

Further, the compound (3b) or (4b) in which A in $R^8$ of $R^8SH$ (3) or $R^8SAc$ (4) is a 4- to 7-membered nitrogen-containing heterocyclic group (azetidine, pyrrolidine, piperidine, homopiperidine) and p=1 can be obtained according to the process shown below (with respect to the reaction conditions and the isolation method in each step, see Reference examples 16 and 17):

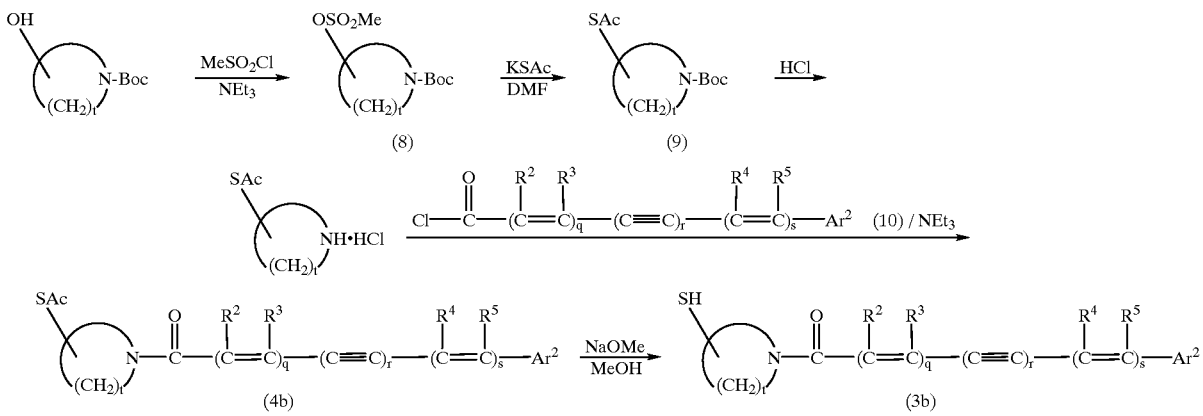

(wherein $R^2$, $R^3$, $R^4$, $R^5$, q, r and s have the same meanings as defined above, t represents 3, 4, 5 or 6 and Boc represents tert-butoxycarbonyl).

The acid chloride (10) used in the above reaction can be obtained by treating a carboxylic acid, obtained by alkali-decomposing the unsaturated ester (7a) or (7b) described above, with thionyl chloride.

Among the compounds having the formula (I) of the present invention, the compound (Ia) in which $R^0$ is a hydrogen atom and n=0 can be also obtained according to the process shown below

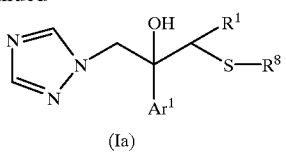

-continued (Ia)

(wherein $Ar^1$, $R^1$ and $R^8$ have the same meanings as defined above and X represents a chlorine, bromine or iodine atom, methanesulfonyloxy, benzenesulfonyloxy or toluenesulfonyloxy). More specifically, the process is to prepare the desired compound (Ia) by reacting a triazolylmercapto alcohol derivative (11) described in Japanese Unexamined Patent Publication (KOKAI) No. Hei 3-240778 (Oct. 28, 1991) with an alkylating agent (12) under basic conditions. The solvent employable in the reaction includes methanol, ethanol, propanol, butanol, dimethylformamide, dimethylacetamide, dimethyl sulfoxide, acetonitrile, tetrahydrofuran, dioxane, diethyl ether, acetone, benzene, toluene, xylene, etc. The base employable in the reaction includes triethylamine, diisopropylethylamine, sodium hydride, sodium methoxide, sodium ethoxide, lithium methoxide, potassium tert-butoxide, sodium hydroxide, potassium hydroxide, etc., and the amount used is 1 to 3 molar equivalents based on the compound (11). The alkylating reagent(12) is used in 1 to 3 molar equivalents. The reaction temperature is −50 to 100° C. and the reaction time is 2 to 10 hours. The compound (Ia) can be obtained by treating the reaction mixture by conventional procedures (an oil obtained by extraction with an organic solvent and then evaporation of the solvent is purified by column chromatography or recrystallization).

The alkylating reagent $R^8$-X (12) used in the above reaction can be obtained according to the process shown below. The compound (12a) in which A in $R^8$ is a 1,3-dioxane ring and p=0 can be obtained, for example, by reacting a diol compound (13), obtained by treating the above compound (5) with an acid in methanol, with the above unsaturated aldehyde (6) under acidic conditions (Reference example Nos. 56 and 57):

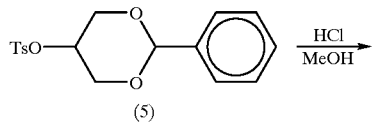

(5)

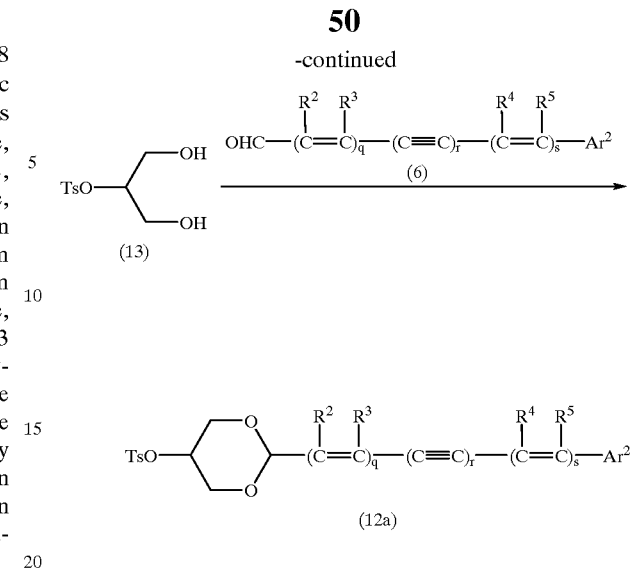

(wherein $R^2$, $R^3$, $R^4$, $R^5$, $Ar^2$, q, r and s have the same meanings as defined above). Further, the compound (12b) in which A in $R^8$ is a 4- to 7-membered nitrogen-containing heterocyclic group (azetidine, pyrrolidine, piperidine, homopiperidine) and p=1 can be obtained, for example, by reacting a compound (14) obtained by treating the above cyclic amine derivative (8) with HCl, with the above acid chloride (10) in the presence of a base such as triethylamine:

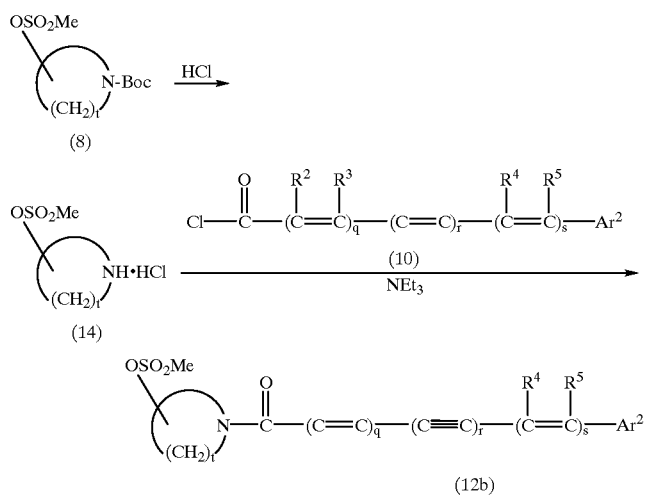

(wherein $R^2$, $R^3$, $R^4$, $R^5$, $Ar^2$, q, r, s and t have the same meanings as defined above).

Among the compounds having the formula (I) of the present invention, the compound (Ib) in which $R^0$ is a hydrogen atom, n=0, p=0 and A is a 1,3-dioxane ring can be also prepared according to the process shown below:

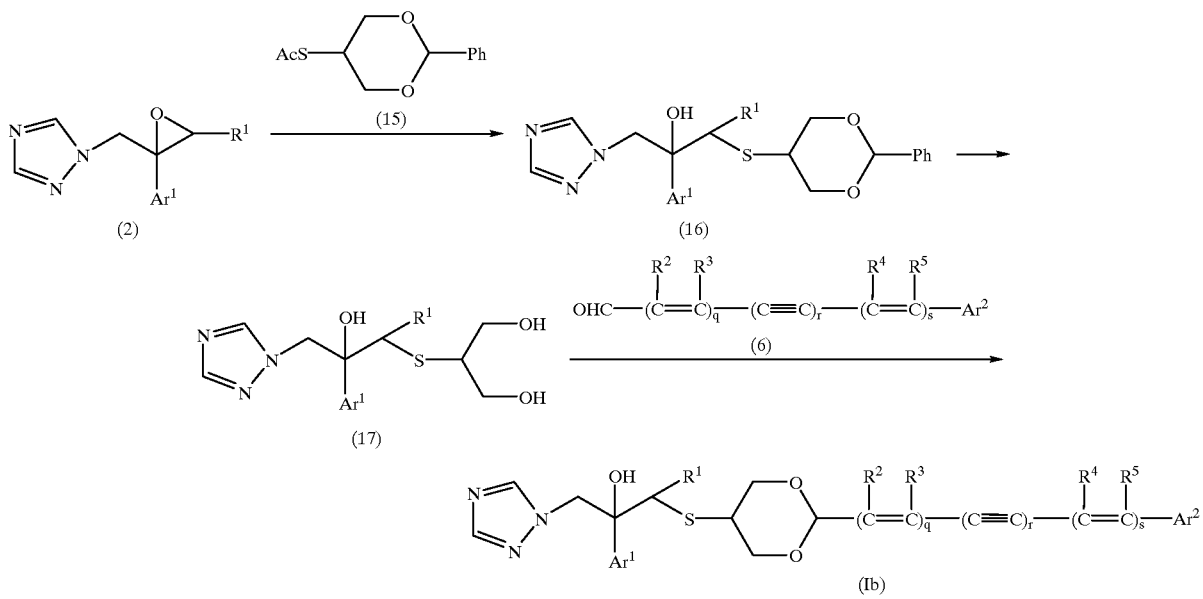

(wherein $Ar^1$, $Ar^2$, $R^1$, $R^2$, $R^3$, $R^4$, $R^5$, p, q and r have the same meanings as defined above). More specifically, the process is to prepare the desired compound (Ib) by reacting the above epoxide compound (2) with a thioacetic acid derivative (15) obtained by the reaction of the above known compound (5) with sodium thioacetate under the same conditions as in the reaction of (2) and (4) to obtain the compound (16), deprotecting the compound (16) according to conventional procedures such as the treatment with an acid to obtain the compound (17) and reacting the compound (17) with the above aldehyde compound (6). The reaction of the compounds (17) and (6) is usually carried out under acidic conditions. The acid employable here includes, for example, hydrogen chloride, sulfuric acid, nitric acid, boron trifluoride, methanesulfonic acid, benzenesulfonic acid and p-toluenesulfonic acid and the amount of the acid used is 1 to 2 molar equivalents based on (17). The aldehyde (6) is used in 1 to 2 molar equivalents. As the solvent, aprotic solvents such as methylene chloride, chloroform, 1,2-dichloroethane, benzene, toluene, xylene, diethyl ether and tetrahydrofuran are used. The reaction is carried out in the range of 0° C. to a boiling point of the solvent and the reaction time is 2 to 10 hours. While water produced by the reaction can be removed by azeotropic distillation, molecular sieves may be used as a dehydrating agent. The compound (Ib) can be obtained by neutralizing the reaction mixture with an aqueous sodium hydrogencarbonate solution and then treating it by conventional procedures (an oil obtained by extraction with an organic solvent and then evaporation of the solvent is purified by column chromatography or recrystallization).

Among the compounds of the present invention, the compound (Ic) in which $R^0$ is a hydrogen atom, n=0, p=1 and A is a 4- to 7-membered nitrogen-containing heterocyclic group (azetidine, pyrrolidine, piperidine, homopiperidine) car be obtained according to the process shown below:

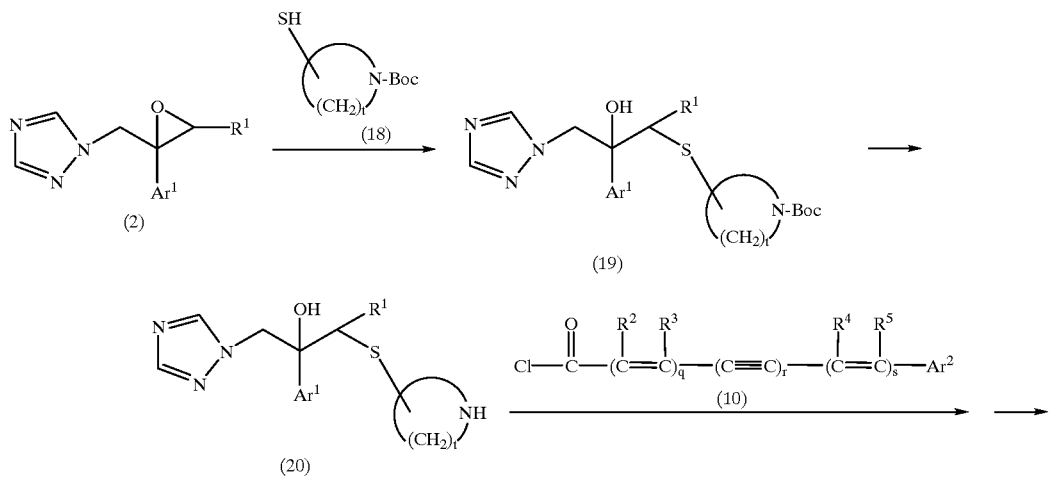

-continued

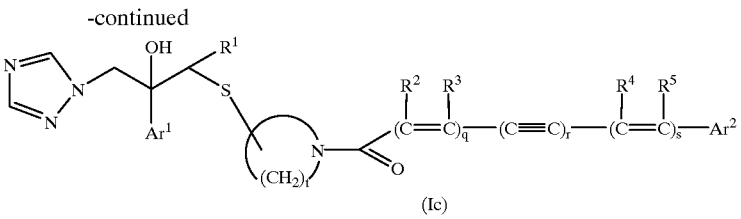

(Ic)

(wherein $Ar^1$, $Ar^2$, $R^1$, $R^2$, $R^3$, $R^4$, $R^5$, q, r, s and t have the same meanings as defined above and Boc represents tert-butoxy carbonyl). More specifically, the process is to prepare the desired compound (Ic) by reacting the above epoxide compound (2) with the mercaptan compound (18), obtained by treating the above thioacetic acid derivative (9) with an alkali, under the same conditions as in the reaction of (2) and (3) to obtain the compound (19), deprotecting (19) by treating it with an acid according to conventional procedures to obtain the compound (20) and reacting the compound (20) with the above acid chloride (10). The reaction of compounds (20) and (10) is carried out in an inert solvent such as benzene, toluene, methylene chloride, chloroform or tetrahydrofuran in the presence of an appropriate base by conventional procedures (Reference example Nos. 13, 14, 18 and 19).

Among the compounds (I) of the present invention, the compound in which n=1 or n=2 can be prepared according to the process mentioned below. More specifically, the compound (I) in which n=1 can be prepared by oxidizing the compound (I) in which n=0 obtained by the above process in a solvent using 1 equivalent of an oxidizing agent, and the compound (I) in which n=2 can be prepared by oxidizing it using 2 or more equivalents of an oxidizing agent. The solvent employable here is not particularly limited so long as it does not inhibit the reaction and dissolves the starting materials to some extent and may include preferably a halogenated hydrocarbon such as methylene chloride and chloroform. The oxidizing agent employable here may include, for example, peracetic acid and 3-chloroperbenzoic acid. The reaction is carried out at 0 to 50° C., preferably at room temperature, and the reaction time is usually 30 minutes to 2 hours. The compound (I) (n=1 or 2) can be obtained by treating the reaction mixture according to conventional procedures (after the reaction mixture is washed with aqueous sodium hydrogencarbonate, the crude product obtained by evaporation of the solvent is purified by chromatography or recrystallization).

Among the compounds having the formula (I) of the present invention, the compound (Id) in which $R^0$ is lower alkyl and n=0 can be prepared according to the process shown below:

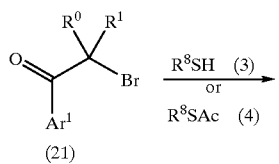

(21)

-continued

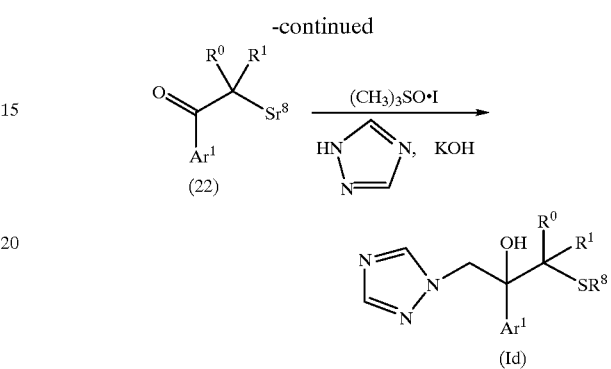

(Id)

(wherein $Ar^1$, $R^0$, $R^1$ and $R^8$ have the same meanings as defined above). More specifically, the desired compound (Id) is prepared by reacting bromoketone (21), obtained according to the procedures described in Japanese Unexamined Patent Publication (KOKAI) No. Hei 7-2802 (Jan. 6, 1995), with the above mercaptan (3) or an acetic acid derivative thereof (4) under alkaline conditions to obtain a thioether derivative (22) and reacting (22) with trimethylsulfoxonium iodide and 1,2,4-triazole in the presence of a base. The solvent used in the reaction of (21) and (3) or (4) includes preferably alcohols such as methanol, ethanol and propanol, and the alkali employable here includes sodium hydroxide, potassium hydroxide, sodium methoxide and sodium ethoxide. The solvent used in the reaction for converting the thioether derivative (22) to (Id) includes preferably alcohols such as methanol, ethanol, propanol, butanol and t-butanol and aprotic solvents such as dimethylformamide, dimethylacetamide, dimethyl sulfoxide, acetonitrile and tetrahydrofuran. The base used in the reaction includes sodium hydride, sodium methoxide, sodium ethoxide, lithium methoxide, potassium tert-butoxide, lithium hydroxide, sodium hydroxide and potassium hydroxide, and the amount used is 2 to 5 molar equivalents based on the compound (22). Trimethylsulfoxonium iodide and 1,2,4-triazole are used in 1 to 2 molar equivalents based on the compound (22), respectively. The reaction temperature is room temperature to 100° C. and the reaction time is 2 to 10 hours. The compound (Id) (n=0) can be obtained by treating the reaction mixture by conventional procedures (a crude product obtained by extraction with an organic solvent and then evaporation of the solvent is purified by column chromatography or recrystallization). Among the compounds (I), the compound (Ie) in which n=0, p=0 and A is a 1,3-dioxane ring can be obtained from the compound (23) in which $R^8$ is a group represented by the formula:

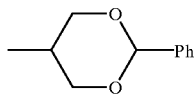

5 in the compound (Id) obtained by the above process through a triol (24) according to the process shown below:

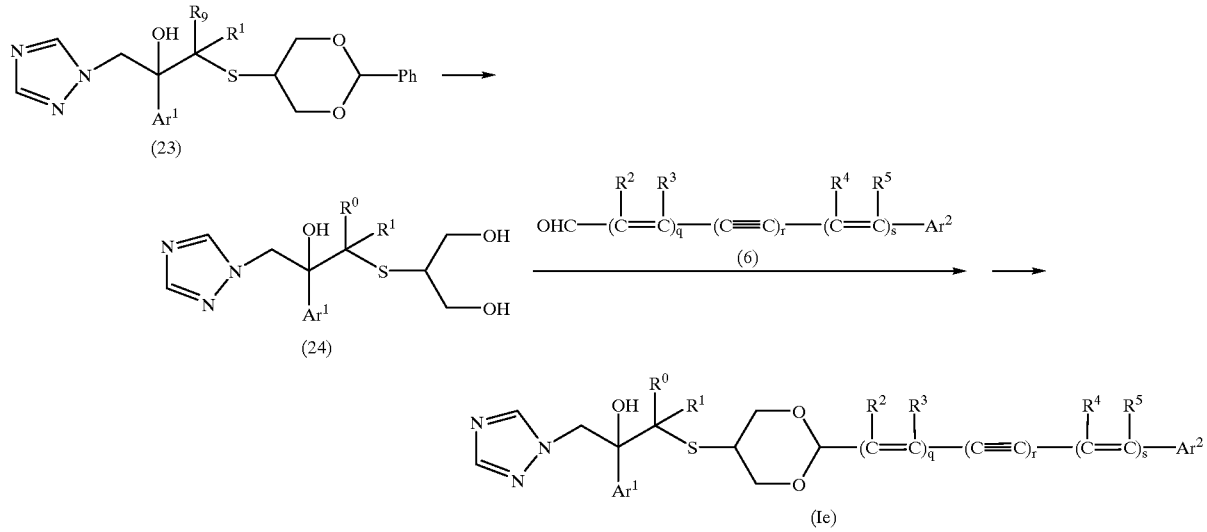

(wherein $R^0$ represents lower alkyl and $Ar^1$, $Ar^2$, $R^1$, $R^2$, $R^3$, $R^4$, $R^5$, q, r and s have the same meanings as defined above). The reaction conditions in the above respective steps are the same as those described in the reaction of (16)→(17)→(Ib).

The present invention will be explained below in more detail by referring to Examples, Reference examples, Test examples and Preparation examples but the scope of the present invention is not limited thereto.

Incidentally, the aldehyde compounds used in Examples are synthesized according to the procedures described in the literature and/or the citation of the literature in the cases where the literature is indicated in parenthesis. The aldehyde compounds for which the literature is not indicated are commercially available or can be obtained by the procedures for synthesizing an aldehyde which are described in the literature in the parenthesis of Examples or are described in the citation of the literature or a process according to the procedures for synthesizing an aldehyde described in Reference example of the present specification.

BEST MODE FOR PRACTICING THE INVENTION

EXAMPLE 1

(2R,3R)-2-(2,4-Difluorophenyl)-3-[[trans-2-[(E)-1-methyl-2-[4-(trifluoromethyl)phenyl]vinyl]-1,3-dioxan-5-yl]thio]-2-butanol

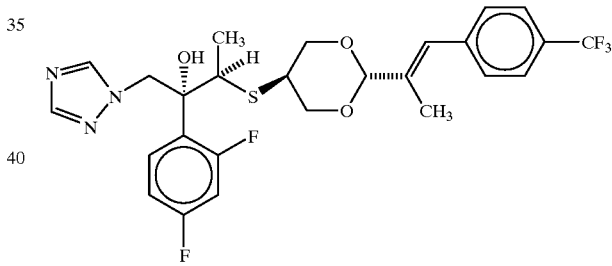

In 2 ml of dimethylformamide were dissolved 166 mg (0.48 mmol) of trans-4-(acetylthio)-2-[(E)-1-methyl-2-[4-(trifluoromethyl)phenyl]vinyl]-1,3-dioxane as described in Reference example 7 and 110 mg (0.44 mmol) of (2R,3S)-2-(2,4-difluorophenyl)-3-methyl-2-[(1H-1,2,4-triazol-1-yl) methyl]oxirane, and 0.15 ml (0.24 mmol) of a 1.6M sodium methoxide-methanol solution were added thereto under nitrogen atmosphere, followed by stirring of the resulting mixture at 55° C. for 6 hours. After cooling, ethyl acetate was added to the reaction mixture to dilute it and the resulting mixture was washed with a saturated aqueous NaCl solution. An oil obtained by distilling off the solvent was subjected to column chromatography using 15 g of silica gel and was eluted by a mixed solvent of hexane-ethyl acetate (2:1) to obtain 180 mg (yield: 74%) of the desired compound as an oil.

NMR spectrum (60 MHz, CDCl$_3$) δ ppm: 1.19 (3H, d, J=7 Hz), 1.90 (3H, d, J=1.5 Hz), 3.34 (1H, q, J=7 Hz), 3.0–3.9 (3H, m), 4.1–4.6 (2H, m), 4.80 (1H, d, J=14 Hz), 4.94 (1H, s), 5.02 (1H, d, J=1 Hz), 5.05 (1H, d, J=14 Hz), 6.4–7.0 (3H, m), 7.1–7.6 (1H, m), 7.40 (2H, d, J=9 Hz), 7.62 (2H, d, J=9 Hz), 7.80 (2H, 6)

EXAMPLE 2

(2R,3R)-2-(2,4-Difluorophenyl)-3-[[trans-2-[(E)-2-[4-(trifluoromethyl)phenyl]vinyl]-1,3-dioxan-5-yl]thio]-1-(1H-1,2,4-triazol-1-yl)-2-butanol

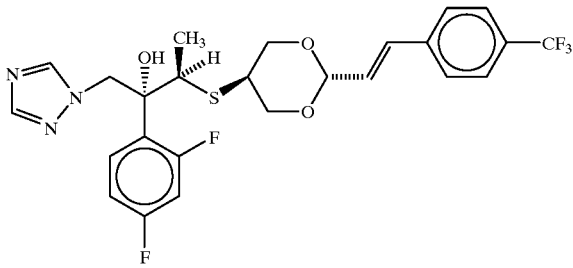

Reaction and treatment were carried out in the same manner as in Example 1 using (2R,3S)-2-(2,4-difluorophenyl)-3-methyl-2-[(1H-1,2,4-triazol-1-yl)methyl]oxirane and trans-5-(acetylthio)-2-[(E)-2-[4-(trifluoromethyl)phenyl]vinyl]-1,3-dioxane to obtain the desired compound having a melting point of 73 to 75° C. in a yield of 70%.

Specific rotation $[\alpha]_D^{25}$ −73.80 (c=1.00, CHCl$_3$)

NMR spectrum (270 MHz, CDCl$_3$) δ ppm: 1.19 (3H, d, J=7.3 Hz), 3.34 (1H, q, J=7.3 Hz), 3.43 (H, tt, j=11.2, 4.6 Hz), 3.65 (1H, t, J=11.2 Hz), 3.67 (1H, t, J=11.2 Hz), 4.33 (1H, ddd, J=11.2, 4.6, 2.0 Hz), 4.46 (1H, ddd, J=11.2, 4.6, 2.0 Hz), 4.82 (1H, d, J=13.8 Hz), 5.03 (1H, d, J=13.8 Hz), 5.04 (1H, br s), 5.14 (1H, d, J=4.6 Hz), 6.25 (1H, dd, J=15.8, 4.6 Hz), 6.7–7.8 (2H, m), 6.83 (1H, d, J=15.8 Hz), 7.3–7.45 (1H, m), 7.49 (2H, d, J=8.6 Hz), 7.58 (2H, d, J=8.6 Hz), 7.79 (2H, s).

EXAMPLE 3

(2R,3R)-3-[[Trans-4-[(E)-2-(4-chlorophenyl)vinyl]cyclohexyl]thio]-2-(2,4-difluorophenyl)-1-(1H-1,2,4-triazol-1-yl)-2-butanol

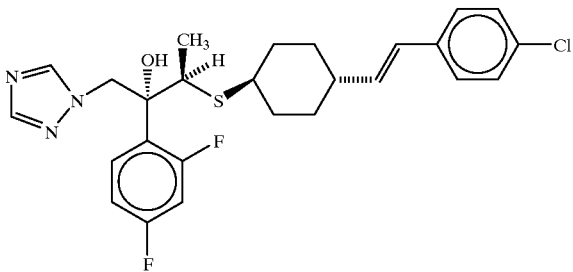

Reaction and treatment were carried out in the same manner as in Example 1 using (2R,3S)-2-(2,4-difluorophenyl)-3-methyl-2-[(1H-1,2,4-triazol-1-yl)methyl]oxirane and trans-1-(acetylthio)-4-[(E)-2-(4-chlorophenyl)vinyl]cyclohexane to obtain the desired compound having a melting point of 64 to 66° C. in a yield of 31%.

Specific rotation $[\alpha]_D^{25}$ −84.10 (c=2.69, CHCl$_3$)

NMR spectrum (270 MHz, CDCl$_3$) δ ppm: 1.16 (3H, d, J=7.3 Hz), 1.2–1.6 (4H, m), 1.9–2.0 (2H, m), 2.1–2.25 (3H, m), 2.70 (1H, tt, J=11.2, 4.0 Hz), 3.36 (1H, q, J=7.3 Hz), 4.60 (1H, s), 4.83 (11, d, J=13.9 Hz), 5.10 (1H, d, J=13.9 Hz), 6.11 (1H, dd, J=15.8, 7.3 Hz), 6.32 (1H, d, J=15.8 Hz), 6.74 (2H, t-like, J=9 Hz), 7.26 (4H, s), 7.37 (1H, td, J=8.6, 6.5 z), 7.76 (1H, s), 7.83 (1H, s).

EXAMPLE 4

(2R,3R)-3-[[Trans-2-[(E)-2-(4-chlorophenyl)vinyl]-1,3-dioxan-5-yl]thio]-2-(2,4-difluorophenyl)-1-(1H-1,2,4-triazol-1-yl)-2-butanol

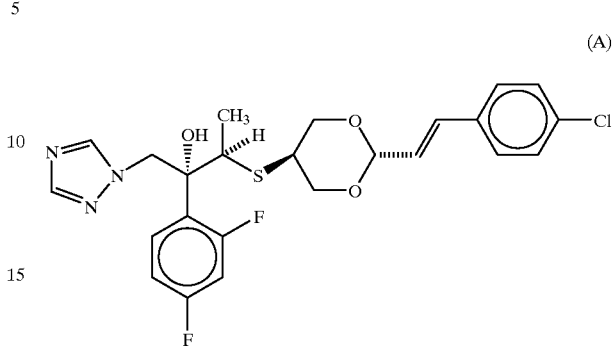

(A)

In 14 ml of methylene chloride were dissolved 294 mg (0.82 mmol) of (2R,3R)-2-(2,4-difluorophenyl)-3-[(1,3-dihydroxy-2-propyl)thio]-1-(1H-1,2,4-triazol-1-yl)-2-butanol as described in Reference example 2 and 191 mg (1.15 mmol) of trans-4-chlorocinnamaldehyde [Bull. Chem. Soc. Japan 52 555 (1979)], and 233 mg (1.23 mmol) of p-toluenesulfonic acid monohydrate and 1.5 g of molecular sieves 4A were added thereto, followed by stirring of the resulting mixture for 1 hour and 15 minutes. An aqueous sodium hydrogencarbonate solution was added to the reaction mixture and the mixture was stirred for 10 minutes, followed by removal of the molecular sieves by filtration. The organic layers were collected and dried to distil off the solvent under reduced pressure. The thus obtained oil was subjected to column chromatography using 15 g of silica gel and eluted with a mixed solvent hexane-ethyl acetate (3:2) to obtain 280 mg (yield: 67%) of the desired title compound, trans isomer (A) as an oil. Further, the oil was eluted with a mixed solvent of hexane-ethyl acetate (1:1) to obtain 35 mg (yield: 8%) of the cis isomer (B) as an oil.

Specific rotation (A) $[\alpha]_D^{25}$ −68° (c=1.22, CHCl$_3$)

Specific rotation (B) $[\alpha]_D^{25}$ −80° (c=1.30, CHCl3)

NMR spectrum (270 MHz, CDCl$_3$) δ ppm: (A), 1.19 (3H, d, J=7.3 Hz), 3.34 (1H, q, J=7.3 Hz), 3.41 (1H, tt, J=11.2, 4.6 Hz), 3.64 (1H, t, J=11.2 Hz), 3.66 (1H, t, J=11.2 Hz), 4.32 (1H, ddd, J=11.2, 4.6, 2.6 Hz), 4.44 (1H, ddd, J=11.2, 4.6, 2.6 Hz), 4.82 (1H, d, J=13.9 Hz), 5.01 (1H, s), 5.04 (1H, d, J=13.9 Hz), 5.11 (1H, d, J=4.6 Hz), 6.15 (1H, dd, J=15.8, 4.6 Hz), 6.7–6.8 (2H, m), 6.76 (1H, d, J=15.8 Hz), 7.25–7.45 (5H, m), 7.78 (2H, s); (B), 1.21 (3H, d, J=7.3 Hz), 3.11 (1H, s-like), 3.50 (1H, q, J=7.3 Hz), 4.2–4.4 (4H, m), 4.88 (1H, J=14.5 Hz), 4.93 (1H, s), 5.16 (1H, d, J=14.5 Hz), 5.23 (1H, d, J=4.6 Hz), 6.21 (1H, dd, J=16.5, 4.6 Hz), 6.65–6.8 (2H, m), 6.76 (1H, d, J=16.5 Hz), 7.25–7.45 (5H, m), 7.77 (1H, s), 7.80 (1H, s).

In ethyl acetate was dissolved 54 mg of (A), and 19 mg of oxalic acid was added to the solution, followed by addition of hexane to the resulting mixture. The precipitated cystal was collected by filtration to obtain 65 mg of the oxalic acid salt having a melting point of 89 to 92° C. The oxalate of (B) having a melting point of 94 to 98° C. was obtained analogously.

EXAMPLE 5

(2R,3R)-2-(2,4-Difluorophenyl)-3-[[trans-2-[(E)-2-(3-pyridyl)vinyl]-1,3-dioxan-5-yl]thio]-1-(1H-1,2,4-triazol-1-yl)-2-butanol

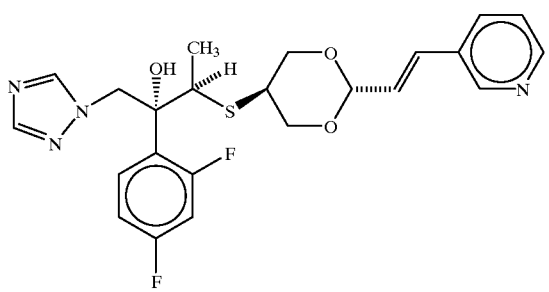

In 5 ml of methylene chloride were dissolved 120 mg (0.33 mmol) of (2R,3R)-2-(2,4-difluorophenyl)-3-[(1,3-dihydroxy-2-propyl)thio]-1-(1H-1,2,4-triazol-1-yl)-2-butanol and 60 mg (0.45 mmol) of trans-p-(3-pyridyl) acrolein [J. Med. Chem. 18 839 (1975)], 190 mg (1.00 mmol) of p-toluenesulfonic acid monohydrate and 1.2 g of molecular sieves 4A were added to the solution, followed by stirring of the resulting mixture for 1 hour and 15 minutes. An aqueous sodium hydrogencarbonate solution was added to the reaction mixture and the mixture was stirred for 10 minutes, followed by removal of the molecular sieves by filtration and extraction with chloroform. An oil obtained by evaporation of the solvent after drying was subjected to column chromatography using 15 g of silica gel and eluted with a mixed solvent of hexane-ethyl acetate (1:4 to 1:5) to obtain 82 mg (yield: 52%) of the title compound, trans isomer (A) as an oil. Further, the oil was eluted with ethyl acetate-5% methanol-ethyl acetate to obtain 28 mg (yield: 15%) of the cis isomer (B) having a melting point of 118 to 125° C. as a solid.

NMR spectrum (270 MHz, CDCl$_3$) δ ppm: (A), 1.20 (3H, d, J=7.3 Hz), 3.34 (1H, q, J=7.3 Hz), 3.43 (1H, tt, J=11.2, 4.6 Hz), 3.65 (1H, t, J=11.2 Hz), 3.68 (1H, t, J=11.2 Hz), 4.33 (1H, m), 4.46 (1H, m), 4.83 (1H, d, J=13.9 Hz), 5.04 (1H, s), 5.04 (1H, d, J=13.9 Hz), 5.14 (1H, d, J=4.0 Hz), 6.25 (1H, dd, J=16.5, 4.0 Hz), 6.7–6.8 (2H, m), 6.81 (1H, d, J=16.5 Hz), 7.29 (1H, dd, J=7.9, 4.6 Hz), 7.3–7.45 (1H, m), 7.73 (1H, dt, J=7.9, 1 Hz), 8.51 (1H, dd, J=4.6, 1 Hz), 8.62 (1H, d, J=1 Hz); (B), 1.22 (3H, d, J=7.3 Hz), 3.13 (1H, br s), 3.50 (1H, q, J=7.3 Hz), 4.2–4.4 (4H, m), 4.88 (1H, d, J=13.9 Hz), 4.94 (1H, s), 5.17 (1H, d, J=13.9 Hz), 5.26 (1H, d, J=4.6 Hz), 6.31 (1H, dd, J=16.5, 4.6 Hz), 6.65–6.8 (2H, m), 6.81 (1H, d, J=16.5 Hz), 7.26 (1H, dd, J=7.9, 4.6 Hz), 7.74 (1H, td, J=7.2, 6.6 Hz), 7.74 (1H, br d, J=7.9 Hz), 7.77 (1H, s), 7.80 (1H, s), 8.50 (1H, br d, J=4.6 Hz), 8.63 (1H, br s)

EXAMPLE 6
(2R,3R)-2-(2,4-Difluorophenyl)-3-[[trans-2-[(E)-2-[4-(trifluoromethyl)phenyl]vinyl]-1,3-dioxan-5-yl]thio]-1-(1H-1,2,4-triazol-1-yl)-2-butanol

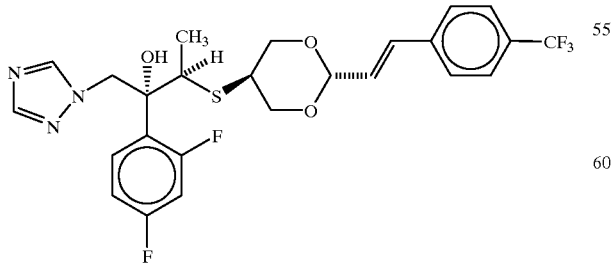

Reaction and treatment were carried out in the same manner as in Example 4 using (2R,3R)-2-(2,4-difluorophenyl)-3-[(1,3-dihydroxy-2-propyl)thio]-1-(1H-1,2,4-triazol-1-yl)-2-butanol and trans-4-(trifluoromethyl)cinnamaldehyde as described in Reference example 22 to obtain the desired compound as a major product (yield: 62%). Physical data and spectral data coincided with those of the compound described in Example 2.

EXAMPLE 7
(2R,3R)-2-(2,4-Difluorophenyl)-3-[[trans-2-[(E)-2-(4-fluorophenyl)vinyl]-1,3-dioxan-5-yl]thio]-1-(1H-1,2,4-triazol-1-yl)-2-butanol

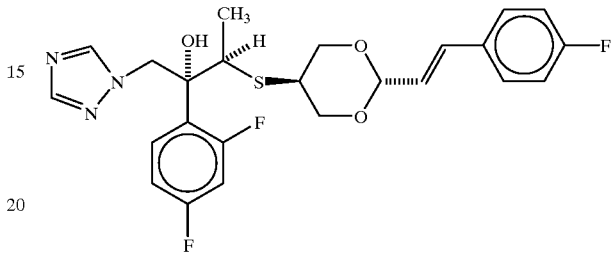

Reaction and treatment were carried out in the same manner as in Example 4 using (2R,3R)-2-(2,4-difluorophenyl)-3-[(1,3-dihydroxy-2-propyl)thio]-1-(1H-1,2,4-triazol-1-yl)-2-butanol and trans-4-fluorocinnamaldehyde [Arch. Pharm. 316 574 (1983)] to obtain the title compound, a major product as an oil in a yield of 66%.

NMR spectrum (60 MHz, CDCl$_3$) δ ppm: 1.20 (3H, d, J=7 Hz), 3.1–3.9 (4H, m), 4.1–4.6 (2H, m), 4.78 (1H, d, J=14 Hz), 4.99 (1H, d, J=1.5 Hz), 5.06 (1H, d, J=14 Hz), 5.09 (1H, d, J=4 Hz), 6.07 (1H, dd, J=16.4 Hz), 6.79 (1H, d, J=16 Hz), 6.5–7.6 (7H, m), 7.78 (2H, s).

This compound was mixed with 1 equivalent of oxalic acid in a mixed solvent of ethyl acetate-hexane to obtain an oxalic acid salt crystal having a melting point of 132 to 135° C.

EXAMPLE 8
(2R,3R)-2-(2,4-Difluorophenyl)-3-[[trans-2-[(E)-2-[2-fluoro-(4-trifluoromethyl)phenyl]vinyl]-1,3-dioxan-5-yl]thio]-1-(1H-1,2,4-triazol-1-yl)-2-butanol

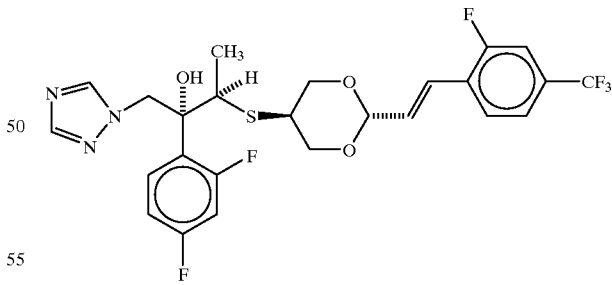

Reaction and treatment were carried out in the same manner as in Example 4 using (2R,3R)-2-(2,4-difluorophenyl)-3-[(1,3-dihydroxy-2-propyl)thio]-1-(1H-1,2,4-triazol-5-yl)-2-butanol and trans-2-fluoro-4-(trifluoromethyl)cinnamaldehyde to obtain the title compound, a major product as an oil in a yield of 66%.

Specific rotation $[\alpha]_D^{25}$ −72° (c=0.63, CHCl$_3$)

NMR spectrum (270 MHz, CDCl$_3$) δ ppm: 1.20 (3H, d, J=7.0 Hz), 3.34 (1H, q, J=7.0 Hz), 3.43 (1H, tt, J=11.3, 4.6 Hz), 3.65 (1H, t, J=11.3 Hz), 3.68 (1H, t, J=11.3 Hz), 4.34

(1H, m), 4.46 (1H, m), 4.83 (1H, d, J=14.0 Hz), 5.04 (d, J=14.0 Hz), 5.04 (1H, d, J=1.1 Hz), 5.15 (1H, d, J=4.2 Hz), 6.36 (1H, dd, J=16.3, 4.2 Hz), 6.7–6.8 (2H, m), 6.97 (1H, d, J=16.0 Hz), 7.3–7.45 (3H, m), 7.58 (1H, t, J=7.6 Hz), 7.79 (2H,

EXAMPLE 9
(2R,3R)-2-(2,4-Difluorophenyl)-3-[[trans-2-[(E)-2-[4-(methylsulfonyl)phenyl]vinyl]-1,3-dioxan-5-yl]thio]-1-(1H-1,2,4-triazol-1-yl)-2-butanol

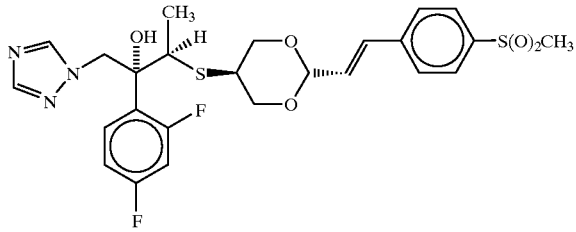

Reaction and treatment were carried out in the same manner as in Example 4 using (2R,3R)-2-(2,4-difluorophenyl)-3-[(1,3-dihydroxy-2-propyl)thio]-1-(1H-1,2,4-triazol-1-yl)-2-butanol and trans-4-(methylsulfonyl)cinnamaldehyde to obtain the title compound, a major product as an oil in a yield of 58%.

NMR spectrum (60 MHz, CDCl$_3$+D$_2$O) 3 ppm: 1.20 (3H, d, J=7 Hz), 3.00 (3H, 5), 3.33 (1H, q, J=7 Hz), 3.5–4.0 (3H, m), 4.2–4.8 (2H, m), 4.80 (1H, d, J=14 Hz), 5.08 (1H, d, J=14 Hz), 5.15 (1H, d, J=4 Hz), 6.30 (1H, dd, J=17, 4 Hz), 6.90 (1H, d, J=17 Hz), 6.55–7.0 (2H, m), 7.2–7.6 (1H, m), 7.58 (2H, d, J=8 Hz), 7.80 (2H, s), 7.94 (2H, d, J=8 Hz).

EXAMPLE 10
(2R,3R)-2-(2,4-Difluorophenyl)-3-[[trans-2-[(E)-2-(4-nitrophenyl)vinyl]-1,3-dioxan-5-yl]thio]-1-(1H-1,2,4-triazol-1-yl)-2-butanol

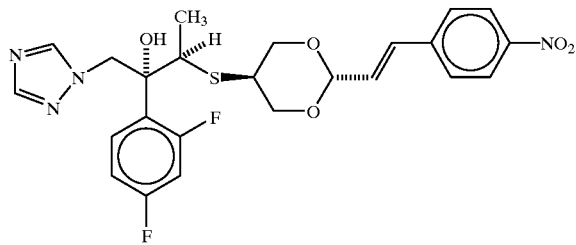

Reaction and treatment were carried out in the same manner as in Example 4 using (2R,3R)-2-(2,4-difluorophenyl)-3-[(1,3-dihydroxy-2-propyl)thio]-1-(1H-1,2,4-triazol-5-yl)-2-butarol and trans-4-nitrocinnamaldehyde to obtain the title compound, a major product as an oil in a yield of 40%.

Specific rotation $[\alpha]_D^{25}$ –64.10 (c=2.43, CHCl$_3$)

NMR spectrum (270 MHz, CDCl$_3$) δ ppm: 1.19 (3H, d, J=7.3 Hz), 3.35 (1H, q, J=7.3 Hz), 3.44 (1H, tt, J=11.2, 4.6 Hz), 3.66 (1H, t, J=11.2 Hz), 3.68 (1H, t, J=11.2 Hz), 4.34 (1H, m), 4.46 (1H, rn), 4.83 (1H, d, J=13.9 Hz), 5.04 (1H, a, J=13.9 Hz), 5.04 (1H, s), 5.16 (1H, d, J=4.0 Hz), 6.32 (1H, dd, J=16.5, 4.0 Hz), 6.87 (1H, d, J=16.5 Hz), 7.36 (1H, m), 7.53 (2H, d, J=8.6 Hz), 7.79 (1H, s), 7.80 (1H, s), 8.19 (2H, d, J=8.6 Hz).

This compound was mixed with 1 equivalent of oxalic acid in a mixed solvent of ethyl acetate-hexane to obtain an oxalic acid salt crystal having a melting point of 103 to 105° C.

EXAMPLE 11
(2R,3R)-2-(2,4-Difluorophenyl)-1-(1H-1,2,4-triazol-1-yl)-3-[[trans-2-[(E)-2-[4-(trifluoromethoxy)phenyl]vinyl]-1,3-dioxan-5-yl]thio]-2-butanol

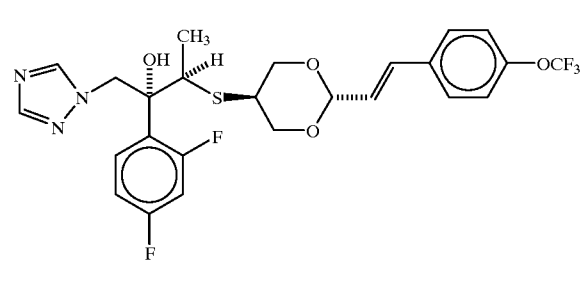

Reaction and treatment were carried out in the same manner as in Example 4 using (2R,3R)-2-(2,4-difluorophenyl)-3-[(1,3-dihydroxy-2-propyl)thio]-1-(1H-1,2,4-triazol-5-yl)-2-butanol and trans-4-(trifluoromethoxy)cinnamaldehyde as described in Reference example 33 to obtain the title compound, a major product as an oil in a yield of 43%.

Specific rotation $[\alpha]_D^{25}$ –770 (c=0.52, CHCl$_3$)

NMR spectrum (270 MHz, CDCl$_3$) δ ppm: 1.20 (3H, d, J=7.3 Hz), 3.34 (1H, q, J=2.3 Hz), 3.42 (1H, tt, J=11.2, 4.6 Hz), 3.65 (1H, t, J=11.2 Hz), 3.67 (1H, t, J=11.2 Hz), 4.32 (1H, ddd, J=11.2, 4.6, 2.0 Hz), 4.45 (1H, ddd, J=11.2, 4.6, 2.0 Hz), 4.83 (1H, d, J=14.5 Hz), 5.01 (1H, s), 5.03 (1H, d, J=14.5 Hz), 5.12 (1H, d, J=4.0 Hz), 6.15 (1H, dd, J=16.5, 4.0 Hz), 6.7–6.8 (2H, m), 6.79 (1H, d, J=16.5 Hz), 7.17 (2H, d, J=8.6 Hz), 7.3–7.45 (1H, m), 7.42 (2H, d, J=8.6 Hz), 7.79 (2H, s)

EXAMPLE 12
(2R,3R)-3-[[Trans-2-[(E)-2-(4-cyanophenyl)vinyl]-1,3-dioxan-5-yl]thio]-2-(2,4-difluorophenyl)-1-(1H-1,2,4-triazol-1-yl)-2-butanol

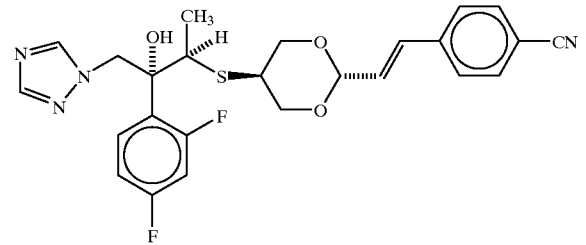

Reaction and treatment were carried out in the same manner as in Example 4 using (2R,3R)-2-(2,4-difluorophenyl)-3-[(1,3-dihydroxy-2-propyl)thio]-1-(1H-1,2,4-triazol-5-yl)-2-butanol and trans-4-cyanocinnamaldehyde [Mol. Cryst. Liq. Cryst. 123 257 (1985)] to obtain the title compound, a major product as an oil in a yield of 66%.

Specific rotation $[\alpha]_D^{25}$ –78° (c=0.52, CHCl$_3$)

NMR spectrum (270 MHz, CDCl$_3$) δ ppm: 1.20 (3H, d, J=7.0 Hz), 3.34 (1H, br q, J=7.0 Hz), 3.43 (1H, tt, J=11.3, 4.8 Hz), 3.65 (1H, t, J=11.3 Hz), 3.67 (1H, t, J=11.3 Hz), 4.33 (1H, m), 4.46 (1H, m), 4.83 (1H, d, J=14.2 Hz), 5.03 (1H, d, J=1.2 Hz), 5.04 (1H, d, J=14.2 Hz), 5.14 (1H, d, J=4.1 Hz), 6.28 (1H, dd, J=16.1, 4.1 Hz), 6.7–6.8 (2H, m), 6.82 (1H, d, J=16.1 Hz), 7.36 (1H, m), 7.49 (2H, d, J=8.3 Hz), 7.62 (2H, d, J=8.3 Hz), 7.79 (2H, s).

This compound was mixed with 1 equivalent of oxalic acid in a mixed solvent of ethyl acetate-hexane to obtain an oxalic acid salt crystal having a melting point of 164 to 165° C.

EXAMPLE 13

(2R,3R)-2-(2,4-Difluorophenyl)-3-[[trans-2-[(E)-2-methyl-2-[4-(trifluoromethyl)phenyl]vinyl]-1,3-dioxan-5-yl]thio]-1-(1H-1,2,4-triazol-1-yl)-2-butanol

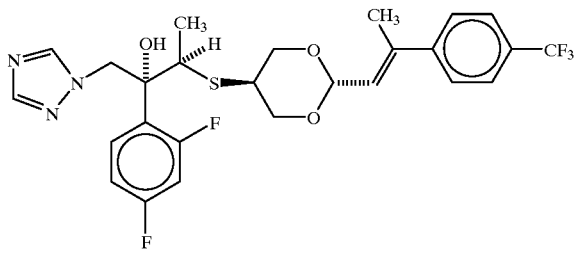

Reaction and treatment were carried out in the same manner as in Example 4 using (2R,3R)-2-(2,4-difluorophenyl)-3-[((,3-dihydroxy-2-propyl)thio]-1-(1H-1,2,4-triazol-1-yl)-2-butanol and trans-p-methyl-4-(trifluoromethyl)cinnamaldehyde to obtain the desired title compound, a major product as an oil in a yield of 73%.

NMR spectrum (270 MHz, CCl$_3$) δ ppm: 1.20 (3H, d, J=7.1 Hz), 2.16 (3H, s), 3.36 (1H, q, J=7.1 Hz), 3.41 (1H, tt, J=11.3, 4.6 Hz), 3.66 (1H, t, J=11.3 Hz), 3.68 (1H, t, J=11.3 Hz), 4.32 (1H, m), 4.44 (1H, m), 4.83 (1H, d, J=13.9 Hz), 5.03 (1H, s), 5.04 (1H, d, J=13.9 Hz), 5.33 (1H, d, J=6.0 Hz), 5.83 (1H, br d, J=6.0 Hz), 6.7–6.8 (2H, m), 7.3–7.45 (1H, m), 7.51 (2H, d, J=8.3 Hz), 7.59 (2H, d, J=8.3 Hz), 7.79 (2H, s).

EXAMPLE 14

(2R,3R)-3-[[Trans-2-[(E)-2-(5-chloro-2-thienyl)vinyl]-1,3-dioxan-5-yl]thio]-2-(2,4-difluorophenyl)-1-(1H-1,2,4-triazol-1-yl)-2-butanol

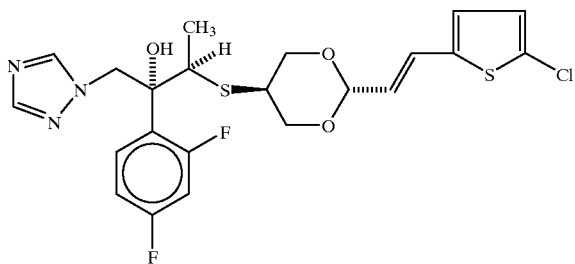

Reaction and treatment were carried out in the same manner as in Example 4 using (2R,3R)-2-(2,4-difluorophenyl)-3-[(1,3-dihydroxy-2-propyl)thio]-1-(1H-1,2,4-triazol-5-yl)-2-butanol and trans-P-(5-chloro-2-thienyl) acrolein [Chem. Abst. 51 1284h (1941)] to obtain the title compound as an oil in a yield of 50%.

Specific rotation $[\alpha]_D^{25}$ –75.7° (c=0.56, CHCl$_3$)

NMR spectrum (270 MHz, CDCl$_3$) δ ppm: 1.19 (3H, d, J=7.3 Hz), 3.33 (1H, q, J=7.3 Hz), 3.40 (1H, tt, J=11.2, 4.6 Hz), 3.62 (1H, t, J=11.2 Hz), 3.64 (1H, t, J=11.2 Hz), 4.36 (1H, m), 4.42 (1H, m), 4.82 (1H, d, J=13.8 Hz), 5.02 (1H, br s), 5.03 (1H, d, J=13.8 Hz), 5.06 (1H, d, J=4.6 Hz), 5.88 (1H, dd, J=15.8, 4.6 Hz), 6.7–6.85 (3H, m), 6.78 (2H, s), 7.36 (1H, m), 7.87 (2H, s).

This compound was mixed with 1 equivalent of oxalic acid in a mixed solvent of ethyl acetate-hexane to obtain an oxalic acid salt crystal having a melting point of 53 to 57° C.

EXAMPLE 15

(2R,3R)-2-(2,4-Difluorophenyl)-1-(1H-1,2,4-triazol-1-yl)-3-[[trans-2-[(1E,3E)-4-[4-(trifluoromethyl)phenyl]-1,3-butadien-1-yl]-1,3-dioxan-5-yl]thio]-2-butanol

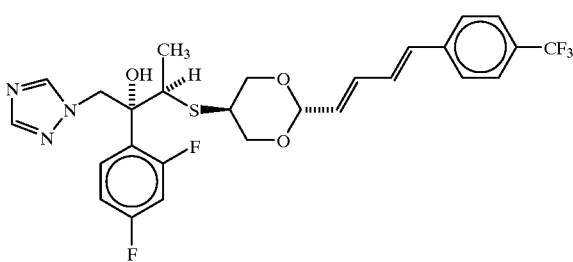

Reaction and treatment were carried out in the same manner as in Example 4 using (2R,3R)-2-(2,4-difluorophenyl)-3-[(1,3-dihydroxy-2-propyl)thio]-1-(1H-1,2,4-triazol-5-yl)-2-butanol and (2E,4E)-5-[4-(trifluoromethyl)phenyl]-2,4-pentadienal as described in Reference example 25 to obtain the title compound, a major product as an oil in a yield of 67%.

Specific rotation $[\alpha]_D^{25}$ –69.80 (c=1.00, CHCl$_3$)

NMR spectrum (270 MHz, CDCl$_3$) δ ppm: 1.19 (3H, d, J=7.3 Hz), 3.33 (1H, q, J=7.3 Hz), 3.40 (1H, tt, J=11.2, 4.6 Hz), 3.62 (1H, t, J=11.2 Hz), 3.64 (1H, t, J=11.2 Hz), 4.30 (1H, m), 4.42 (1H, m), 4.82 (1H, d, J=13.9 Hz), 5.01 (1H, s), 5.03 (1H, d, J=13.9 Hz), 5.06 (1H, d, J=4.6 Hz), 5.84 (1H, dd, J=15.2, 4.6 Hz), 6.60 (1H, dd, J=15.2, 10.6 Hz), 6.73 (1H, d, J=15.8 Hz), 6.7–6.8 (2H, m), 6.85 (1H, dd, J=15.8, 10.6 Hz), 7.3–7.45 (1H, m), 7.49 (2H, d, J=8.6 Hz), 7.56 (2H, d, J=8.6 Hz), 7.78 (2H, s).

EXAMPLE 16

(2R,3R)-2-(2,4-Difluorophenyl)-3-[[trans-2-[(1E,3E)-4-[4-(2,2,3,3-tetrafluoropropoxy)phenyl]-1,3-butadien-1-yl]-1,3-dioxan-5-yl]thio]-1-(1H-1,2,4-triazol-1-yl)-2-butanol

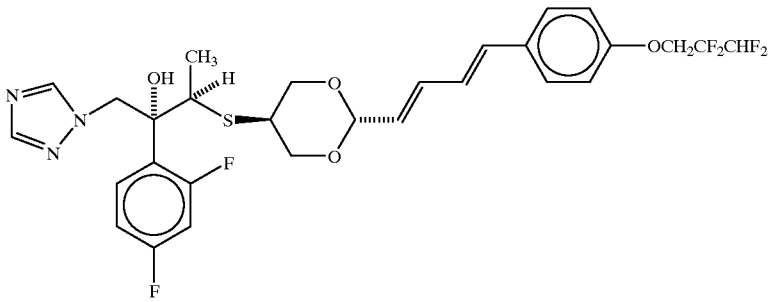

Reaction and treatment were carried out in the same manner as in Example 4 using (2R,3R)-2-(2,4-difluorophenyl)-3-[(1,3-dihydroxy-2-propyl)thio]-1-(1H-1,2,4-triazol-5-yl)-2-butanol and (2E,4E)-5-[4-(2,2,3,3-tetrafluoropropoxy)phenyl]-2,4-pentadienal as described in Reference example 32 to obtain the title compound having a melting point of 75 to 85° C. (crystallization from a mixed solvent of hexane-ether), a major product as a powder in a yield of 60%.

Specific rotation $[\alpha]_D^{25}$ −69(c=0.56, CHCl$_3$)

NMR spectrum (270 MHz, CDCl$_3$) δ ppm: 1.18 (3H, d, J=7.0 Hz), 3.33 (1H, q, J=7.0 Hz), 3.39 (1H, tt, J=11.3, 4.8 Hz), 3.62 (1H, t, J=11.3 Hz), 3.64 (1H, t, J=11.3 Hz), 4.30 (1H, m), 4.35 (2H, br t, J=11.8 Hz), 4.41 (1H, m), 4.82 (1H, d, J=14.1 Hz), 4.99 (1H, d, J=1.6 Hz), 5.03 (1H, d, J=14.1 Hz), 5.04 (1H, d, J=4.6 Hz), 5.75 (1H, dd, J=15.7, 4.6 Hz), 6.06 (1H, tt, J=53.0, 5.1 Hz), 6.56 (1H, dd, J=15.7, 10.2 Hz), 6.57 (1, d, J=15.0 Hz), 6.68 (1H, dd, J=15.0, 10.2 Hz), 6.7–6.8 (2H, m), 6.88 (2H, d, J=8.7 Hz), 7.3–7.4 (1H, m), 7.37 (2H, d, J=8.7 Hz), 7.79 (2H, s).

EXAMPLE 17

(2R,3R)-3-[[Trans-2-[(1E,3E)-4-(6-chloro-3-pyridyl)-1,3-butadien-1-yl]-1,3-dioxan-5-yl]thio]-2-(2,4-difluorophenyl)-1-(1H-1,2,4-triazol-1-yl)-2-butanol

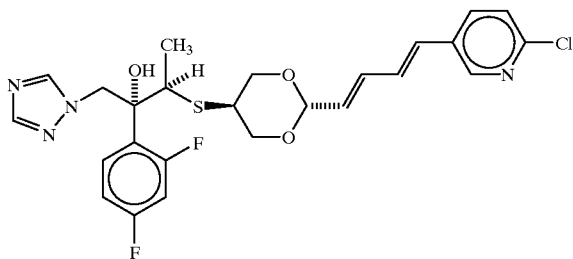

Reaction and treatment were carried out in the same manner as in Example 4 using (2R,3R)-2-(2,4-difluorophenyl)-3-[(1,3-dihydroxy-2-propyl)thio]-1-(1H-1,2,4-triazol-5-yl)-2-butanol and (2E,4E)-5-(6-chloro-3-pyridyl)-2,4-pentadienal as described in Reference example 38 to obtain the title compound having a melting point of 88 to 90° C., a major product as a crystalline solid in a yield of 69%.

Specific rotation $[\alpha]_D^{25}$ −74° (c=0.59, CHCl$_3$)

NMR spectrum (270 MHz, CDCl$_3$) δ ppm: 1.19 (3H, d, J=7.1 Hz), 3.33 (1H, q, J=7.1 Hz), 3.40 (1H, tt, J=11.3, 4.7 Hz), 3.62 (1H, t, J=11.3 Hz), 3.64 (1H, t, J=11.3 Hz), 4.30 (1H, m), 4.42 (1H, m), 4.82 (1H, d, J=14.3 Hz), 5.00 (1H, s), 5.03 (1H, d, J=14.3 Hz), 5.05 (1H, d, J=4.2 Hz), 5.84 (1H, dd, J=15.1, 4.2 Hz), 6.56 (1H, d, J=15.5 Hz), 6.58 (1H, dd, J=15.1, 10.5 Hz), 6.7–6.8 (2H, m), 6.80 (1H, dd, J=15.5, 10.5 Hz), 7.28 (1H, d, J=8.3 Hz), 7.3–7.4 (1H, m), 7.70 (1H, dd, J=8.3, 2.5 Hz), 7.79 (2H, s), 8.37 (1H, d, J=2.5 Hz).

EXAMPLE 18

(2R,3R)-2-(2,4-Difluorophenyl)-3-[[trans-2-[(1E,3Z)-4-(4-chlorophenyl)-5,5,5-trifluoro-1,3-pentadien-1-yl]-1,3-dioxan-5-yl]thio]-1-(1H-1,2,4-triazol-1-yl)-2-butanol

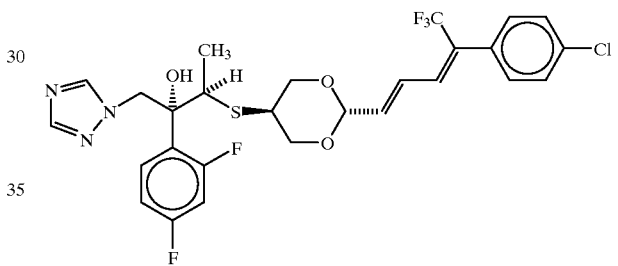

Reaction and treatment were carried out in the same manner as in Example 4 using (2R,3R)-2-(2,4-difluorophenyl)-3-[(1,3-dihydroxy-2-propyl)thio]-1-(1H-1,2,4-triazol-5-yl)-2-butanol and (2E,4Z)-5-(4-chlorophenyl)-6,6,6-trifluoro-2,4-hexadienal as described in Reference example 52 to obtain the title compound, a major product as an oil in a yield of 31%.

Specific rotation $[\alpha]_D^{25}$ −59.40 (c=0.90, CHCl$_3$)

NMR spectrum (270 MHz, CDCl$_3$) δ ppm: 1.19 (3H, d, J=7.3 Hz), 3.33 (1H, br q, J=7.3 Hz), 3.40 (1H, tt, J=11.2, 4.6 Hz), 3.61 (1H, t, J=11.2 Hz), 3.64 (1H, t, J=11.2 Hz), 4.31 (1H, m), 4.43 (1H, m), 4.82 (1H, d, J=13.9 Hz), 5.02 (1H, s), 5.03 (1H, d, J=13.9 Hz), 5.09 (1H, d, J=4.6 Hz), 5.96 (1H, dd, J=15.2, 4.6 Hz), 6.50 (1H, d, J=11.9 Hz), 6.7–6.8 (2H, m), 6.9–7.1 (1H, m), 7.25–7.4 (5H, m), 7.79 (2H, s).

EXAMPLE 19

(2R,3R)-2-(2,4-Difluorophenyl)-3-[[trans-2-[(1E,3E)-2-methyl-4-[4-(trifluoromethyl)phenyl]-1,3-butadien-1-yl]-1,3-dioxan-5-yl]thio]-1-(1H-1,2,4-triazol-1-yl)-2-butanol

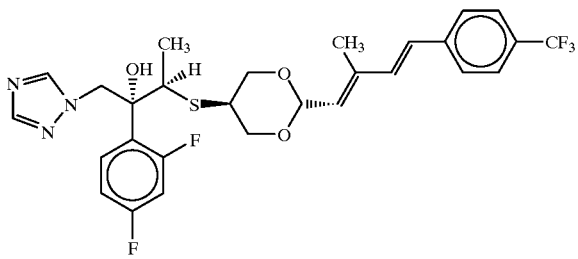

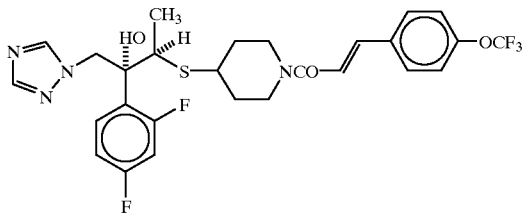

Reaction and treatment were carried out in the same manner as in Example 4 using (2R,3R)-2-(2,4-difluorophenyl)-3-[(,3-dihydroxy-2-propyl)thio]-1-(1H-1,2,4-triazol-5-yl)-2-butanol and (2E,4E)-3-methyl-5-[4-(trifluoromethyl)phenyl]-2,4-pentadienal as described in Reference example 10 to obtain the title compound, a major product as an oil in a yield of 70%.

Specific rotation $[\alpha]_D^{25}$ −68° (c=0.50, CHCl$_3$)

NMR spectrum (270 MHz, CDCl$_3$) δ ppm: 1.27 (3H, d, J=7.1 Hz)$_1$ 1.99 (3H, s), 3.34 (1H, q, J=7.1 Hz), 3.39 (1H, tt, J=11.3, 4.8 Hz), 3.64 (1H, t, J=11.3 Hz), 3.66 (1H, t, J=11.3 Hz), 4.30 (1H, m), 4.41 (1H, m), 4.83 (1H, d, J=14.1 Hz), 5.01 (1H, s), 5.04 (1H, d, J=14.1 Hz), 5.32 (1H, d, J=6.2 Hz), 5.66 (1H, d, J=6.2 Hz), 6.66 (1H, d, J=16.1 Hz), 6.7–6.8 (2H, m), 6.86 (1H, d, J=16.1 Hz), 7.3–7.4 (1H, m), 7.51 (2H, d, J=8.4 Hz), 7.57 (2H, d, J=8.4 Hz), 7.78 (2H, s).

EXAMPLE 20

(2R,3R)-2-(2,4-Difluorophenyl)-3-[[trans-2-[(1E,3E)-3-methyl-4-[4-(trifluoromethyl)phenyl]-1,3-butadien-1-yl]-1,3-dioxan-5-yl]thio]-1-(1H-1,2,4-triazol-1-yl)-2-butanol

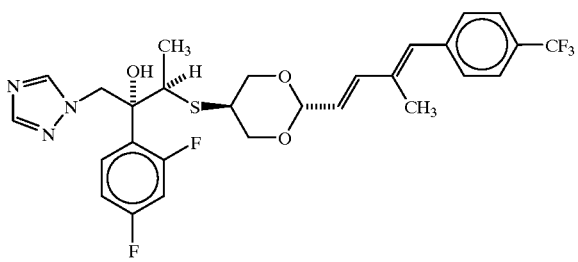

Reaction and treatment were carried out in the same manner as in Example 4 using (2R,3R)-2-(2,4-difluorophenyl)-3-[(1,3-dihydroxy-2-propyl)thio]-1-(1H-1,2,4-triazol-5-yl)-2-butanol and (2E,4E)-4-methyl-5-[4-(trifluoromethyl)phenyl3–2,4-pentadienal to obtain the title compound, a major product as an oil in a yield of 69%.

Specific rotation $[\alpha]_D^{25}$ −63.4° (c=1.07, CHCl$_3$)

NMR spectrum (270 MHz, CDCl$_3$) δ ppm: 1.19 (3H, d, J=7.0 Hz), 2.00 (3H, s), 3.33 (1H, q, J=7.0 Hz), 3.41 (1H, tt, J=11.2, 4.6 Hz), 3.64 (1H, t, J=11.2 Hz), 3.66 (1H, t, J=11.2 Hz), 4.31 (1H, m), 4.43 (1H, m), 4.83 (1H, d, J=14.2 Hz), 5.01 (1H, s), 5.04 (1H, d, J=14.2 Hz), 5.09 (1H, d, J=4.6 Hz), 5.81 (1H, dd, J=16.0, 4.6 Hz), 6.60 (1H, s), 6.63 (1H, d, J=16.0 Hz), 6.7–6.8 (2H, m), 7.3–7.4 (1H, m), 7.38 (2H, d, J=8.2 Hz), 7.59 (2H, d, J=8.2 Hz), 7.79 (2H, s).

EXAMPLE 21

(2R,3R)-2-(2,4-Difluorophenyl)-3-[[1-[(E)-4-(trifluoromethoxy)cinnamoyl]piperidin-4-yl]thio]-1-(1H-1,2,4-triazol-1-yl)-2-butanol

[Process A]

To a mixture of 150 mg (0.340 mmol) of (2R,3R)-(2,4-difluorophenyl)-3-(1H-1,2,4-triazol-1-yl)-3-[(piperidin-4-yl)thio]-2-butanol dihydrochloride as described in Reference example 14 and 3 ml of dichloromethane were added 142 μl (1.02 mmol) of triethylamine at 0C under nitrogen atmosphere and, after 5 minutes, 128 mg (0.510 mmol) of (E)-4-(trifluoromethoxy)cinnamoyl chloride. The mixture was stirred at the same temperature for 30 minutes and the solvent was distilled off, and then ethyl acetate was added to the thus obtained residue, followed by washing of the mixture with an aqueous NaCl solution. The solvent was distilled off and the residue was subjected to silica gel column chromatography, followed by elution with ethyl acetate to obtain 160 mg (yield: 81%) of the title compound as a colorless foam.

NMR spectrum (270 MHz, CDCl$_3$) δ ppm: 1.19 (3H, d, J=7.0 Hz), 1.6–1.8 (2H, m), 2.0–2.1 (2H, m), 3.0–3.2 (2H, m), 3.35 (1H, q, J=7.0 Hz), 3.2–3.4 (1H, m), 4.0–4.1 (1H, m), 4.2–4.3 (1H, m), 4.83 (1H, s), 4.83 (1H, d, J=14.0 Hz), 5.09 (1H, d, J=14.0 Hz), 6.7–6.8 (2H, m), 6.87 (1H, d, J=15.5 Hz), 7.22 (2H, d, J=8.5 Hz), 7.3–7.4 (1H, m), 7.55 (2H, d, J=8.5 Hz), 7.65 (1H, d, J=15.5 Hz), 7.78 (1H, s), 7.82 (1H, s).

IR spectrum $\upsilon_{max}^{KBr}$cm$^{-1}$: 3421, 1695, 1686, 1617, 1591.

Mass spectrum m/e: 582, 563, 522, 500, 427, 359, 299, 258, 215, 187, 144, 101, 82.

[Process B]

In 4 ml of dimethylformamide were dissolved 327 mg (0.875 mmol) of 4-(acetylthio)-1-[(E)-4-(trifluoromethoxy)cinnamoyl]piperidine as described in Reference example 16 and 200 mg (0.796 mmol) of (2R,3S)-2-(2,4-difluorophenyl)-3-methyl-2-[(H-1,2,4-triazol-1-yl)methyl]oxirane, and 129 μl (0.613 mmol) of a 28% sodium methoxide-methanol solution were added to the mixture under nitrogen atmosphere, followed by stirring of the resulting mixture at 50° C. for 3 hours. After cooling, ethyl acetate was added to the reaction mixture to dilute it and washed with water and then a saturated aqueous NaCl solution.

The oil obtained by evaporation of the solvent was subjected to silica gel column chromatography and eluted with ethyl acetate to obtain 275 mg (yield: 59%) as a colorless foam. The present compound was identified as the compound obtained according to the [Process A] by means of each spectrum of NMR, IR and MS.

EXAMPLE 22

(2R,3R)-2-(2,4-Difluorophenyl)-3-[[1-((E)-4-methylcinnamoyl)piperidin-4-yl]thio]-1-(1H-1,2,4-triazol-1-yl)-2-butanol

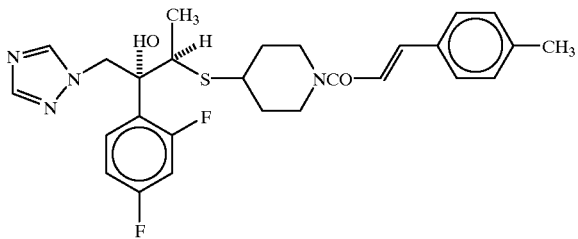

A colorless foam obtained from (E)-4-methylcinnamoyl chloride (Can. J. Chem. 45 1001 (1967)] according to [Process A] of Example 21.

NMR spectrum (270 MHz, CDCl$_3$) δ ppm: 1.19 (3H, d, J=7.0 Hz), 1.6–1.8 (2H, m), 2.0–2.2 (2H, m), 2.37 (3H, s), 3.0–3.2 (2H, m), 3.2–3.4 (1H, m), 3.35 (1H, q, J=7.0 Hz), 4.0–4.2 (1H, m), 4.4–4.6 (1H, m), 4.83 (1H, d, J=13.9 Hz), 4.84 (1H, s), 5.09 (1H, d, J=13.9 Hz), 6.7–6.8 (2H, m), 6.85 (1H, d, J=15.5 Hz), 7.18 (2H, d, J=8.3 Hz), 7.3–7.4 (1H, m), 7.43 (2H, d, J=8.3 Hz), 7.65 (1H, d, J=15.5 Hz), 7.77 (1H, s), 7.82 (1H, s).

IR spectrum $\upsilon_{max}^{KBr}$cm$^{-1}$: 3333, 1645, 1599.

Mass spectrum m/e: 512, 510, 452, 430, 425, 367, 357, 289, 229, 224, 188, 145, 117, 82.

EXAMPLE 23

(2R,3R)-2-(2,4-Difluorophenyl)-3-[[1-((E)-4-nitrocinnamoyl)piperidin-4-yl]thio]-1-(1H-1,2,4-triazol-1-yl)-2-butanol

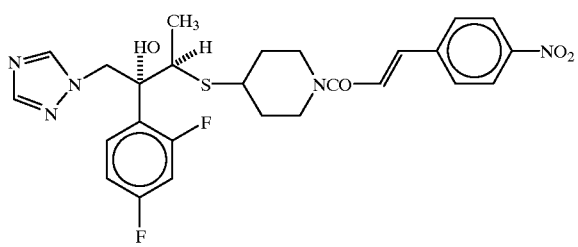

A slightly yellow foam obtained from (E)-4-nitrocinnamoyl chloride according to [Process A] of Example 21.

NMR spectrum (270 MHz, CDCl$_3$) δ ppm: 1.26 (3H, d, J=6.6 Hz), 1.6–1.9 (2H, m), 2.1–2.3 (2H, m), 3.1–3.3 (2I, m), 3.3–3.5 (1H, m), 3.42 (1H, q, J=6.6 Hz), 4.0–4.2 (1H, m), 4.4–4.6 (1H, m), 4.89 (1H, d, J=13.9 Hz), 4.92 (1H, s), 5.15 (1H, d, J=13.9 Hz), 6.7–6.9 (2H, m), 7.10 (1I, d, J=15.5 Hz), 7.4–7.5 (1H, m), 7.73 (2H, d, J=8.9 Hz), 7.75 (1H, d, J=15.5 Hz), 7.86 (2H, d, J=8.9 Hz), 8.29 (1H, s), 8.32 (1H, s).

IR spectrum $\upsilon_{max}^{KBr}$cm$^{-1}$: 3361, 1649, 1612, 1518, 1345.

Mass spectrum m/e: 544, 525, 513, 483, 461, 388, 365, 284, 260, 224, 219, 176, 144, 130, 82.

EXAMPLE 24

(2R,3R)-2-(2,4-Difluorophenyl)-1-(1H-1,2,4-triazol-1-yl)-3-[[1-[(2E,4E)-5-[4-(trifluoromethoxy)phenyl]-2,4-pentadienoyl]piperidin-4-yl]thio]-2-butanol

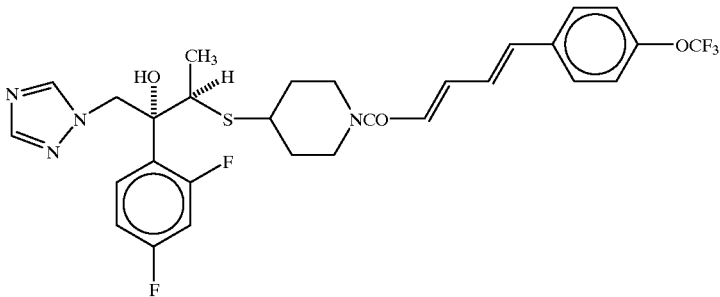

A colorless foam obtained from (2E,4E)-5-[4-(trifluoromethoxy)phenyl]-2,4-pentadienoyl chloride according to [Process A] of Example 21.

NMR spectrum (270 MHz, CDCl$_3$) δ ppm: 1.19 (3H, d, J=6.6 Hz), 1.5–1.8 (2H, m), 2.0–2.2 (2H, m), 3.0–3.3 (3H, m), 3.34 (1H, q, J=6.6 Hz), 3.9–4.1 (1H, m), 4.3–4.5 (1H, m), 4.83 (1H, d, J=13.9 Hz), 4.82 (1H, s), 5.08 (1H, d, J=13.9 Hz), 6.50 (1H, d, J=14.5 Hz), 6.7–6.8 (2H, m), 6.8–6.9 (2H, m), 7.20 (2H, d, J=8.9 Hz), 7.3–7.5 (2H, m), 7.47 (2H, d, J=8.9 Hz), 7.78 (1H, s), 7.82 (1H, s).

IR spectrum $\upsilon_{max}^{KBr}$cm$^{-1}$: 3395, 1639, 1616, 1596.

Mass spectrum m/e: 608, 589, 548, 526, 453, 433, 385, 325, 241, 224, 213, 144, 127, 82.

EXAMPLE 25

(2R,3R)-2-(2,4-Difluorophenyl)-1-(1H-1,2,4-triazol-1-yl)-3-[[1-[(E)-3-(pyridin-4-yl)-acryloyl]piperidin-4-yl]thio]-2-butanol

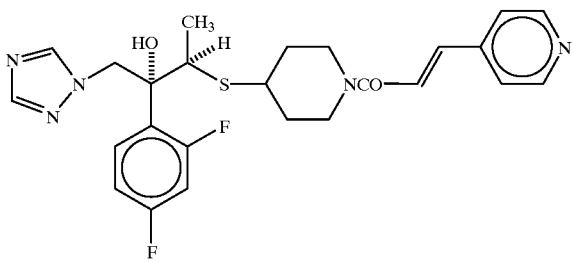

A colorless foam obtained from 4-acetylthio-1-[(E)-3-(pyridin-4-yl)-acryloyl]piperidine according to [Process B] of Example 21.

NMR spectrum (270 MHz, CDCl$_3$) δ ppm: 1.20 (3H, d, J=6.6 Hz), 1.6–1.8 (2H, m), 2.0–2.2 (2H, m), 3.0–3.2 (2H, m), 3.35 (1H, q, J=6.6 Hz), 3.2–3.4 (1H, m), 3.9–4.1 (1H, m), 4.3–4.5 (1H, m), 4.83 (1H, d, J=14.5 Hz), 4.86 (1H, s), 5.09 (1H, d, J=14.5 Hz), 6.7–6.8 (2H, m), 7.06 (1H, d, J=15.2 Hz), 7.3–7.4 (1H, m), 7.37 (2H, d, J=5.9 Hz), 7.57 (1H, d, J=15.2 Hz), 7.78 (1H, s), 7.81 (1H, s), 8.64 (2H, d, J=5.9 Hz).

IR spectrum $\upsilon_{max}^{KBr}$cm$^{-1}$: 3420, 1651, 1615, 1598.

Mass spectrum m/e: 499, 439, 417, 410, 365, 344, 307, 275, 247, 216, 144, 132, 104, 82.

EXAMPLE 26

(2R,3R)-2-(2,4-Difluorophenyl)-3-[[1-(E)-4-(trifluoromethoxy)cinnamoyl]azetidin-3-yl]thio]-1-(1H-1,2,4-triazol-1-yl)-2-butanol

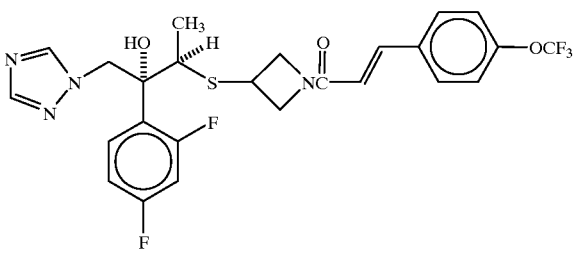

A slightly yellow foam obtained from (2R,3R)-2-(2,4-difluorophenyl)-1-(1H-1,2,4-triazol-1-yl)-3-[(azetidin-3-yl)thio]-2-butanol dihydrochloride according to [Process A] of Example 21.

NMR spectrum (270 MHz, CDCl$_3$) δ ppm: 1.17 (3H, d, J=7.1 Hz), 3.32 (1H, q, J=7.1 Hz), 4.0–4.3 (3H, m), 4.5–4.6 (1H, m), 4.6–4.7 (1H, m), 4.86 (1H, d, J=14.2 Hz), 5.05 (1H, d, J=14.2 Hz), 5.09 (1H, s), 6.43 (1H, d, J=15.7 Hz), 6.7–6.8 (2H, m), 7.22 (2H, d, J=8.2 Hz), 7.3–7.4 (1H, m), 7.56 (2H, d, J=8.2 Hz), 7.65 (1H, d, J=15.7 Hz), 7.79 (1H, s), 7.81 (1H, s).

IR spectrum $\upsilon_{max}^{KBr}$cm$^{-1}$: 3376, 1656.

Mass spectrum m/e: 554, 535, 472, 384, 331, 271, 224, 215, 187, 127, 87.

EXAMPLE 27

(2R,3R)-2-(2,4-Difluorophenyl)-3-[[trans-2-[(1E,3E)-4-(2,4-difluorophenyl)-1,3-butadien-1-yl]-1,3-dioxan-5-yl]thio]-1-(1–1,2,4-triazol-1-yl)-2-butanol

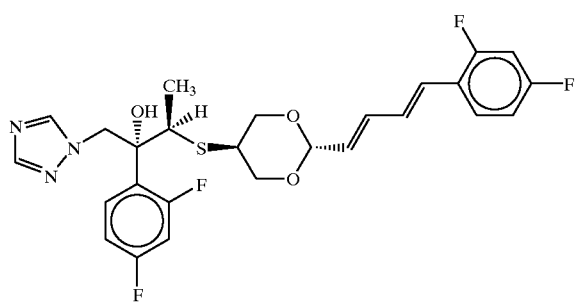

Reaction was carried out in the same manner as in Example 4 using (2R,3R)-2-(2,4-difluorophenyl)-3-[(1,3-dihydroxy-2-propyl)thio]-1-(1H-1,2,4-triazol-5-yl)-2-butanol and (2E,4E)-5-(2,4-difluorophenyl)-2,4-pentadienal to obtain the title compound, a major product as an oil in a yield of 61%.

Specific rotation [α]$_D^{25}$ −79.10 (c=1.04, CHCl$_3$)

NMR spectrum (270 MHz, CDCl$_3$) δ ppm: 1.18 (3H, d, J=7.0 Hz), 3.33 (1H, q, J=7.0 Hz), 3.39 (1H, tt, J=11.3, 4.6 Hz), 3.62 (1H, t, J=11.3 Hz), 3.64 (1H, t, J=11.3 Hz), 4.30 (1H, m), 4.41 (1H, m), 4.82 (1H, d, J=14.0 Hz), 5.00 (1H, s), 5.03 (1H, d, J=14.0 Hz), 5.05 (1H, d, J=4.6 Hz), 5.79 (1H, dd, J=15.2, 4.6 Hz), 6.58 (1H, dd, J=15.2, 9.5 Hz), 6.65–6.9 (6H, m), 7.3–7.5 (2H, m), 7.79 (2H, s).

EXAMPLE 28

(2R,3R)-2-(2,4-Difluorophenyl)-3-[[trans-2-[(1E,3E)-4-[6-(2,2,3,3-tetrafluoropropoxy)-3-pyridyl]-1,3-butadien-1-yl]-1,3-dioxan-5-yl]thio]-1-(1H-1,2,4-triazol-5-yl)-2-butanol

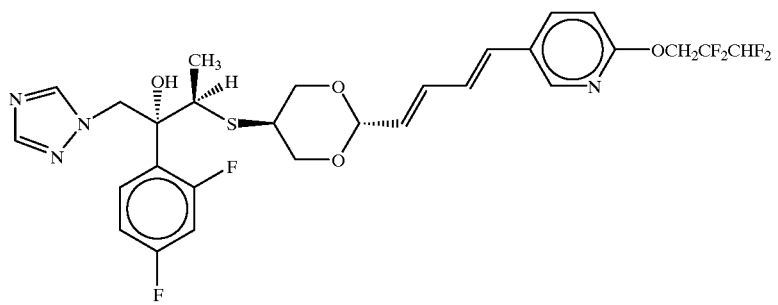

In 11 ml of methylene chloride were dissolved 404 mg (1.12 mmol) of (2R,3R)-2-(2,4-difluorophenyl)-3-[(1,3-dihydroxy-2-propyl)thio]-1-(1H-1,2,4-triazol-1-yl)-2-butanol and 501 mg (1.73 mmol) of (2E,4E)-5-[6-(2,2,3,3-tetrafluoropropoxy)-3-pyridyl]-2,4-pentadienal as described in Reference example 37, and 320 mg (1.68 mmol) of p-toluenesulfonic acid monohydrate and 4 g of molecular sieves 4A were added to the solution, followed by stirring of the resulting mixture at room temperature for 1 hour. The reaction mixture was poured into 20 ml of a 3% aqueous sodium hydrogencarbonate solution under ice-cooling and the mixture was stirred for 5 minutes. Then, the molecular sieves was removed by filtration and the organic layer was collected by fractions, followed by drying and evaporation of the solvent under reduced pressure. 908 mg of the thus obtained oil were subjected to column chromatography using 19 g of silica gel and eluted with a mixed solvent of hexane-ethyl acetate (1:1) to obtain 448 mg (yield: 63%) of the desired title compound as an oil.

Specific rotation $[\alpha]_D^{25}$ −58.6° (c=0.52, $CHCl_3$)

NMR spectrum (270 MHz, $CDCl_3$) δ ppm: 1.19 (3H, J=7.0 Hz), 3.33 (1H, q, J=7.0 Hz), 3.39 (1H, tt, J=11.2, 4.8 Hz), 3.62 (1H, t, J=11.2 Hz), 3.64 (1H, t, J=11.2 Hz), 4.30 (1H, ddd, J=11.2, 4.7, 2.1 Hz), 4.42 (1H, ddd, J=11.2, 4.7, 2.1 Hz), 4.74 (2H, brt, J=12.8 Hz), 4.82 (1H, d, J=13.9 Hz), 5.01 (1H, s), 5.03 (1H, d, J=13.9 Hz), 5.05 (1H, d, J=4.5 Hz), 5.78 (1H, d, J=15.5, 4.5 Hz), 6.01 (1H, tt, J=53.1, 4.6 Hz), 6.51–6.62 (2H, m), 6.65–6.78 ($3H_1$, m), 6.81 (1H, d, J=8.6 Hz), 7.35 (1H, m), 7.74 (1H, dd, J=8.6, 2.3 Hz), 7.79 (2H, s), 8.11 (1H, d, J=2.3 Hz).

EXAMPLE 29
(2R,3R)-2-(2,4-Difluorophenyl)-3-[[trans-2-[(1E,3E)-1-methyl-4-[4-(trifluoromethyl)phenyl]-1,3-butadien-1-yl]-1,3-dioxan-5-yl]thio]-1-(1H-1,2,4-triazol-1-yl)-2-butanol

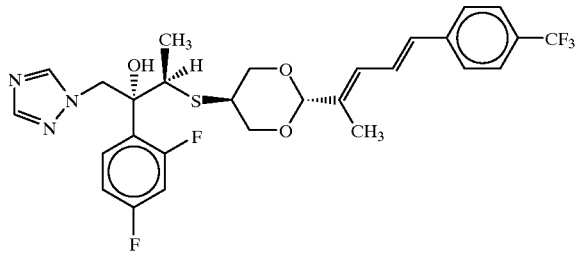

Reaction was carried out in the same manner as in Example 4 using (2R,3R)-2-(2,4-dipohenyl)-3-[(1,3-dihydroxy-2-propyl)thio]-1-(1H-1,2,4-triazol-5-yl)-2-butanol and (2E,4E)-2-methyl-5-[4-(trifluoromethyl)phenyl]-2,4-pentadienal to obtain the title compound, a major product as an oil in a yield of 31%.

NMR spectrum (270 MHz, $CDCl_3$) δ ppm: 1.19 (3H, d, J=7.3 Hz), 1.94 (3H, s), 3.34 (1H, q, J=7.3 Hz), 3.39 (1H, tt, J=11.2, 4.6 Hz), 3.36 (1H, t, J=11.2 Hz), 3.65 (1H, t, J=11.2 Hz), 4.33 (1H, m), 4.44 (1H, m), 4.83 (1H, d, J=13.9 Hz), 4.89 (1H, s), 5.02 (1H, s), 5.04 (1H, d, J=13.9 Hz), 6.41 (1H, d, J=11.2 Hz), 6.62 (1H, d, J=15.8 Hz), 6.7–6.8 (2H, m), 7.09 (1H, dd, J=15.8, 11.2 Hz), 7.36 (1H, m), 7.50 (2H, d, J=8.6 Hz), 7.56 (2H, d, J=8.6 Hz), 7.79 (1H, s), 7.80 (1H, s).

EXAMPLE 30
(RS)-3-Methyl-1-(1H-1,2,4-triazol-1-yl)-2-[4-(trifluoromethyl)phenyl]-3-[[trans-2-[(E)-2-[4-(trifluoromethyl)phenyl]vinyl]-1,3-dioxan-5-yl]thio]-2-butanol

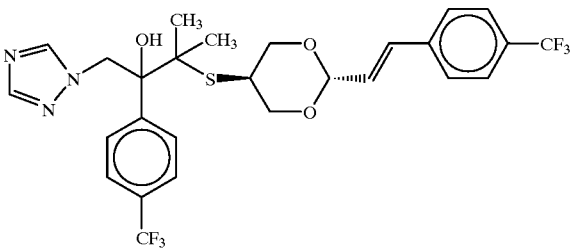

Reaction was carried out in the same manner as in Example 4 using (RS)-3-[(1,3-dihydroxy-2-propyl)thio]-3-methyl-2-[4-(trifluoromethyl)phenyl]-1-(1H-1,2,4-triazol-1-yl)-2-butanol as described in Reference example 55 and trans-4-(trifluoromethyl)cinnamaldehyde as described in Reference example 22 to obtain the title compound as a colorless foam.

NMR spectrum (270 MHz, $CDCl_3$) δ ppm: 1.36 (3H, s), 1.37 (3E, s), 3.5–3.7 (3H, m), 4.2–4.3 (1H, m), 4.4–4.5 (1H, m), 5.02 (2H, s), 5.11 (1H, d, J=4.1 Hz), 5.44 (1H, s), 6.25 (1H, dd, J=16.2, 4.1 Hz), 6.84 (1H, d, J=16.2 Hz), 7.4–7.6 (8H, m), 7.70 (1H, s), 7.93 (1H, s).

IR spectrum $\upsilon_{max}$ (KBr) $cm^{-1}$: 3404, 1618, 1508, 1328.

Mass spectrum m/e: 587, 568, 331, 298, 256, 201, 159, 131.

EXAMPLE 31
(RS)-3-Methyl-1-(1H-1,2,4-triazol-1-yl)-2-[4-(trifluoromethyl)phenyl]-3-[[trans-2-[(1E,3E)-4-[(trifluoromethyl)phenyl]-1,3-butadien-1-yl]-1,3-dioxan-5-yl]thio]-2-butanol

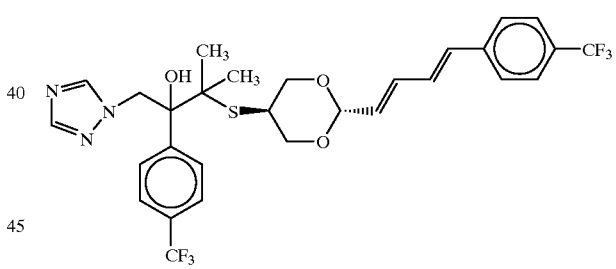

Reaction was carried out in the same manner as in Example 4 using (RS)-3-[ (1,3-dihydroxy-2-propyl) thio]-3-methyl-2-[4-(trifluoromethyl)phenyl]-1-(1H-1,2,4-triazol-1-yl)-2-butanol as described in Reference example 55 and (2E,4E)-5-[4-(trifluoromethyl) phenyl]-2,4-pentadienal as described in Reference example 25 to obtain the title compound, a major product as a colorless foam.

NMR spectrum (270 MHz, $CDCl_3$) δ ppm: 1.36 (3H, s), 1.37 (3H, s), 3.4–3.7 (3H, m), 4.2–4.3 (1H, m), 4.4–4.5 (1H, m), 5.01 (2H, s), 5.02 (1H, d, J=4.3 Hz), 5.39 (1H, s), 5.83 (1H, dd, J=15.2, 4.3 Hz), 6.59 (1H, dd, J=15.2, 10.7 Hz), 6.63 (1H, d, J=15.8 Hz), 6.85 (1H, dd, J=15.8, 10.7 Hz), 7.4–7.6 (8H, m), 7.73 (1H, s), 7.93 (1H, s).

IR spectrum $\upsilon_{max}$ (KBr) $cm^{-1}$: 3398, 1679, 1619, 1328, 1126.

Mass spectrum m/e: 614, 541, 494, 478, 406, 348, 256, 211.

EXAMPLE 32

(2R,3R)-2-(2,4-Difluorophenyl)-1-(1H-1,2,4-triazol-1-yl)-3-[[trans-2-[(1E,3E)-4-[4-(trifluoromethylthio)phenyl]-1,3-butadien-1-yl]-1,3-dioxan-5-yl]thio]-2-butanol

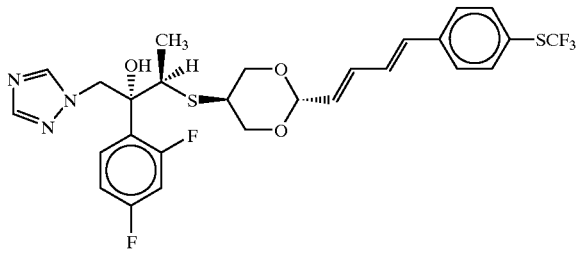

Reaction was carried out in the same manner as in Example 4 using (2R,3R)-2-(2,4-difluorophenyl)-3-[(1,3-dihydroxy-2-propyl)thiol-1-(1H-1,2,4-triazol-5-yl)-2-butanol and (2E,4E)-5-[4-(trifluoromethylthio)phenyl]-2,4-pentadienal to obtain the title compound, a major product as a colorless foam.

NMR spectrum (270 MHz, CDCl$_3$) δ ppm: 1.19 (3H, d, J=7.1 Hz), 3.3–3.5 (2H, m), 3.62 (1H, t, J=11.4 Hz), 3.64 (1H, t, J=11.4 Hz), 4.31 (1H, ddd, J=11.4, 4.7, 2.1 Hz), 4.42 (1H, ddd, J=11.4, 4.7, 2.1 Hz), 4.83 (1H, d, J=14.1 Hz), 5.01 (1H, s), 5.03 (1H, d, J=14.1 Hz), 5.06 (1H, d, J=4.5 Hz), 5.83 (1H, dd, J=15.7, 4.5 Hz), 6.60 (1H, dd, J=15.7, 10.3 Hz), 6.62 (1H, d, J=15.7 Hz), 6.7–6.8 (2H, m), 6.84 (1H, dd, J=15.7, 10.3 Hz), 7.3–7.4 (1H, m), 7.44 (2H, d, J=8.3 Hz), 7.60 (2H, d, J=8.3 Hz), 7.79 (2H, s).

IR spectrum υ$_{max}$ (KBr) cm$^{-1}$: 3389, 1621, 1680, 1621, 1501, 1117.

Mass spectrum m/e: 599, 580, 557, 530, 500, 438, 388, 376, 346, 284, 258, 224, 183.

EXAMPLE 33

(2R*,3R*)-3-[(Trans-2-[(1E,3E)-4-[4-(2,2,3,3-tetrafluoropropoxy)phenyl]-1,3-butadien-1-yl]-1,3-dioxan-5-yl]thio]-1-(1H-1,2,4-triazol-1-yl)-2-[4-(trifluoromethyl)phenyl]-2-butanol

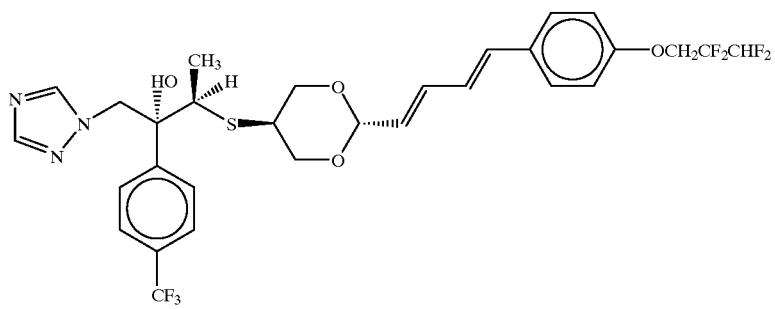

Reaction was carried out in the same manner as in Example 1 using (2R*,3R*)-3-[(1,3-dihydroxy-2-propyl)thio]-1-(1H-1,2,4-triazol-5-yl)-2-[4-(trifluoromethyl)phenyl]-2-butanol and (2E,4E)-5-[4-(2,2,3,3-tetrafluoropropoxy)phenyl]-2,4-pentadienal as described in Reference example 32 to obtain the title compound, a major product as an oil.

NMR spectrum (270 MHz, CDCl$_3$) δ ppm: 1.22 (3H, d, J=6.6 Hz), 3.16 (1H, q, J=6.6 Hz), 3.34 (1H, tt, J=11.2, 4.6 Hz), 3.58 (1H, t, J=11.2 Hz), 3.61 (1H, t, J=11.2 Hz), 4.27 (1H, m), 4.35 (2H, br t, J=11.9 Hz), 4.39 (1H, m), 4.57 (1H, d, J=13.9 Hz), 4.77 (1H, s), 5.02 (1H, d, J=4.6 Hz), 5.03 (1H, d, J=13.9 Hz), 5.72 (1H, dd, J=15.8, 4.6 Hz), 6.05 (1H, tt, J=52.8, 5.3 Hz), 6.5–6.75 (3H, m), 6.88 (2H, d, J=8.6 Hz), 7.36 (2H, d, J=8.6 Hz), 7.39 (2H, d, J=8.6 Hz), 7.54 (2H, d, J=8.6 Hz), 7.71 (1H, s), 7.83 (1H, s).

EXAMPLE 34

(2R*,3R*)-1-(1H-1,2,4-Triazol-1-yl)-2-[4-(trifluoromethyl)phenyl]-3-[[trans-2-[(!E,3E)-4-[4-(trifluoromethyl)phenyl]-1,3-butadien-1-yl]-1,3-dioxan-5-yl]thio]-2-butanol

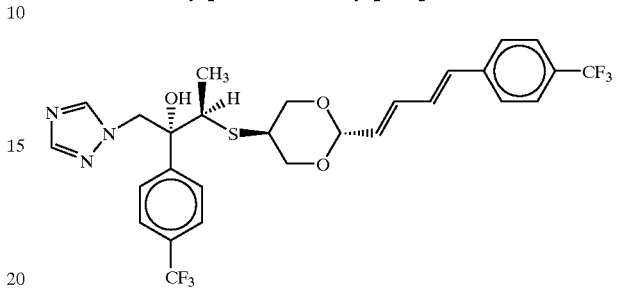

Reaction was carried out in the same manner as in Example 1 using (2R*,3R*)-3-methyl-2-[(1H-1,2,4-triazol-1-yl)methyl]oxirane and trans-5-(acetylthio)-2-[(1E,3E)-4-[4-(trifluoromethyl)phenyl]-1,3-butadien-1-yl]-1,3-dioxane to obtain the title compound as an oil in a yield of 71%.

NMR spectrum (270 MHz, CDCl$_3$) δ ppm: 1.22 (3H, d, J=7.0 Hz), 3.17 (1H, q, J=7.0 Hz), 3.36 (1H, tt, J=11.3, 4.7 Hz), 3.59 (1H, t, J=11.3 Hz), 3.62 (1H, t, J=11.3 Hz), 4.27 (1H, ddd, J=11.3, 4.7, 2.2 Hz), 4.39 (1H, ddd, J=11.3, 4.7, 2.2 Hz), 4.57 (1H, d, J=14.0 Hz), 4.80 (1E, s), 5.03 (1H, d, J=14.0 Hz), 5.05 (1H, d, J=4.5 Hz), 5.83 (1H, dd, J=15.3, 4.5 Hz), 6.59 (1H, dd, J=15.3, 10.7 Hz), 6.64 (1H, d, J=15.3 Hz), 6.85 (1H, dd, J=15.3, 10.7 Hz), 7.39 (2H, d, J=8.4 Hz), 7.49 (2H, d, J=8.3 Hz), 7.54 (2H, d, J=8.3 Hz), 7.57 (2H, d, J=8.4 Hz), 7.71 (1H, s), 7.83 (1H, s).

EXAMPLE 36

(2R,3R)-2-(2,4-Difluorophenyl)-1-(1H-1,2,4-triazol-1-yl)-3-[[trans-4-[(1E,3E)-4-[4-(trifluoromethyl)phenyl]-1,3-butadien-1-yl]cyclohexyl]thio]-2-butanol

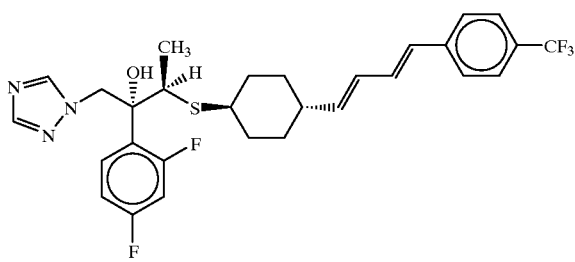

Reaction was carried out in the same manner as in Example 1 using (2R,3S)-2-(2,4-difluorophenyl)-3-methyl-2-[(1H-1,2,4-triazol-1-yl)methyl]oxirane and trans-1-(acetylthio)-4-[(1E,3E)-4-[4-(trifluoromethyl)phenyl]-1,3-butadien-1-yl]cyclohexane as described in Reference example 43 to obtain the title compound having a melting point of 74 to 76° C. in a yield of 59%.

Specific rotation $[\alpha]_D^{25}$ −830 (c=0.90, CHCl$_3$)

NMR spectrum (270 MHz, CDCl$_3$) δ ppm: 1.1–1.6 (4H, m), 1.17 (3H, d, J=7 Hz), 1.8–2.0 (2H, m), 2.0–2.2 (2H, m), 2.69 (1H, tt, J=12.3 Hz), 3.35 (1H, q, J=7 Hz), 4.64 (1H, s, OH), 4.83 (1H, d, J=15 Hz), 5.10 (1H, d, J=15 Hz), 5.83 (1H, dd, J=15, 7 Hz), 6.22 (1H, dd, J=1S, 10 Hz), 6.48 (1H, d, J=15 Hz), 6.74 (1H, t, J=8 Hz), 6.81 (1H, dd, J=15, 10 Hz), 7.1–7.5 (2H, m), 7.45 (2H, d, J=8 Hz), 7.54 (2H, d, J=8 Hz), 7.76 (1H, s), 7.84 (1H, s).

IR spectrum $\upsilon_{max}$ (CHCl3) cm$^{-1}$: 1615, 1500, 1325, 1125, 1068.

Mass spectrum m/e: 563, 544, 340, 310, 277, 224, 159, 127.

EXAMPLE 35

(2R,3R)-2-(2,4-Difluorophenyl)-1-(1H-1,2,4-triazol-1-yl)-3-[[trans-2-[(1E,3E)-4-[4-(trifluoromethylsulfinyl)phenyl]-1,3-butadien-1-yl]-1,3-dioxan-5-yl]thio]-2-butanol

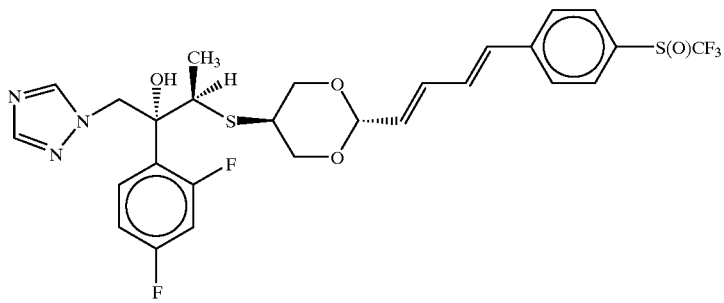

Reaction was carried out in the same manner as in Example 4 using (2R,3R)-2-(2,4-difluorophenyl)-3-[(1,3-dihydroxy-2-propyl)thio]-1-(1H-1,2,4-triazol-5-yl)-2-butanol and (2E,4E)-5-[4-(trifluoromethylsulfinyl)phenyl]-2,4-pentadienal to obtain the title compound, a major product as a colorless foam.

NMR spectrum (270 MHz, CDCl$_3$) δ ppm: 1.19 (3H, d, J=7.0 Hz), 3.3–3.5 (2H, m), 3.62 (1H, t, J=11.3 Hz), 3.64 (1H, t, J=11.3 Hz), 4.30 (1H, ddd, J=11.3, 4.8, 2.3 Hz), 4.42 (1H, ddd, J=11.3, 4.8, 2.3 Hz), 4.83 (1H, d, J=14.1 Hz), 5.01 (1H, s), 5.03 (1H, d, J=14.1 Hz), 5.06 (1H, d, J=4.5 Hz), 5.83 (1H, dd, J=15.9, 4.5 Hz), 6.60 (1H, dd, J=15.9, 10.6 Hz), 6.62 (1H, d, J=15.9 Hz), 6.7–6.8 (2H, m), 6.84 (1H, dd, J=15.9, 10.6 Hz), 7.3–7.4 (1H, m), 7.44 (2H, d, J=8.3 Hz), 7.60 (2H, d, J=8.3 Hz), 7.79 (2H, s).

Mass spectrum m/e: 616, 600, 547, 400, 370, 342, 284, 252, 224, 183.

EXAMPLE 37

(2R,3R)-2-(2,4-Difluorophenyl)-1-(1H-1,2,4-triazol-1-yl)-3-[[trans-2-[(1E,3E,5E)-6-[4-(trifluoromethyl)phenyl]-1,3,5-hexatrien-1-yl]-1,3-dioxan-5-yl]thio]-2-butanol

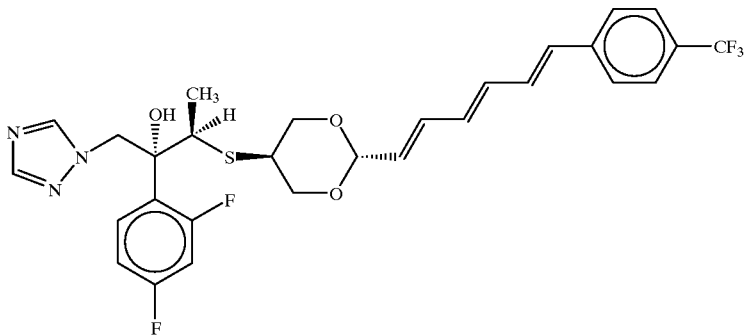

Reaction was carried out in the same manner as in Example 4 using (2R,3R)-2-(2,4-difluorophenyl)-3-[(1,3-dihydroxy-2-propyl)thio]1-1-(1H-1,2,4-triazol-1-yl)-2-butanol and (2E,4E,6E)-7-[4-(trifluoromethyl)phenyl]-2,4,6-heptatrienal as described in Reference example 28 to obtain the title compound, a major product as an oil in a yield of 65%.

NMR spectrum (270 MHz, CDCl$_3$) δ ppm: 1.18 (3H, d, J=6.6 Hz), 3.33 (1H, q, J=6.6 Hz), 3.38 (1H, tt, J=11.2, 4.6 Hz), 3.61 (1H, t, J=11.2 Hz), 3.63 (1H, t, J=11.2 Hz), 4.29 (1H, m), 4.40 (1H, m), 4.83 (1H, d, J=14.5 Hz), 5.00 (1H, s), 5.02 (1H, d, J=14.5 Hz), 5.03 (1H, d, J=4.6 Hz), 5.74 (1H, dd, J=15.2, 4.6 Hz), 6.35–6.55 (3H, m), 6.59 (1H, d, J=15.2 Hz), 6.7–6.8 (2H, m), 6.89 (1H, dd, J=15.2, 9.9 Hz), 7.35 (1H, m), 7.48. (2H, d, J=8.6 Hz), 7.56 (2H, d, J=8.6 Hz), 7.78 (1H, s), 7.79 (1H, s).

EXAMPLE 38
(RS)-2-(2,4-Difluorophenyl)-3-methyl-1-(1H-1,2,4-triazol-1-yl)-3-[[trans-2-[(1E,3E)-4-[4-(trifluoromethyl)phenyl]-1,3-butadien-1-yl]-1,3-dioxan-5-yl]thio]-2-butanol

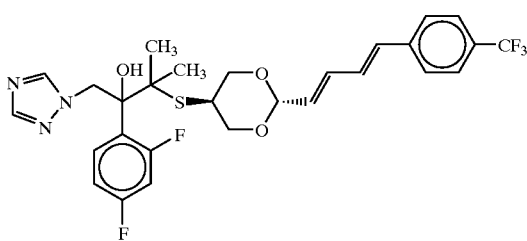

Reaction was carried out in the same manner as in Example 4 using (RS)-2-(2,4-difluorophenyl)-3-[(1,3-dihydroxy-2-propyl)thio]-3-methyl-1-(1H-1,2,4-triazol-1-yl)-2-butanol and (2E,4E)-5-[4-(trifluoromethyl)phenyl]-2,4-pentadienal as described in Reference example 25 to obtain the title compound, a major product as a colorless foam.

NMR spectrum (270 MHz, CDCl$_3$) δ ppm: 1.36 (6H, s), 3.5–3.6 (2H, m), 3.6–3.8 (2H, m), 4.2–4.4 (1, m), 4.4–4.6 (1H, m), 4.93 (1H, d, J=14.1 Hz), 5.03 (1H, d, J=4.3 Hz), 5.23 (1H, d, J=14.1 Hz), 5.56 (1H, s), 5.84 (1H, dd, J=15.4, 4.3 Hz), 6.5–6.7 (3H, m), 6.7–6.9 (2H, m), 7.50 (2H, d, J=8.4 Hz), 7.57 (2H, d, J=8.4 Hz), 7.6–7.7 (1H, m), 7.74 (1H, s), 8.05 (1H, s).

EXAMPLE 39
(2R,3R)-2-(2,4-Difluorophenyl)-1-(1H-1,2,4-triazol-1-yl)-3-[[trans-2-[(E)-4-[4-(trifluoromethyl)phenyl]-1-buten-3-yn-1-yl]-1,3-dioxan-5-yl]thio]-2-butanol

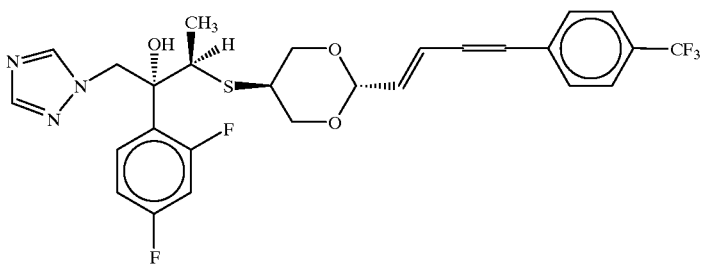

Reaction was carried out in the same manner as in Example 4 using (2R,3R)-2-(2,4-difluorophenyl)-3-[(1,3-dihydroxy-2-propyl)thio]-1-(1H-1,2,4-triazol-1-yl)-2-butanol and (E)-5-[4-(trifluoromethyl)phenyl]-2-penten-4-ynal as described in Reference example 48 to obtain the title compound, a major product as an oil in a yield of 70%.

Specific rotation [α]$_D^{25}$ −65.10 (c=0.97, CHCl$_3$)

NMR spectrum (270 MHz, CDCl$_3$) δ ppm: 1.19 (3H, d, J=7.0 Hz), 3.33 (1H, q, J=7.0 Hz), 3.39 (1H, tt, J=11.4, 4.9 Hz), 3.60 (1H, t, J=11.4 Hz), 3.62 (1H, t, J=11.4 Hz), 4.30 (1H, m), 4.42 (1H, m), 5.0–5.1 (2H, m), 5.04 (1H, d, J=3.2 Hz), 6.12 (1H, d, J=16.0 Hz), 6.18 (1H, dd, J=16.0, 3.2 Hz), 6.7–6.8 (2H, m), 7.36 (1H, m), 7.54 (2H, d, J=8.5 Hz), 7.58 (2H, d, J=8.5 Hz), 7.79 (2H, s).

EXAMPLE 40
(2R,3R)-2-(2,4-Difluorophenyl)-3-[[trans-2-phenyl-1,3-dioxan-5-yl]thio]-1-(1H-1,2,4-triazol-1-yl)-2-butanol

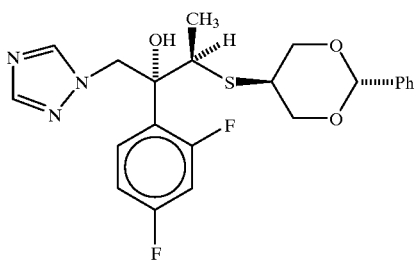

In 20 ml of dimethylformamide were dissolved 1.65 g (6.57 mmol) of (2R,3S)-2-(2,4-difluorophenyl)-3-methyl-2-(1H-1,2,4-triazol-1-yl)methyl]oxirane and 2.00 g (8.40 mmol) of trans-4-(acetylthio)-2-phenyl-1,3-dioxane as described in Reference example 1, and 2.5 ml (4.00 mmol) of a 1.6M sodium methoxide-methanol solution were added to the solution under a nitrogen atmosphere, followed by heating of the resulting mixture with stirring at 65° C. for 2 hours. After cooling, ethyl acetate was added to the reaction mixture and the resulting mixture was washed with a saturated aqueous NaCl solution and dried, followed by evaporation of the solvent under reduced pressure. The thus obtained crude product was subjected to column chromatography using 60 g of silica gel and eluted with a mixed solvent of benzene-ethyl acetate (5:1) to obtain 2.53 g (yield: 91%) of the title compound as a solid. The solid was recrystallized from ethyl acetate-hexane to obtain a pure product having a melting point of 58 to 60° C.

Specific rotation $[\alpha]_D^{25}$ −88° (c=1.07, CHCl$_3$)

IR spectrum $\upsilon_{max}$(CECl$_3$) cm$^{-1}$: 3400, 1615, 1500, 1139.

NMR spectrum (270 MHz, CDCl$_3$) δ ppm: 1.21 (3H, d, J=7.3 Hz), 3.36 (1H, q, J=7.3 Hz), 3.48 (1H, tt, J=11.2, 4.6 Hz), 3.75 (1H, t, J=11.2 Hz), 3.77 (1H, t, J=11.2 Hz), 4.40 (1H, ddd, J=11.2, 4.6, 2.6 Hz), 4.51 (1H, ddd, J=11.2, 4.6, 2.6 Hz), 4.84 (1H, d, J=13.9 Hz), 5.02 (1H, s), 5.05 (1H, d, J=13.9 Hz), 5.49 (1H, s), 7.7–7.8 (2H, m), 7.3–7.45 (4H, m), 7.45–7.53 (2H, m), 7.79 (2H, s).

REFERENCE EXAMPLE 1
Trans-4-(acetylthio)-2-phenyl-1,3-dioxane

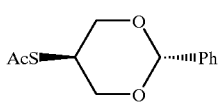

In 200 ml of dimethylformamide were dissolved 29.0 g (86.8 mmol) of cis-2-phenyl-4-(p-toluenesulfonyloxy)-1,3-dioxane and 17.0 g (149 mmol) of sodium thioacetate, and the solution was heated at 115 to 120° C. under a nitrogen atmosphere for 1 hour. After cooling, benzene was added to the reaction mixture and the mixture was washed with water, followed by evaporation of the solvent. The thus obtained brown residue was subjected to column chromatography using silica gel and the fractions eluted with a mixed solvent of benzene-hexane (2:1) were collected, followed by recrystallization from a mixed solvent of benzene-hexane to obtain 8.99 g (yield: 43%) of the title compound having a melting point of 95 to 96° C.

NMR spectrum (270 MHz, CDCl$_3$) δ ppm: 2.37 (3H, s), 3.79 (2H, t, J=11.2 Hz), 4.03 (1H, tt, J=11.2, 4.6 Hz), 4.31 (2H, dd, J=11.2, 4.6 Hz), 5.47 (1H, s), 7.35–7.5 (5H, m).

IR spectrum $\upsilon_{max}$(CHCl$_3$) cm$^{-1}$: 1690, 1383, 1146, 1084.

Mass spectrum m/e: 238 (M$^+$), 237, 195, 162(100%), 149, 116, 107, 73.

REFERENCE EXAMPLE 2
(2R,3R)-2-(2,4-Difluorophenyl)-3-[(1,3-dihydroxy-2-propyl]thio]-1-(1H-1,2,4-triazol-1-yl)-2-butanol

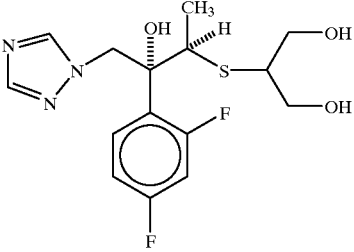

In 3.5 ml of methanol were dissolved 253 mg of (2R, 3R)-2-(2,4-difluorophenyl)-3-[[trans-2-phenyl-1,3-dioxan-5-yl]thio]-1-(1H-1,2,4-triazol-1-yl)-2-butanol as described in Example 40, and 0.35 ml of a 4N HCl-dioxane solution were added to the solution, followed by stirring of the resulting mixture at room temperature for 30 minutes. To the reaction mixture were added 250 mg of a NaHCO3 powder, and the mixture was stirred for 10 minutes, followed by filtration of the reaction mixture and concentration of the filtrate under reduced pressure. The thus obtained oil was subjected to column chromatography using 5 g of silica gel and eluted with 10% methanol-ethyl acetate to obtain 179 mg (yield: 88%) of the title compound as a viscous oil.

Specific rotation $[\alpha]_D^{25}$ −61° (c=1.05, CHCl$_3$)

IR spectrum $\upsilon_{max}$(CHCl$_3$) cm$^{-1}$: 3400, 1618, 1500.

NMR spectrum (60 MHz, CDCl$_3$+D$_2$O) δ ppm: 1.20 (3H, d, J=6.5 Hz), 3.0–4.0 (6H, m), 4.80 (1H, d, J=14 Hz), 5.16 (1H, d, J=14 Hz), 6.6–7.0 (2H, m), 7.43 (1H, td, J=9, 8 Hz), 7.74 (1H, s), 7.86 (1H, s).

REFERENCE EXAMPLE 3
Trans-5-[(4-chlorobenzyl)thio]-2-phenyl-1,3-dioxane

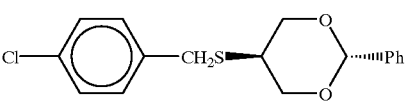

After 240 mg (5.50 mmol) of 55% sodium hydride were washed with hexane, it was suspended in 15 ml of dimethylformamide and 903 mg (5.70 mmol) of 4-chlorobenzylmercaptane were added to the resulting suspension with stirring under nitrogen atmosphere. After 15 minutes, 1.66 g (4.96 mmol) of cis-5-(p-toluenesulfonyloxy)-2-phenyl-1,3-dioxane were added to the mixture and the resulting mixture was stirred at 75° C. for 1 hour. After cooling, benzene was added to the reaction mixture and the mixture was washed with water and then an aqueous NaCl solution. After the solvent was distilled off, the thus obtained crystalline residue was recrystallized from a mixed solvent of benzene-hexane to obtain 670 mg (yield: 42%) of the title compound having a melting point of 95 to 99° C. as a flaky crystalline solid.

NMR spectrum (60 MHz, CDCl$_3$) δ ppm: 3.02 (IF, tt, J=11, 5 Hz), 3 (2H, t, J=11 Hz), 3.72 (2H, s), 4.21 (2H, dd, J=11, 5 Hz), 5.39 (1H, 7.30 (5H, s), 7.38 (4H, s)

REFERENCE EXAMPLE 4
2-[(4-Chlorobenzyl)thio]-1,3-propanediol

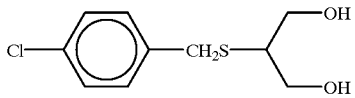

In 10 ml of methanol were dissolved 750 mg of trans-5 chlorobenzyl)thio]-2-phenyl-1,3-dioxane, and 1 ml of a 4N hydrogen chloride-dioxane solution was added to the solution, followed by stirring of the resulting mixture at room temperature for 1 hour. After 750 mg of sodium hydrogencarbonate (powder) were added to the reaction mixture and the resulting mixture was stirred for 15 minutes, the solid was removed by filtration and the solvent was distilled off. Ethyl acetate was added to the residue and the insolubles were removed by filtration. The crystal obtained by evaporation of the solvent was recrystallized from a mixed solvent of benzene-hexane to obtain 468 mg (yield: 86%) of the title compound having a melting point of 70 to 75° C.

REFERENCE EXAMPLE 5
Trans-5-[(4-chlorobenzyl)thio]-2-[(E)-1-methyl-2-[4-(trifluoromethyl)phenyl]vinyl]-1,3-dioxane

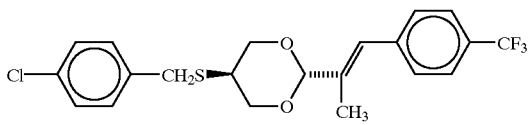

In 12 ml of benzene were dissolved 341 mg (1.46 mmol) of 2-[(4-chlorobenzyl)thio]-1,3-propanediol and 375 mg (1.75 mmol) of (E)-4-(trifluoromethyl)-a-methylcinnamaldehyde, and 3 mg of p-toluenesulfonic acid were added to the solution, followed by heating of the resulting mixture with reflux under nitrogen atmosphere for 2 hours. After cooling, the reaction mixture was washed with an aqueous sodium hydrogencarbonate solution. The residue obtained by evaporation of the solvent was subjected to column chromatography using 15 g of silica gel. The fractions eluted with a mixed solvent of hexane-ethyl acetate (9:1) were collected and the thus obtained solid was washed with hexane to obtain 370 mg (yield: 59%) of the title compound having a melting point of 93 to 95° C.

NMR spectrum (270M[]z, CDCl$_3$) δ ppm: 1.87 (3H, 6), 2.99 (1H, tt, J=11.2, 4.6 Hz), 3.58 (2H, dd, J=11.9, 11.2 Hz), 3.73 (2H, S), 4.15 (2H, dd, J=11.9, 4.6 Hz), 4.87 (1H, s), 6.68 (1H, br s), 7.25–7.3 (4H, m), 7.36 (2H, d, J=7.9 Hz), 7.57 (2H, d, J=7.9 Hz).

REFERENCE EXAMPLE 6
Trans-5-[(4-chlorobenzyl)sulfinyl]-2-[(E)-1-methyl-2-[4-(trifluoromethyl)phenyl]vinyl]-1,3-dioxane

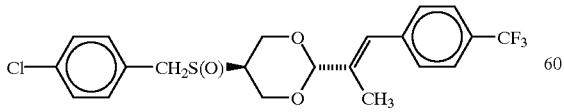

In 10 ml of methylene chloride were dissolved 382 mg (0.89 mmol) of trans-5-[(4-chlorobenzyl)thio]-2-[(E)-1-methyl-2-[4-(trifluoromethyl)phenyl]vinyl]-1,3-dioxane, and 188 mg (0.92 mmol) of m-chloroperbenzoic acid (purity: 85%) were added to the solution, followed by stirring of the resulting mixture for 15 minutes. The reaction mixture was washed with an aqueous sodium hydrogencarbonate solution and the solid obtained by evaporation of the solvent was washed with a mixed solvent of ethyl acetate-hexane to obtain 328 mg (yield: 83%) having a melting point of 192 to 194° C.

NMR spectrum (60 MHz, CDCl$_3$) δ ppm: 1.88 (3H, d, J=1.5 Hz), 2.8–3.3 (1H, m), 3.8–4.5 (4H, m), 4.01 (2H, s), 4.95 (1H, s), 6.73 (1H, br s), 7.15–7.75 (8H, m).

REFERENCE EXAMPLE 7
Trans-4-(acetylthio)-2-[(E)-1-methyl-2-[4-(trifluoromethyl)phenyl]vinyl]-1,3-dioxane

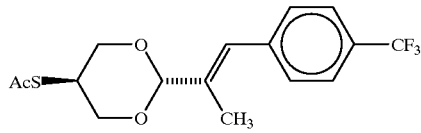

In 8 ml of a mixed solvent of tetrahydrofuran-acetonitrile (1:1) were dissolved 309 mg (0.696 mmol) of trans-5-[(4-chlorobenzyl)sulfinyl]-2-[(E)-1-methyl-2-[4-(trifluoromethyl)phenyl]vinyl]-1,3-dioxane, and 500 mg (4.67 mmol) of 2,6-lutidine were added to the solution. To the resulting mixture were added dropwise 500 mg (2.4 mmol) of trifluoroacetic anhydride with stirring at 0° C. for about 5 minutes. After 10 minutes, about 5 ml of an aqueous sodium hydrogencarbonate solution were added to the reaction mixture and the mixture was stirred at 5 minutes, followed by extraction with ethyl acetate. An oily residue (about 350 mg) obtained by evaporation of the solvent was dissolved in 5 ml of methylene chloride and 210 mg of triethylamine were added to the solution at 0° C., followed by addition of 109 mg of acetyl chloride to the resulting mixture. After 5 minutes, the reaction mixture was washed with water and the solvent was distilled off. The residue was subjected to column chromatography using 10 g of silica gel and eluted with a mixed solvent of hexane-benzene (1:1 to 1:2) to obtain 186 mg (yield: 77%) of the title compound as a crystalline solid. The crystalline solid was recrystallized from a mixed solvent of benzene-hexane to obtain a plate-like crystalline solid having a melting point of 128 to 129° C.

NMR spectrum (270 MHz, CDCl$_3$) δ ppm: 1.92 (3H, s), 2.36 (3H, s), 3.70 (2H, t, J=11.2 Hz), 3.96 (1H, tt, J=11.2, 4.6 Hz), 4.25 (2H, dd, J=11.2, 4.6 Hz), 4.94 (1H, s), 6.70(1H, br s), 7.39 (2H, d, J=8.2 Hz), 7.59 (2H, d, J=8.2 Hz).

REFERENCE EXAMPLE 8
Ethyl (2E,4E)-3-methyl-5-[4-(trifluoromethyl)phenyl]-2,4-pentadienoate

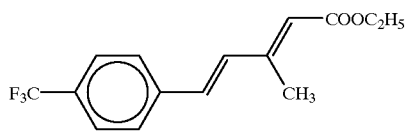

After 45 mg (1.03 mmol) of 55% sodium hydride were washed with hexane, it was suspended in 3 ml of 1,2-dimethoxyethane and 273 mg (1.03 mmol) of triethyl 3-methyl-4-phosphonocrotonate were added to the resulting mixture with stirring at 0° C. under nitrogen atmosphere. After 15 minutes, 100 mg (0.57 mmol) of 4-(trifluoromethyl)benzaldehyde were added to the mixture and the resulting mixture was stirred for 10 minutes. After ice-water was added to the reaction mixture, the mixture was extracted with ethyl acetate. The crude product obtained by evaporation of the solvent was subjected to column chromatography using 5 g of silica gel and eluted with a mixed solvent of ethyl acetate-hexane (4:96) to obtain 159 mg (yield: 97%) of a 5:1 mixture of the title compound, a (2E,4E) isomer and a (2E,4E) isomer as an oil.

NMR spectrum (270 MHz, CDCl$_3$) δ ppm: (2E, 4E)-isomer, 1.31 (3H, t, J=6.6 Hz), 2.41 (3H, s), 4.20 (2H, q, J=6.6 Hz), 5.95 (1H, s), 6.86 (1H, d, J=16.5 Hz), 6.95 (1H, d, J=16.5 Hz), 7.5–7.65 (4H, m): (2E, 4E)-isomer (main signal), 2.14 (3H, s), 5.82 (1H, s), 6.92 (1H, d, J=16.BHz), 8.49 (1H, d, J=16.5 Hz).

REFERENCE EXAMPLE 9
(2E,4E)-3-Methyl-5-[4-(trifluoromethyl)phenyl]-2,4-pentadien-1-ol

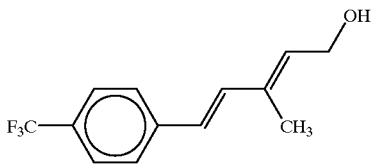

After a solution in which 150 mg (0.53 mmol) of ethyl (4E)-3-methyl-5-[4-(trifluoromethyl)phenyl]-2,4-pentadienoate ((2E)/(2Z)=5/1) as described in Reference example 8 were dissolved in 2 ml of toluene was stirred at 0° C., 0.7 ml (1.06 mmol) of a 1.SM diisobutyl aluminum hydride-toluene solution were added to the solution. After 20 minutes, ice-water was added to the reaction mixture and the mixture was stirred for 10 minutes. The insolubles were removed by filtration using Celite and the filtrate was extracted with ethyl acetate and dried, followed by evaporation of the solvent to obtain an oil. The oil was subjected to column chromatography using 5 g of silica gel and eluted with a mixed solvent of 30 to 40% ethyl acetate-hexane to obtain 90 mg of the title compound as an oil.

NMR spectrum (270 MHz, CDCl$_3$) δ ppm: 1.34 (1H, br s), 1.93 (3H, s), 4.37 (2H, d, J=6.5 Hz), 5.87 (1H, t, J=6.5 Hz), 6.58 (1H, d, J=16.1 Hz), 6.88 (1H, d, J=16.1 Hz), 7.50 (2H, d, J=8.5 Hz), 7.57 (2H, d, J=8.5 Hz).

REFERENCE EXAMPLE 10
(2E,4E)-3-Methyl-5-[4-(trifluoromethyl)phenyl]-2,4-pentadienal

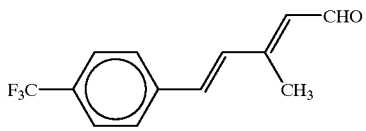

In 10 ml of methylene chloride were dissolved 460 mg (1.90 mmol) of (2E,4E)-3-methyl-5-[4-(trifluoromethyl)phenyl]-2,4-pentadien-1-ol, and 5 g of active manganese dioxide were added to the mixture, followed by stirring of the resulting mixture at room temperature for 30 minutes. The solid was removed by filtration, and after the filtrate was concentrated, it was purified over silica gel chromatography (eluting solvent: 4% ethyl acetate-hexane) to obtain 460 mg of the title compound as an oil.

NMR spectrum (270 MHz, CDCl$_3$) δ ppm: 2.41 (3H, s), 6.13 (1H, d, J=8.0 Hz), 6.96 (1H, d, J=16.1 Hz), 7.09 (1H, d, J=16.1 Hz), 7.55–7.7 (4H, m), 10.19 (1H, d, J=8.0 Hz).

REFERENCE EXAMPLE 11
4-(Acetylthio)-1-(tert-butoxycarbonyl)piperidine

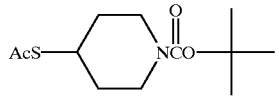

In 40 ml of dimethylformamide were dissolved 4.12 g (14.7 mmol) of 1-(tert-butoxycarbonyl)-4-(methanesulfonyloxy)piperidine, and 2.53 g (2.21 mmol) of potassium thioacetate were added to the solution, followed by stirring of the resulting mixture at 105° C. for 4 hours under nitrogen atmosphere. After cooling, the reaction mixture was diluted with ethyl acetate and washed with water and then a saturated aqueous NaCl solution, followed by evaporation of the solvent. The thus obtained residue was subjected to silica gel column chromatography and the fractions eluted with a mixed solvent of hexane-ethyl acetate (5:1) were collected to obtain 5.19 g (yield: 81%) of the title compound as an oil.

NMR spectrum (270 MHz, CDCl$_3$) δ ppm: 1.46 (9H, s), 1.5–1.6 (2H, m), 1.9–2.0 (2H, m), 2.33 (3H, s), 3.0–3.1 (2H, m), 3.5–3.7 (1H, m), 3.8–3.9 (2H, m)

Mass spectrum m/e: 259, 244, 216, 202, 186, 183, 160, 144, 127, 116, 97, 84, 57.

REFERENCE EXAMPLE 12
1-(tert-Butoxycarbonyl)-4-mercaptopiperidine

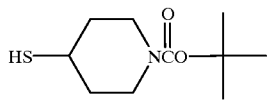

In dry methanol were dissolved 520 mg (2 mmol) of 4-(acetylthio)-1-(tert-butoxycarbonyl)piperidine, and 420 μl (2 mmol) of a 28% sodium methoxide-methanol solution were added to the mixture under ice-cooling and under a nitrogen atmosphere, followed by stirring of the resulting mixture for 40 minutes. Then, 173 μl of acetic acid were added to the mixture and the solvent was distilled off at room temperature, followed by diluting of the residue with ethyl acetate. The mixture was washed successively with an aqueous sodium hydrogencarbonate solution and an aqueous NaCl solution in the order and the solvent was distilled off to obtain 430 mg of reddish orange oil. This product was used for a subsequent reaction without purification.

NMR spectrum (270 MHz, CDCl$_3$) δ ppm: 1.46 (9H, s), 1.5–1.6 (2H, m), 1.9–2.0 (2H, m), 2.8–3.0 (3H, m), 3.9–4.1 (2H, m).

Mass spectrum m/e: 217, 202, 184, 161, 144, 127, 117, 84, 82.

REFERENCE EXAMPLE 13
(2R,3R)-2-(2,4-Difluorophenyl)-3-(1H-1,2,4-triazol-1-yl)-3-[[1-(tert-butoxycarbonyl)piperidin-4-yl]thio]-2-butanol

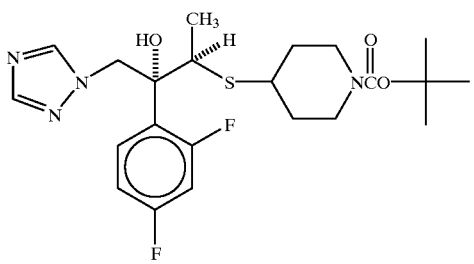

In 6 ml of dimethylformamide was dissolved 1-(tert-butoxycarbonyl)-4-mercaptopiperidine (corresponding to 2 mmol) as described in Reference example 12, and 86 mg (1.97 mmol) of 55% sodium hydride were added to the solution at 0° C. under a nitrogen atmosphere, followed by stirring of the resulting mixture at the same temperature for 20 minutes. Then, 503 mg (2.00 mmol) of (2R,3S)-2-(2,4-difluorophenyl)-3-methyl-2-[(1H-1,2,4-triazol-1-yl)methyl] oxirane were added to the reaction mixture and the mixture was stirred at 60° C. for 3 hours. After cooling, ethyl acetate was added to the reaction mixture to dilute it and washed successively with water and a saturated aqueous NaCl solution. An oil obtained by evaporation of the solvent was subjected to silica gel column chromatography and eluted with ethyl acetate to obtain 557 mg (yield: 53%) of the desired compound as an oil.

NMR spectrum (270 MHz, CDCl$_3$) δ ppm: 1.17 (3H, d, J=6.6 Hz), 1.47 (9H, s), 1.4–1.6 (2H, m), 1.9–2.1 (2H, m), 2.9–3.1 (3H, m), 3.34 (1H, q, J=6.6 Hz), 3.9–4.1 (2H, m), 4.77 (1H, s), 4.82 (1H, d, J=14.2 Hz), 5.09 (1H, d, J=14.2 Hz), 6.7–6.8 (2H, m), 7.3–7.4 (1H, m), 7.77 (1H, s), 7.82 (1H, s).

IR spectrum $\upsilon_{max}^{KBr}$cm$^{-1}$: 3401, 1691.

Mass spectrum m/e: 468, 408, 395, 365, 321, 284, 253, 224, 188, 166, 144, 127.

REFERENCE EXAMPLE 14
(2R,3R)-2-(2,4-Difluorophenyl)-3-(1H-1,2,4-triazol-1-yl)-3-[(piperidin-4-yl)thio]-2-butanol dihydrochloride

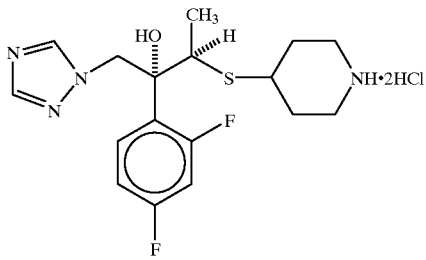

In 20 ml of ethyl acetate were dissolved 557 mg (1.05 mmol) of (2R,3R)-2-(2,4-difluorophenyl)-3-(1H-1,2,4-triazol-1-yl)-3-[[1-(tert-butoxycarbonyl)piperidin-4-yl]thio]-2-butanol, and 2.63 ml (10.5 mmol) of a 4N hydrogen chloride-ethyl acetate solution were added to the solution, followed by stirring of the resulting mixture at 40° C. for 8 hours. After cooling, the precipitated solid was collected by filtration and washed with hexane to obtain 460 mg (yield: 100%) of the desired compound as a colorless powder.

NMR spectrum (270 MHz, DMSO-d6+CDCl$_3$) δ ppm: 1.23 (3H, d, J=6.6 Hz), 1.8–2.0 (2H, m), 2.3–2.5 (2H, m), 3.1–3.4 (3H, m), 3.74 (1H, q, J=6.6 Hz), 4.79 (1H, d, J=14.2 Hz), 5.05 (1H, d, J=14.2 Hz), 5.3–5.6 (1H, br s), 6.8–6.9 (1H, m), 7.0–7.1 (1H, m), 7.2–7.3 (1H, m), 7.79 (1H, s), 8.28 (1H, s).

IR spectrum $\upsilon_{max}^{KBr}$cm$^{-1}$: 3366, 3094, 2725, 2483.

Mass spectrum m/e: 368, 308, 286, 284, 253, 224, 213, 183, 165, 144, 116, 113, 84.

REFERENCE EXAMPLE 15
4-(Acetylthio)piperidine hydrochloride

In 45 ml of ethyl acetate were dissolved 1.25 g (4.82 mmol) of 4-(acetylthio)-1-(tert-butoxycarbonyl)piperidine as described in Reference example 11, and 12.0 ml (48.2 mmol) of a 4N hydrogen chloride-ethyl acetate solution were added to the solution, followed by stirring of the resulting mixture at 50° C. for 4 hours. After cooling, the precipitated solid was collected by filtration and washed with hexane to obtain 885 mg (yield: 94%) of the desired compound as a slightly yellow powder.

NMR spectrum (270 MHz, CD$_3$OD) δ ppm: 1.8–2.0 (2H, m), 2.1–2.3 (2H, m), 2.35 (3H, s), 3.1–3.3 (2H, m), 3.3–3.5 (2H, m), 3.6–3.8 (1H, m).

REFERENCE EXAMPLE 16
4-(Acetylthio)-1-[(E)-4-(trifluoromethoxy)cinnamoyl]-piperidine

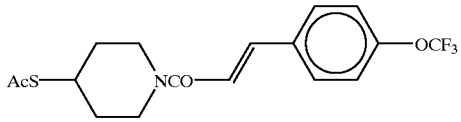

In 17 ml of dichloromethane were suspended 1.28 g (6.53 mmol) of 4-(acetylthio)piperidine hydrochloride, and 2.27 ml (16.3 mmol) of triethylamine were added dropwise to the suspension with stirring under ice-cooling. Then, a solution in which 1.80 g (7.18 mmol) of (E)-4-(trifluoromethoxy) cinnamoyl chloride were dissolved in 6 ml of dichloromethane was added dropwise to the reaction mixture, followed by stirring of the mixture at the same temperature for 1 hour. The reaction mixture was subjected to silica gel column chromatography and eluted with a mixed solvent of hexane-ethyl acetate (2:1 to 1:1) to obtain 2.32 g (yield: 95%) of the desired compound as a slightly yellow solid.

NMR spectrum (270 MHz, CDCl$_3$) δ ppm: 1.5–1.7 (2H, m), 1.9–2.1 (2H, m), 2.34 (3H, s), 3.1–3.3 (1H, m), 3.3–3.5 (1H, m), 3.7–3.8 (1H, m), 3.9–4.0 (1H, m), 4.2–4.4 (1H, m), 6.85 (1H, d, J=15.5 Hz), 7.21 (2H, d, J=8.6 Hz), 7.54 (2H, d, J=8.6 Hz), 7.63 (1H, d, J=15.5 Hz).

Mass spectrum m/e: 373, 330, 298, 256, 228, 215, 187, 158, 136, 116, 101.

REFERENCE EXAMPLE 17
3-(Acetylthio)-1-(tert-butoxycarbonyl)azetidine

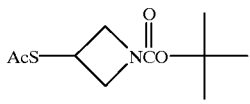

An orange oil obtained from 1-(tert-butoxycarbonyl)-3-(methanesulfonyloxy)azetidine according to the procedure of Reference example 11.

NMR spectrum (270 MHz, CDCl$_3$) δ ppm: 1.44 (9H, s), 2.33 (3H, s), 3.81 (2H, dd, J=9.0, 5.5 Hz), 4.1–4.2 (1H, m), 4.37 (2H, t, J=9.0 Hz).

REFERENCE EXAMPLE 18
(2R,3R)-2-(2,4-Difluorophenyl)-1-(1H-1,2,4-triazol-1-yl)-3-[[1-(tert-butoxycarbonyl)azetidin-3-yl]thio]-2-butanol

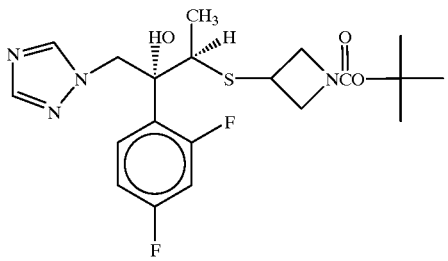

A pale yellow foam obtained from 3-(acetylthio)-1-(tert-butoxycarbonyl)azetidine according to the procedure of Reference examples 12 and 13.

NMR spectrun (270 MHz, CDCl$_3$) δ ppm: 1.13 (3H, d, J=7.1 Hz), 1.45 (9H, s), 3.27 (1H, q, J=7.1 Hz), 3.7–3.9 (2H, m), 3.9–4.0 (1H, m), 4.2–4.4 (2H, m), 4.84 (1H, d, J=14.1 Hz), 4.98 (1H, s), 5.04 (1H, d, J=14.1 Hz), 6.7–6.9 (2H, m), 7.3–7.4 (1H, m), 7.78 (1H, s), 7.80 (1H, s).

IR spectrum $\upsilon_{max}^{KBr}$ cm$^{-1}$: 3405, 1701.

Mass spectrum m/e: 441, 425, 385, 367, 341, 311, 284, 252, 224, 199, 183, 165, 141, 127, 88.

REFERENCE EXAMPLE 19
(2R,3R)-2-(2,4-Difluorophenyl)-1-(1H-1,2,4-triazol-1-yl)-3-[(azetidin-3-yl)thio]-2-butanol dihydrochloride

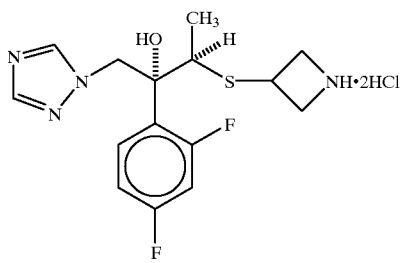

A slightly yellow powder obtained from (2R,3R)-2-(2,4-difluorophenyl)-1-(1H-1,2,4-triazol-1-yl)-3-[[1-(tert-butoxycarbonyl)azetidin-3-yl]thio]-2-butanol according to the procedure of Reference example 14.

NMR spectrum (270 MHz, CDCl$_3$) δ ppm: 1.16 (3H, d, J=6.6 Hz), 3.52 (1H, q, J=6.6 Hz), 3.9–4.3 (3H, m), 4.3–4.6 (2H, m), 4.98 (1H, d, J=14.2 Hz), 5.43 (1H, d, J=14.2 Hz), 6.6–6.9 (2H, m), 7.2–7.4 (1H, m), 8.40 (1H, s), 8.95 (1H, s), 9.0–9.6 (1H, br).

REFERENCE EXAMPLE 20
Ethyl trans-4-(trifluoromethyl)cinnamate

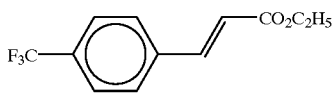

After 903 mg (20.7 mmol) of 55% sodium hydride were washed with hexane, it was suspended in 60 ml of 1,2-dimethoxyethane, and 4.63 g (20.7 mmol) of triethyl phosphonoacetate were added dropwise thereto while the suspension was stirred at 0° C. under nitrogen atmosphere. After 15 minutes, 2.00 g (11.5 mmol) of 4-(trifluoromethyl)benzaldehyde were added to the resulting mixture at the same temperature, followed by stirring of the mixture for 15 minutes. Ethyl acetate was added to the reaction mixture and the resulting mixture was washed with water. After drying, an oily residue obtained by evaporation of the solvent was subjected to column chromatography using silica gel and eluted with 4% ethyl acetate-hexane to obtain the title compound having a melting point of 31 to 32.5° C. in a yield of 98%.

NMR spectrum (270 MHz, CDCl$_3$) δ ppm: 1.35 (3H, t, J=7.3 Hz), 4.48 (2H, q, J=7.3 Hz), 6.51 (1H, d, J=16.2 Hz), 7.66 (4H, s), 7.69 (1H, d, J=16.2 Hz).

REFERENCE EXAMPLE 21
Trans-4-(trifluoromethyl)cinnamyl alcohol

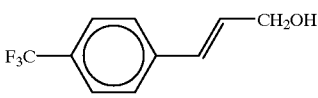

In 15 ml of toluene were dissolved 3.00 g (12.3 mmol) of ethyl trans-4-(trifluoromethyl)cinnamate, and 16.4 ml (24.6 mmol) of a 1.5 M diisobutyl aluminum hydride-toluene solution were added to the solution with stirring at 0° C. After 20 minutes, ice-water was added to the reaction mixture and the mixture was stirred for 10 minutes, followed by removal of the insolubles by filtration using Celite. The filtrate was extracted with ethyl acetate and, after drying, the solvent was distilled off to obtain a crystalline residue. The residue was recrystallized from a mixed solvent of benzene-hexane to obtain 2.36 g (yield: 96%) of the title compound having a melting point of 53 to 55° C.

NMR spectrum (270 MHz, CDCl$_3$) δ ppm: 1.55 (1H, t, J=5.9 Hz), 4.37 (2H, br t), 6.46 (1H, dt, J=16.2, 5.3 Hz), 6.67 (1H, d, J=16.2 Hz), 7.46 (2H, d, J=8.3 Hz), 7.57 (2H, d, J=8.3 Hz).

REFERENCE EXAMPLE 22
Trans-4-(trifluoromethyl)cinnamaldehyde

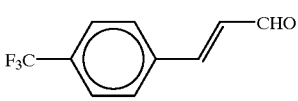

In 30 ml of methylene chloride were dissolved 2.15 g of trans-4-(trifluoromethyl)cinnamyl alcohol, and 14 g of active manganese dioxide were added to the solution at 0° C., followed by stirring of the resulting mixture for 15 minutes and then stirring at room temperature for 2 hours. The solid was removed by filtration and the filtrate was concentrated to obtain a crystalline residue. The residue was recrystallized from a mixed solvent of benzene-hexane to obtain the title compound having a melting point of 60 to 61° C. in a yield of 90%.

NMR spectrum (270 MHz, CDCl$_3$) δ ppm: 6.78 (1H, dd, J=16.2, 7.3 Hz), 7.53 (1H, d, J=16.2 Hz), 7.69 (4H, s), 9.76 (1H, d, J=7.3 Hz).

IR spectrum $\upsilon_{max}$ (KBr) cm$^{-1}$: 1680, 1630, 1321, 1173, 1123, 1066.

Mass spectrum m/e: 200 (M$^+$), 199, 171, 151, 145, 131 (100%), 103, 102.

REFERENCE EXAMPLE 23
Ethyl (2E,4E)-5-[4-jtrifluoromethyl)phenyl]-2,4-pentadienoate

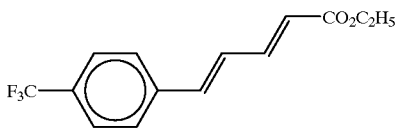

After 4.51 g (103 mmol) of 55% sodium hydride were washed with hexane, it was suspended in 70 ml of 1,2-dimethoxyethane, and 25.9 g (103 mmol) of triethyl phosphonocrotonate were added dropwise thereto while the suspension was stirred at 0° C. under nitrogen atmosphere. After 15 minutes, 10.0 g (57.4 mmol) of 4-(trifluoromethyl) benzaldehyde was added to the resulting mixture at the same temperature and the mixture was stirred for 10 minutes. The reaction mixture was poured in ice-water, followed by extraction with ethyl acetate. The oily residue obtained by evaporation of the solvent was subjected to column chromatography using silica gel and eluted with 6% ethyl acetate-hexane to obtain 11.2 g (yield: 72%) of the title compound as an oil.

NMR spectrum (270 MHz, CDCl$_3$) δ ppm: 1.32 (3H, t, J=7.3 Hz), 4.24 (2H, q, J=7.3 Hz), 6.05 (1E, d, J=15.2 Hz), 6.85–7.0 (21, m), 7.44 (1H, ddd, J=15.2, 7.9, 2.6 Hz), 7.55 (2H, d, J=8.6 Hz), 7.61 (2H, d, J=8.6 Hz).

REFERENCE EXAMPLE 24

(2E,4E)-5-[4-(Trifluoromethyl)phenyl]-2,4-pentadien-1-ol

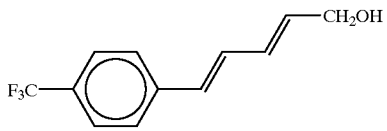

Ethyl (2E,4E)-5-[4-(trifluoromethyl)phenyl]-2,4-pentadienoate was treated with diisobutyl aluminum hydride in the same manner as in Reference example 21 to obtain the title compound in quantitative yield.

NMR spectrum (270 MHz, CDCl$_3$) δ ppm: 1.47 (1H, t, J=5.9 Hz), 4.28 (2H, t, J=5.9 Hz), 6.04 (1H, dt, J=15.2, 5.9 Hz), 6.45 (1H, dd, J=15.2, 10.6 Hz), 6.57 (1H, d, J=15.8 Hz), 6.87 (1H, dd, J=15.8, 10.6 Hz), 7.47 (2H, d, J=8.6 Hz), 7.56 (2H, d, J=8.6 Hz).

REFERENCE EXAMPLE 25

(2E,4E)-5-[4-(Trifluoromethyl)phenyl]-2,4-pentadienal

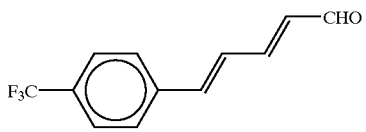

(2E,4E)-5-[4-(Trifluoromethyl)phenyl]-2,4-pentadien-1-ol was treated with active manganese dioxide in the same manner as in Reference example 22 to obtain the title commound in a yield of 92%.

NMR spectrum (270 MHz, CDCl$_3$) δ ppm: 6.33 (1H, dd, J=15.2, 7.3 Hz), 7.0–7.35 (3H, m), 7.60 (2H, d, J=8.6 Hz), 7.64 (2H, d, J=8.6 Hz), 9.65 (1H, d, J=7.3 Hz)

REFERENCE EXAMPLE 26

Ethyl (2E,4E,6E)-7-[4-(trifluoromethyl)phenyl]-2,4,6-heptatrienoate

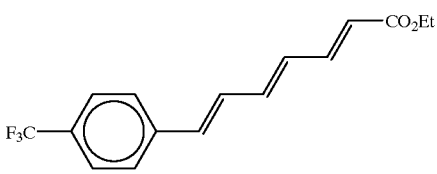

(2E,4E)-5-[4-(Trifluoromethyl)phenyl]-2,4-pentadienal was reacted with triethyl phosphonoacetate in the same manner as in Reference example 20 to obtain the title compound in a yield of 95%.

NMR spectru (270 MHz, CDCl$_3$) δ ppm: 1.31 (3H, t, J=7.3 Hz), 4.23 (2H, q, J=7.3 Hz), 5.96 (1H, d, J=15.2 Hz), 6.49 (1H, dd, J=15.2, 11.2 Hz), 6.72 (1H, dd, J=15.2, 10.6 Hz), 6.73 (1H, d, J=15.8 Hz), 6.94 (1H, dd, J=15.8, 10.6 Hz), 7.37 (1H, dd, J=15.2, 11.2 Hz), 7.51 (2H, d, J=8.6 Hz), 7.58 (2H, d, J=8.6 Hz).

REFERENCE EXAMPLE 27

(2E,4E,6E)-7-[4-(Trifluoromethyl)phenyl]-2,4,6-heptatrien-1-ol

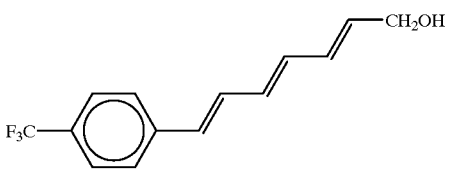

Ethyl (2E,4E,6E)-7-[4-(trifluoromethyl)phenyl]-2,4,6-heptatrienoate was treated with diisobutyl aluminum hydride in the same manner as in Reference example 21 to obtain the title compound in a yield of 90%.

NMR spectrum (270 MHz, CDCl$_3$) δ ppm: 1.41 (1H, t, J=5.3 Hz), 4.25 (2H, t, J=5.3 Hz), 5.95 (1H, dt, J=15.0, 5.3 Hz), 6.3–6.5 (3H, m), 6.57 (1H, d, J=15.2 Hz), 6.90 (1H, m), 7.47 (2H, d, J=8.6 Hz), 7.55 (2H, d, J=8.6 Hz).

REFERENCE EXAMPLE 28

(2E,4E,6E)-7-[4-(Trifluoromethyl)phenyl]-2,4,6-heptatrienal

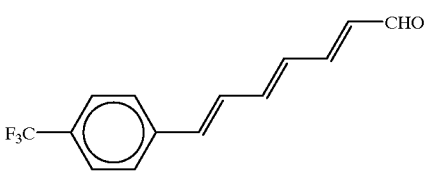

(2E,4E,6E)-7-[4-(Trifluoromethyl)phenyl]-2,4,6-heptatrien-1-ol was treated with active manganese dioxide in the same manner as in Reference example 22 to obtain the title compound in a yield of 88%.

NMR spectrum (270 MHz, CDCl$_3$) δ ppm: 6.23 (1H, dd, J=15.2, 7.9 Hz), 6.62 (1H, dd, J=14.5, 11.2 Hz), 6.82 (1H, d, J=15.8 Hz), 6.84 (1H, dd, J=14.5, 9.9 Hz), 6.98 (1H, dd, J=15.8, 9.9 Hz), 7.19 (1H, dd, J=15.2, 11.2 Hz), 7.54 (2H, d, J=8.6 Hz), 7.61 (2H, d, J=8.6 Hz), 9.62 (1H, d, J=7.9 Hz).

REFERENCE EXAMPLE 29
4-(2,2,3,3-Tetrafluoropropoxy)benzaldehyde

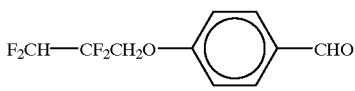

After 1.90 g (43.5 mmol) of 55% sodium hydride were washed with hexane, it was suspended in 25 ml of N,N-dimethylacetamide and 5.3 g (43 mmol) of 4-hydroxybenzaldehyde were gradually added to the suspension at 0° C. under nitrogen atmosphere. When generation of hydrogen gas stopped, 11.14 g (39 mmol) of 2,2,3,3-tetrafluoropropyl p-toluenesulfonate were added to the reaction mixture, followed by heating of the resulting mixture at 120° C. with stirring for 2 hours and 15 minutes. After the reaction mixture was cooled, a mixed solvent of benzene-hexane (1:1) was added thereto and the resulting mixture was washed with water. After drying, the solvent was distilled off to obtain 8.85 g (yield: 96%) of the title compound as an oil.

NMR spectrum (270 MHz, CDCl$_3$) δ ppm: 4.45 (2H, br t, J=11.9 Hz), 6.06 (1H, tt, J=53.3, 4.6 Hz), 7.06 (2H, d, J=8.7 Hz), 7.88 (2H, d, J=8.7 Hz), 9.93 (1H, s).

REFERENCE EXAMPLE 30
Ethyl (2E,4E)-5-[4-(2,2,3,3-tetrafluoropropoxy)phenyl]-2,4-pentadienoate

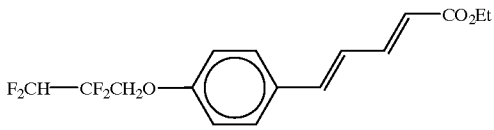

4-(2,2,3,3-Tetrafluoropropoxy)benzaldehyde and triethyl phosphonocrotonate were reacted in the same manner as in Reference example 23 to obtain the title compound having a melting point of 65 to 66° C. in a yield of 74%.

NMR spectrum (270 MHz, CDCl$_3$) δ ppm: 1.31 (3H, t, J=7.3 Hz), 4.23 (2H, q, J=7.3 Hz), 4.37 (2H, br t, J=11.9 Hz), 5.95 (1H, d, J=15.2 Hz), 6.06 (1H, tt, J=53.5, 4.6 Hz), 6.77 (1H, dd, J=15.2, 9.9 Hz), 6.86 (1H, d, J=15.2 Hz), 6.91 (2H, d, J=8.6 Hz), 7.42 (1H, dd, J=15.2, 9.9 Hz), 7.44 (2H, d, J=8.6 Hz)

REFERENCE EXAMPLE 31
(2E,4E)-5-[4-(2,2,3,3-Tetrafluoropropoxy)phenyl]-2,4-pentadien-1-ol

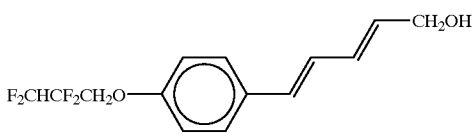

Ethyl (2E,4E)-5-[4-(2,2,3,3-tetrafluoropropoxy)phenyl]-2,4-pentadienoate was treated with diisobutyl aluminum hydride in the same manner as in Reference example 21 to obtain the title compound having a melting point of 95 to 97° C. in a yield of 95%.

NMR spectrum (270 MHz, CDCl$_3$) δ ppm: 1.39 (1H, t, J=-SHz), 4.25 (2H, t, J=5.9 Hz), 4.34 (2H, br t, J=11.9 Hz), 5.94 (1H, dt, J=15.1, 5.9 Hz), 6.06 (1H, tt, J=53.2, 4.8 Hz), 6.40 (1H, dd, J=15.1, 10.3 Hz), 6.50 (1H, d, J=15.5 Hz), 6.69 (1H, dd, J=15.5, 10.3 Hz), 6.88 (2H, d, J=8.7 Hz), 7.36 (2H, d, J=8.7 Hz).

REFERENCE EXAMPLE 32
(2E,4E)-5-[4-(2,2,3,3-Tetrafluoropropoxy)phenyl]-2,4-pentadienal

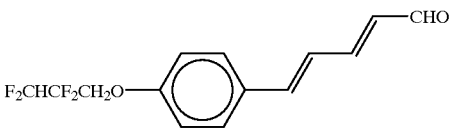

Ethyl (2E,4E)-5-[4-(2,2,3,3-tetrafluoropropoxy)phenyl]-2,4-pentadien-1-ol was treated with active manganese dioxide in the same manner as in Reference example 22 to obtain the title compound having a melting point of 53 to 55° C. in a yield of 96%.

NMR spectrum (270 MHz, CDCl$_3$) δ ppm: 4.38 (2H, br t, J=11.9 Hz), 6.06 (1H, tt, J=52.8, 4.6 Hz), 6.25 (1H, dd, J=15.2, 7.9 Hz), 6.90 (1H, dd, J=15.8, 9.2 Hz), 6.94 (2H, d, J=8.6 Hz), 6.97 (1H, d, J=15.8 Hz), 7.25 (1H, dd, J=15.2, 9.2 Hz), 7.48 (2H, d, J=8.6 Hz), 9.61 (1H, d, J=7.9 Hz).

REFERENCE EXAMPLE 33
Trans-4-(trifluoromethoxy)cinnamaldehyde

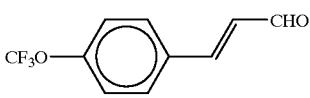

570 mg (3.0 mmol) of 4-(trifluoromethoxy)benzaldehyde and 913 mg (3.0 mmol) of (triphenylphosphoranylidene)acetaldehyde were heated under reflux in 7.5 ml of toluene under nitrogen atmosphere for 1 hour and 45 minutes. The toluene was distilled off under reduced pressure and the thus obtained residue was purified over column chromatography using 20 g of silica gel. The fractions eluted with a mixed solvent of acetic acid-hexane (1:10) were collected to obtain 387 mg (yield: 60%) of the title compound as an oil.

NMR spectrum (270 MHz, CDCl$_3$) δ ppm: 6.70 (1H, dd, J=15.8, 7.3 Hz), 7.29 (2H, d, J=8.6 Hz), 7.47 (1H, d, J=15.8 Hz), 7.61 (2H, d, J=8.6 Hz), 9.72 (1H, d, J=7.3 Hz).

IR spectrum $\upsilon_{max}$ (CHCl$_3$) cm$^{-1}$: 1680, 1508, 1259.

Mass spectrum m/e: 216 (M$^+$), 215, 187, 175, 162, 131(100%), 119, 101.

REFERENCE EXAMPLE 34
Ethyl 6-(2,2,3,3-tetrafluoropropoxy)nicotinate

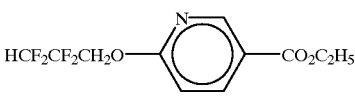

After 840 mg (19.3 mmol) of 55% sodium hydride were washed with hexane, it was suspended in 40 ml of dimethylformamide, and 3.00 g (22.7 mmol) of 2,2,3,3-tetrafluoropropanol were gradually added to the suspension at 0° C. under a nitrogen atmosphere. When generation of hydrogen gas stopped, a solution in which 3.40 g (18.3 mmol) of ethyl 6-chloronicotinate was dissolved in 15 ml of dimethylformamide was added dropwise to the resulting mixture at the same temperature for about 30 minutes. After the dropwise addition, the mixture was stirred for 30 minutes and the reaction mixture was poured into ice-water, followed by extraction with benzene. After the extract was dried, the solvent was distilled off and the thus obtained oil was purified over column chromatography [eluted with a mixed solvent of benzene-hexane (1:1)] using silica gel to obtain 4.42 g (yield: 86%) of the title compound as an oil.

NMR spectrum (270 MHz, CDCl$_3$) δ ppm: 1.40 (3H, t, J=7.2 Hz), 4.39 (2H, q, J=7.2 Hz), 4.81 (2H, br t, J=12.6 Hz), 6.00 (1H, tt, J=53.0, 4.6 Hz), 6.87 (1H, d, J=8.6 Hz), 8.24 (1H, dd, J=8.6, 2.5 Hz), 8.83 (1H, d, J=2.5 Hz).

IR spectrum u$_{max}$ (CHCl$_3$) cm$^{-1}$: 1717, 1604, 1280, 1119.

Mass spectrum m/e: 281 (M$^+$), 236(100%), 180, 152, 151, 123, 122, 93.

REFERENCE EXAMPLE 35
2-(2,2,3,3-Tetrafluoropropoxy)-5-(hydroxymethyl)pyridine

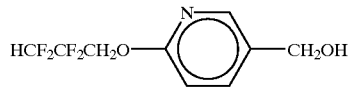

Ethyl 6-(2,2,3,3-tetrafluoropropoxy)nicotinate was reduced with diisobutyl aluminum hydride in the same manner as in Reference example 21 to obtain the title compound as an oil in a yield of 100%.

NMR spectrum (270 MHz, CDCl$_3$) δ ppm: 1.69 (1H, t, J=5.8 Hz), 4.66 (2H, d, J=5.8 Hz), 4.74 (2H, br t, J=12.8 Hz), 6.01 (1H, tt, J=53.1, 4.6 Hz), 6.84 (1H, d, J=8.5 Hz), 7.69 (1H, dd, J=8.5, 2.5 Hz), 8.12 (1H, d, J=2.5 Hz).

Mass spectrum m/e: 239 (M$^+$), 210, 188, 168, 138(100%), 109, 108, 78.

REFERENCE EXAMPLE 36
6-(2,2,3,3-Tetrafluoropropoxy)nicotinaldehyde

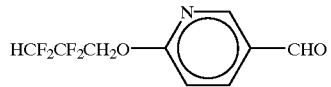

2-(2,2,3,3-Tetrafluoropropoxy)-5-(hydroxymethyl) pyridine was treated with active manganese dioxide in the same manner as in Reference example 22 to obtain the title compound as an oil in a yield of 96%.

NMR spectrum (270 MHz, CDCl$_3$) δ ppm: 4.86 (2H, br t, J=12.8 Hz), 6.01 (1H, tt, J=53.3, 4.4 Hz), 6.97 (1H, d, J=8.6 Hz), 8.15 (1H, dd, J=8.6, 2.3 Hz), 8.65 (1H, d, J=2.3 Hz).

Mass spectrum m/e: 237 (M$^+$), 186, 166, 136(100%), 107, 106, 78.

REFERENCE EXAMPLE 37
(2E,4E)-5-[6-(2,2,3,3-Tetrafluoropropoxy)-3-pyridyl]-2,4-pentadienal

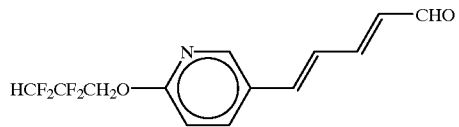

Following Reference examples 23, 24 and 25, the title compound having a melting point of 88 to 89° C. was obtained from 6-(2,2,3,3-tetrafluoropropoxy) nicotinaldehyde in 3 steps.

NMR spectrum (270 MHz, CDCl$_3$) δ ppm: 4.78 (2H, br t, J=12.6 Hz), 6.01 (1H, tt, J=53.3, 4.5 Hz), 6.28 (1H, dd, J=15.2, 7.9 Hz), 6.87 (1H, d, J=8.7 Hz), 6.85–7.0 (2H, m), 7.25 (1H, ddd, J=15.2, 7.8, 2.5 Hz), 7.85 (1H, dd, J=8.7, 2.5 Hz), 8.23 (1H, d, J=2.5 Hz), 9.63 (1H, d, J=7.9 Hz).

IR spectrum υ$_{max}$ (CHCl$_3$) cm$^{-1}$: 1677, 1626, 1591, 1488, 1290, 1120.

Mass spectrum m/e: 289 (M$^+$), 260, 188, 178, 160, 145, 128, 117, 81, 69(100%).

REFERENCE EXAMPLE 38
(2E,4E)-5-(6-Chloro-3-pyridyl)-2,4-pentadienal

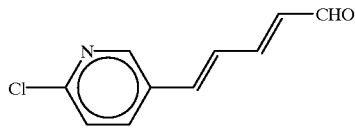

Following Reference examples 23, 24 and 25, the title compound was obtained as an oil from 6-chloronicotinaldehyde in 3 steps.

NMR spectrum (270 MHz, CDCl$_3$) δ ppm: 6.32 (1H, dd, J=15.2, 7.8 Hz), 6.96 (1H, d, J=15.4Fz), 7.05 (1H, dd, J=15.4, 9.8 Hz), 7.26 (1H, dd, J=15.2, 9.8 Hz), 7.36 (1H, d, J=8.3 Hz), 7.80 (1H, dd, J=8.3, 2.5 Hz), 8.48 (1H, d, J=2.5 Hz), 9.66 (1H, d, J=7.8 Hz).

REFERENCE EXAMPLE 39
(4-[(4-Chlorobenzyl)thio]cyclohexylidenelmethyl methyl ether

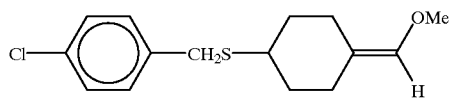

After 146 mg (3.34 mmol) of 55% sodium hydride were washed with hexane, it was suspended in 18 ml of dimethyl sulfoxide, followed by stirring of the resulting suspension at 550C for 2 hours. The mixture was cooled to room temperature and 1.26 g (3.34 mmol) of methoxymethyltriphenylphosphonium chloride were added to the mixture. Further, a solution in which 426 mg (1.67 mmol) of 4-[(4-chlorobenzyl)thio]cyclohexanone were dissolved in 5 ml of dimethyl sulfoxide was added to the resulting mixture. Water was added to the mixture and the resulting mixture was extracted with toluene. After the extract was dried, the crude product obtained by evaporation of the solvent was subjected to column chromatography using 20 g of silica gel and eluted with a mixed solvent of methylene chloride-hexane (1:4) to obtain 370 mg (yield: 78%) of the title compound as an oil.

NMR spectrum (270 MHz, CDCl$_3$) δ ppm: 1.2–1.5 (2H, m), 1.7–2.0 (3H, m), 2.0–2.2 (1H, m), 2.5–2.8 (2H, m), 3.53 (3H, s), 3.71 (2H, s), 5.77 (1H, s), 7.27 (4H, s).

IR spectrum υ$_{max}$ (CHCl$_3$) cm$^{-1}$: 2935, 1689, 1491, 1443, 1123.

Mass spectrum m/e: 282, 157, 124, 109.

REFERENCE EXAMPLE 40
Trans-4-[(4-chlorobenzyl)thio]cyclohexanecarboxaldehyde

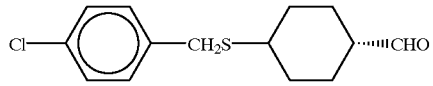

In 20 ml of acetone were dissolved 955 mg (3.4 mmol) of [4-[(4-chlorobenzyl)thio]cyclohexylidene]methyl methyl ether, and 5 ml of water were added to the solution, followed by addition of 1 ml of 5N hydrochloric acid. The mixture was stirred at 55° C. for 20 minutes. The mixture was concentrated under reduced pressure and the residue was extracted with ethyl acetate. After the extract was dried, the crude product obtained by evaporation of the solvent was subjected to column chromatography using 15 g of silica gel and eluted with a mixed solvent of methylene chloride-hexane (1:3) to obtain 865 mg (yield: 95%) of a 1:1 mixture of a trans isomer, the title compound, and a cis isomer as an oil.

This product was stirred in 15 ml of a 0.07N sodium methoxide-methanol solution at room temperature for 2 to 3 hours. To the mixture was added 0.2 ml of acetic acid, and the resulting mixture was diluted with ethyl acetate and washed with an aqueous NaCl solution. After the mixture was dried, the solvent was distilled off to obtain 865 mg of a 4:1 mixture of the title trans form and a cis form as a solid. The solid was recrystallized from a mixed solvent of ether-hexane to obtain 220 mg of the trans form title compound having a melting point of 44 to 46° C.

NMR spectrum (270M[]z, CDCl$_3$) δ ppm: 1.2–1.5 (4H, m), 1.9–2.15 (2H, m), 2.15–2.35 (1H, m), 2.35–2.55 (1H, m), 3.73 (2H, s), 7.27 (5H, s), 9.61 (1H, s).

Cis isomer exhibited a signal at δ 3.67 (2H, s) and δ 9.64 (1H, s).

IR spectrum $v_{max}$(CHCl$_3$) cm$^{-1}$: 2927, 1732, 1493, 1448, 1092.

Mass spectrum m/e: 268, 240, 127, 125, 110.

REFERENCE EXAMPLE 41

4-Cilorobenzyl trans-4-[(1E,3E)-4-[4-(trifluoromethyl)phenyl]-1,3-butadienyl]cyclohexyl sulfide

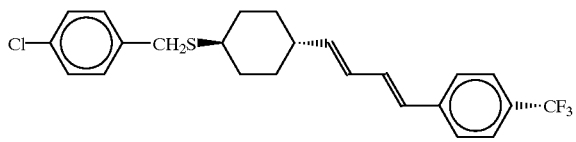

After 50 mg (1.14 mmol) of 55% sodium hydride were washed with hexane, it was suspended in 7 ml of dimethyl sulfoxide, followed by stirring of the suspension at 55° C. for 2.5 hours. The mixture was cooled to room temperature and 607 mg (1.26 mmol) of [(E)-4-(trifluoromethyl)cinnamyl]triphenylphosphonium chloride were added thereto. Further, 170 mg (0.63 mmol) of trans-4-[(4-chlorobenzyl)thio]cyclohexanecarboxaldehyde were added to the resulting mixture, followed by stirring of the mixture at room temperature for 15 minutes. The mixture was diluted with toluene and washed with water and an aqueous NaCl solution. After the mixture was dried, the crude product obtained by evaporation of the solvent was subjected to column chromatography using 5 g of silica gel and eluted with a mixed solvent of methylene chloride-hexane (1:2). The eluted portion was recrystallized from hexane to obtain 86 mg (yield: 31%) of the title compound having a melting point of 142 to 144° C.

NMR spectrum (270 MHz, CDCl$_3$) δ ppm: 1.1–1.3 (2H, m), 1.3–1.5 (2H, m), 1.7–2.0 (2H, m), 2.0–2.2 (2H, m), 2.64 (1H, tt, J=12.4 Hz), 3.74 (2H, s), 5.81 (1H, dd, J=15, 7 Hz), 6.20 (1H, dd, J=15, 10 Hz), 6.47 (1H, d, J=16 Hz), 6.81 (1H, dd, J=16, 10 Hz), 7.29 (4H, s), 7.46 (2H, d, J=8 Hz), 7.55 (2H, d, J=8 Hz).

IR spectrum $v_{max}$ (KBr) cm$^{-1}$: 1641, 1612, 1490, 1326, 1167, 1127, 1069.

Mass spectrum m/e: 436, 417, 403, 311, 277, 235, 159, 125.

REFERENCE EXAMPLE 42

4-Chlorobenzyl trans-4-[(1E,3E)-4-[4-(trifluoromethyl)phenyl]-1,3-butadienyl]cyclohexyl sulfoxide

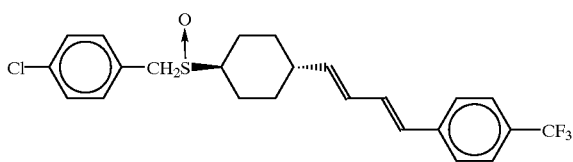

In 20 ml of methylene chloride were dissolved 211 mg (0.48 mmol) of 4-chlorobenzyl trars-4-[(1E,3E)-4-[4-(trifluoromethyl)phenyl]-1,3-butadienyl]cyclohexyl sulfide, and 104 mg (0.48 mmol) of m-chloroperbenzoic acid (purity: 80%) were added to the solution at 0° C., followed by stirring of the resulting mixture for 5 minutes. An aqueous sodium sulfite solution and ethyl acetate were added to the reaction mixture and the organic layer was washed with an aqueous sodium hydrogencarbonate solution and an aqueous NaCl solution. After the mixture was dried, the crude product obtained by evaporation of the solvent was recrystallized from a mixed solvent of ethyl acetate-hexane to obtain 168 mg (yield: 77%) of the title compound having a melting point of 212 to 214° C.

NMR spectrum (270 MHz, CDCl$_3$) δ ppm: 1.1–1.3 (2H, m), 1.5–1.8 (2H, m), 1.9–2.3 (5H, m), 2.42 (1H, tt, J=12, 4 Hz), 3.87 (1H, d, J=13 Hz), 3.97 (1H, d, J=13 Hz), 5.80 (1H, dd, J=15, 7 Hz), 6.22 (1H, dd, J=15, 10 Hz), 6.48 (1H, d, J=16 Hz), 6.80 (1H, dd, J=16, 10 Hz), 7.25 (2H, d, J=8 Hz), 7.36 (2H, d, J=8 Hz), 7.45 (2H, d, J=8 Hz), 7.55 (2H, d, J=8 Hz).

IR spectrum $v_{max}$ (KBr) cm$^{-1}$: 1612, 1492, 1325, 1168, 1128, 1069.

Mass spectrum m/e: 452, 436, 327, 278, 277, 159, 125.

REFERENCE EXAMPLE 43

Trans-1-(acetylthio)-4-[(1E,3E)-4-[4-(trifluoromethyl)phenyl]-1,3-butadien-1-yl]cyclohexane

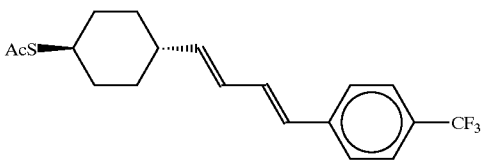

In 11 ml of a mixed solvent of tetrahydrofuran-acetonitrile (8:3) were dissolved 178 mg (0.39 mmol) of 4-chlorobenzyl trans-4-[(1E,3E)-4-[4-(trifluoromethyl)phenyl]-1,3-butadienyl]cyclohexyl sulfoxide, and 168 mg (1.57 mmol) of 2,6-lutidine were added to the solution. To the mixture were added 165 mg (0.79 mmol) of trifluoroacetic anhydride with stirring at 0° C. After 3 minutes, an aqueous sodium hydrogencarbonate solution was added to the mixture, followed by extraction with ethyl acetate. The oily residue obtained by evaporation of the solvent was dissolved in 10 ml of methylene chloride, and 119 mg (1.17 mmol) of triethylamine were added to the mixture at 0° C., followed by addition of 62 mg (0.79 mmol) of acetyl chloride to the resulting mixture. After 1 hour, the reaction mixture was diluted with ethyl acetate and washed with an aqueous sodium hydrogencarbonate solution and an aqueous NaCl solution. After the mixture was dried, the crude product obtained by evaporation of the solvent was subjected to column chromatography using 5 g of silica gel and eluted with a mixed solvent of methylene chloride-hexane (1:1), followed by purification over Rover column [GrosseB, a mixed solvent of ethyl acetate-hexane (1:19)] to obtain 98 mg (yield: 70w) of the title compound having a melting point of 113 to 115° C.

NMR spectrum (270 MHz, CDCl$_3$) δ ppm: 1.2–1.5 (4H, m), 1.7–1.9 (2H, m), 2.0–2.2 (3H, m), 2.31 (3H, s), 3.37 (1H, tt, J=12, 4 Hz), 5.82 (1H, dd, J=15, 7 Hz), 6.20 (1H, dd, J=15, 10 Hz), 6.47 (1H, d, J=16 Hz), 6.81 (1H, dd, J=16, 10 Hz), 7.45 (2H, d, J=8 Hz), 7.54 (2H, d, J=8 Hz).

IR spectrum $\upsilon_{max}$ (KBr) cm$^{-1}$: 1688, 1613, 1326, 1157, 1117, 1068.

Mass spectrum m/e: 354, 335, 311, 277, 235, 159.

REFERENCE EXAMPLE 44
3-[4-(Trifluoromethyl)phenyl]-2-propyn-1-ol

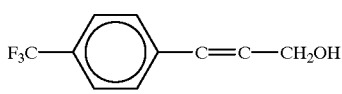

In 50 ml of diethylamine were dissolved 5.0 g (22 mmol) of 4-bromo-α,α,α-trifluorotoluene and 1.25 g (22 mmol) of propargyl alcohol, and 80 mg (0.11 mmol) of bis(triphenylphosphine)palladium (II) chloride and 40 mg (0.22 mmol) of copper (I) iodide were added to the solution, followed by stirring of the resulting mixture at 50° C. for 35 minutes. To the mixture were added 40 mg (0.06 mmol) of bis(triphenylphosphine)palladium (II) chloride, and the resulting mixture was stirred for a further 35 minutes. After the mixture was cooled to room temperature, it was diluted with benzene and filtered, and then the filtrate was washed with water. After the mixture was dried, the crude product obtained by evaporation of the solvent was subjected to column chromatography using 50 g of silica gel and eluted with a mixed solvent of ethyl acetate-hexane (3:17) to obtain 2.21 g (yield: 50%) of the title compound as an oil.

NMR spectrum (270 MHz, CDCl$_3$) δ ppm: 1.8 (1, br, OH), 4.52 (2H, s), 7.54 (2H, d, J=9 Hz), 7.57 (2H, d, J=9 Hz).

IR spectrum $\upsilon_{max}$ (CHCl$_3$) cm$^{-1}$: 3610, 1618, 1324, 1172, 1133, 1069, 1019, 844.

Mass spectrum m/e: 200, 183, 171, 151, 131.

REFERENCE EXAMPLE 45
3-[4-(Trifluoromethyl)pheryl]-2-propynal

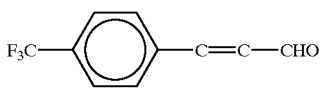

In 20 ml of methylene chloride were dissolved 2.21 g (11.0 mmol) of 3-[4-(trifluoromethyl)phenyl]-2-propyn-1-ol, and 7.43 g (17.5 mmol) of Dess-Martin reagent were added to the solution under ice-cooling for 1.7 hours. Benzene was added to the resulting mixture and the insolubles were removed by filtration, followed by concentration of the filtrate to obtain 1.83 g (yield: 84%) of the title compound as an oil.

NMR spectrum (270 MHz, CDCl$_3$) δ ppm: 7.68 (2H, d, J=9 Hz)$_1$ 7.71 (2H, d, J=9 Hz), 9.45 (1H, s).

IR spectrum $\upsilon_{max}$ (CHCl$_3$) cm$^{-1}$: 2197, 1664, 1324, 1175, 1138.

Mass spectrum m/e: 198, 197, 170, 151, 120.

REFERENCE EXAMPLE 46
Ethyl (E)-5-[(4-trifluoromethyl)phenyl]-2-penten-4-ynoate

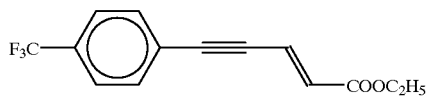

After 181 mg (4.54 mmol) of 55% sodium hydride were washed with hexane, it was suspended in 10 ml of 1,2-dimethoxyethane, and 1.02 g (4.54 mmol) of triethyl 4-phosphonoacetate were added to the suspension with stirring at 0C under nitrogen atmosphere. After 20 minutes, 500 mg (2.52 mmol) of 3-[4-(trifluoromethyl)phenyl]-2-propynal were added to the mixture, followed by stirring of the resulting mixture for 20 minutes. The reaction mixture was diluted with ethyl acetate, ice was added to the mixture and then the organic layer was washed with water. The crude product obtained by distilling off the solvent was subjected to column chromatography using 15 g of silica gel and eluted with benzene to obtain 488 mg (yield: 72%) of the title compound as an oil.

NMR spectrum (270 MHz, CDCl$_3$) δ ppm: 1.32 (3H, t, J=7 Hz), 4.25 (2H, q, J=7 Hz), 6.35 (1H, d, J=16 Hz), 6.97 (1H, d, J=16 Hz), 7.5–7.7 (4H, m).

IR spectrum $\upsilon_{max}$ (CHCl$_3$) cm$^{-1}$: 1712, 1622, 1316, 1174, 1134.

Mass spectrum m/e: 268, 240, 223, 195, 183, 175.

REFERENCE EXAMPLE 47
(E)-5-[4-(Trifluoromethyl)phenyl]-2-penten-4-yn-1-ol

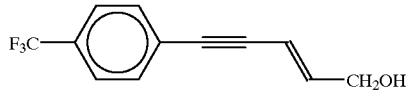

In 4 ml of toluene were dissolved 480 mg (1.79 mmol) of ethyl (E)-5-[4-(trifluoromethyl)phenyl]-2-penten-4-ynoate, and 2.38 ml (3.58 mmol) of a 1.5M diisobutyl aluminum hydride-toluene solution were added to the solution with stirring at 0° C. After 10 minutes, ice was added to the mixture and the insolubles were removed by filtration using Celite. After the organic layer was dried, the crude product obtained by evaporation of the solvent was subjected to column chromatography using 15 g of silica gel and eluted with a mixed solvent of ethyl acetate-hexane (3:17) to obtain 353 mg (yield: 87%) of the title compound as an oil.

NMR spectrum (270 MHz, CDCl$_3$) δ ppm: 1.60 (1H, br, OH), 4.31 (2H, br), 5.99 (1H, d, J=16 Hz), 6.40 (1H, dt, J=16, 5 Hz), 7.54 (2H, d, J=9 Hz), 7.57 (2H, d, J=9 Hz).

REFERENCE EXAMPLE 48
(E)-5-[4-(Trifluoromethyl)phenyl]-2-penten-4-ynal

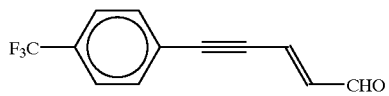

In 4 ml of methylene chloride were dissolved 350 mg (1.56 mmol) of (E)-5-[4-(trifluoromethyl)phenyl]-2-penten-4-yn-1-ol, and 3.5 g of active manganese dioxide were added to the solution, followed by stirring of the resulting mixture at room temperature for 30 minutes. The solid was removed by filtration and the filtrate was concentrated. Then, the filtrate was subjected to column chromatography using 10 g of silica gel and eluted with a mixed solvent of ethyl acetate-hexane (1:24) to obtain 245 mg (yield: 70%) of the title compound as an oil.

NMR spectrum (270 MHz, CDCl₃) δ ppm: 6.58 (1H, dd, J=16, 8 Hz), 6.82 (1H, d, J=16 Hz), 7.63 (4H, s), 9.65 (1H, d, J=8 Hz).

IR spectrum $\upsilon_{max}$ (CHCl₃) cm⁻¹: 1670, 1325, 1132, 1119, 1107, 1072, 845.

Mass spectrum m/e: 224, 196, 195, 175, 170, 146.

REFERENCE EXAMPLE 49

Methyl (Z)-4-chloro-β-(trifluoromethyl)cinnamate

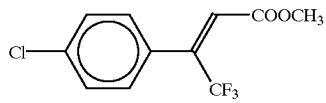

In 10 ml of tetrahydrofuran were dissolved 150 mg (0.47 mmol) of bis(2,2,2-trifluoroethyl) (methoxycarbonylmethyl) phosphonate, and 0.94 ml (0.47 mmol) of a 0.5M potassium hexamethyldisilazide-toluene solution were added dropwise to the mixture with stirring at −78° C. under nitrogen atmosphere. Then, 622 mg (2.36 mmol) of 18-crown-6 were added to the mixture and the resulting mixture was stirred for 20 minutes, followed by addition of a solution in which 98 mg (0.47 mmol) of 4'-chloro-2,2,2-trifluoroacetophenone were dissolved in 1 ml of tetrahydrofuran. The temperature of the reaction mixture was slowly elevated to room temperature and a saturated aqueous ammonium chloride solution was added to the mixture, followed by extraction with ethyl acetate. The crude product obtained by evaporation of the solvent was purified over column chromatography (eluted with 4% ethyl acetate-hexane) using silica gel to obtain 89 mg (yield: 70%, containing about ¹/₁₀ of (E)-isomer) of the title compound as an oil.

NMR spectrum (270 MHz, CDCl₃) δ ppm: 3.85 (3H, s), 6.34 (1H, s), 7.34 (2H, d, J=8.6 Hz), 7.39 (2H, d, J=8.6 Hz).

REFERENCE 50

(Z)-4-Chloro-β-(trifluoromethyl)cinnamaldehyde

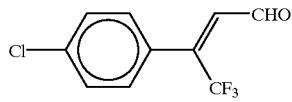

Following Reference examples 21 and 22, the title compound was obtained as an oil in a yield of 81% from methyl (Z)-4-chloro-β-(trifluoromethyl)cinnamate in 2 steps.

NMR spectrum (270 MHz, CDCl₃) δ ppm: 6.36 (1H, d, J=7.3 Hz), 7.38 (2H, d, J=8.6 Hz), 7.44 (2H., d, J=8.6 Hz), 10.21 (1H, dq, J=7.3, 2.0 Hz).

REFERENCE EXAMPLE 51

Methyl (2E,4Z)-5-(4-chlorophenyl)-6,6,6-trifluoro-2,4-hexadienoate

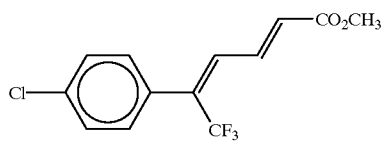

(Z)-4-Chloro-β-(trifluoromethyl)cinnamaldehyde and trimethyl phosphonocrotonate were reacted in the same manner as in Reference example 23 to obtain the title compound as an oil in a yield of about 90% (separation and purification by column chromatography).

NMR spectrum (270 MHz, CDCl₃) δ ppm: 3.81 (3H, s), 6.15 (1H, d, J=15.2 Hz), 6.59 (1H, d, J=11.9 Hz), 7.31 (2H, d, J=8.6 Hz), 7.38 (1H, d, J=8.6 Hz), 7.78 (1H, ddq, J=15.2, 11.9, 2.0 Hz).

REFERENCE EXAMPLE 52

(2E,4Z)-5-(4-Chlorophenyl)-6,6,6-trifluoro-2,4-hexadienal

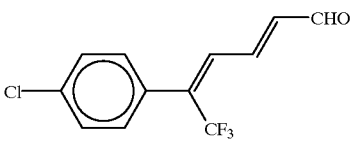

Following Reference examples 21 and 22, the title compound was obtained as an oil in a yield of 71% from methyl (2E,4Z)-5-(4-chlorophenyl)-6,6,6-trifluoro-2,4-hexadienoate in 2 steps.

NMR spectrum (270 MHz, CDCl₃) δ ppm: 6.37 (1H, dd, J=15.2, 7.3 Hz), 6.72 (1H, d, J=11.9 Hz), 7.33 (2H, d, J=8.6 Hz), 7.40 (2H, d, J=8.6 Hz), 7.64 (1H, ddq, J=15.2, 11.9, 2 Hz), 9.74 (1H, d, J=7.3 Hz).

REFERENCE EXAMPLE 53

2-Methyl-2-[(trans-2-phenyl-1,3-dioxan-5-yl)thio]-4'-(trifluoromethyl)propiophenone

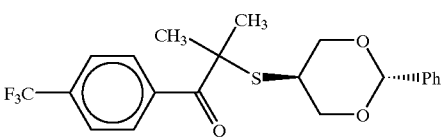

In 3.8 ml of dimethylformamide were dissolved 619 mg (2.10 mmol) of 2-bromo-2-methyl-4'-(trifluoromethyl) propiophenone and 500 mg (2.1 mmol) of trans-4-acetylthio-2-phenyl-1,3-dioxane, and 0.44 ml (2.10 mmol) of a 28% sodium methoxide-methanol solution were added to the solution with stirring at room temperature under nitrogen atmosphere. After 30 minutes, water was added to the reaction mixture and the resulting mixture was extracted with ethyl acetate. The solvent was evaporated to obtain 860 mg (yield: ~100%) of the title compound as a solid.

NMR spectrum (270 MHz, CDCl₃) δ ppm: 1.61 (6H, s), 4.42 (1H, tt, J=11.6, 5.0 Hz), 3.64 (2H, t, J=11.6 Hz), 4.12 (2H, dd, J=11.6, 5.0 Hz), 5.38 (1H, s), 7.3–7.5 (5H, m), 7.68 (2H, d, J=8.2 Hz), 8.19 (2H, d, J=8.2 Hz).

REFERENCE EXAMPLE 54

(RS)-3-Methyl-3-[(trans-2-phenyl-1,3-dioxan-5-yl)thio]-1-(1H-1,2,4-triazol-1-yl)-2-butanol

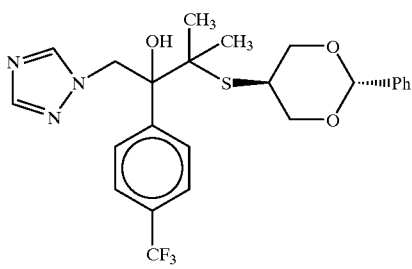

680 mg (1.66 mmol) of 2-methyl-2-[(trans-2-phenyl-1,3-dioxan-5-yl)thio]-4'-(trifluoromethyl)propiophenone, 547 mg (2.49 mmol) of trimethylsulfoxonium iodide, 381 mg (6.79 mmol) of potassium hydroxide and 264 mg (3.82 mmol) of 1,2,4-triazole were heated with stirring in 5.7 ml of t-butanol at 80° C. for 6 hours. After cooling, the reaction mixture was distributed between chloroform and water and the chloroform layer was separated and dried, followed by evaporation of the solvent. The thus obtained oil was subjected to column chromatography using silica gel and eluted with a mixed solvent of ethyl acetate-hexane (1:1) to obtain 605 mg (yield: 74%) of the title compound as a foam.

NMR spectrum (270 MHz, CDCl$_3$) a ppm: 1.38 (3H, s), 1.39 (3H, s), 3.55–3.8 (3H, m), 4.33 (1H, m), 4.54 (1H, m), 5.02 (2H, s), 5.37 (1H, s), 5.44 (1H, s), 7.3–7.6 (5H, m), 7.73 (1H, s), 7.94 (1H, s).

REFERENCE EXAMPLE 55
(RS)-3-(1,3-Dihydroxy-2-propyl) thiol -3-methyl-2-[4-(trifluoromethyl)phenyl]-1-(li-1,2,4-triazol-1-yl)-2-butanol

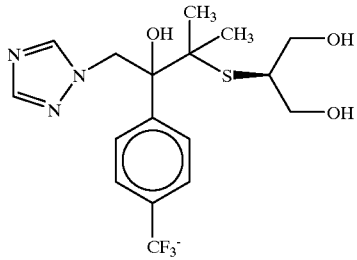

(RS)-3-Methyl-3-[(trans-2-phenyl-1,3-dioxan-5-yl)thio]-1-(1H-1,2,4-triazol-1-yl)-2-butanol was treated with HCl in methanol in the same manner as in Reference example 2 to obtain the title compound as a foam.

NMR spectrum (270 MHz, CDCl$_3$) δ ppm: 1.30 (3H, s), 1.42 (3H, s), 3.35 (1H, m), 3.55–3.8 (3H, m), 3.96 (1H, dd, J=10.9, 5.4 Hz), 4.83 (3H, s), 5.26 (1H, d, J=14.6 Hz), 5.34 (1H, d, J=14.6 Hz), 7.53 (2H, d, J=8.3 Hz), 7.70 (1H, s), 7.75 (2H, d, J=8.3 Hz), 8.26 (1H, s).

REFERENCE EXAMPLE 56
2-(p-Toluenesulfonyloxy)-1,3-propanediol

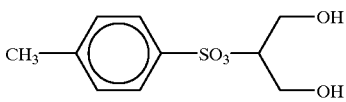

In 50 ml of methanol were dissolved 5.00 g of cis-2-phenyl-4-(p-toluenesulfonyloxy)-1,3-dioxane, and 5 ml of a 4N HCl-dioxane solution were added to the solution, followed by stirring of the resulting mixture at room temperature for 2 hours. To the reaction mixture were added 3.5 g of NaHCO$_3$ powder, and the mixture was stirred for 10 minutes. Then, the reaction mixture was filtered and the filtrate was concentrated under reduced pressure. The thus obtained oil was subjected to column chromatography using silica gel and eluted with ethyl acetate to obtain 3.70 g (yield: 100%) of the title compound as an oil.

NMR spectrum (60 MHz, CDCl$_3$) δ ppm: 2.40 (3H, s), 3.30 (2H, s), 3.73 (4H, d, J=4.5 Hz), 4.55 (1H, quintet, J=4.5 Hz), 7.33 (2H, d, J=8 Hz), 7.84 (2H, d, J=8 Hz).

REFERENCE EXAMPLE 57
Cis-4-(p-toluenesulfonyloxy)-2-[(1E,3E)-4-[4-(trifluoromethyl)phenyl]-1,3-butadien-1-yl]-1,3-dioxane

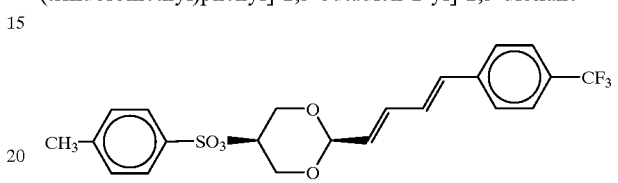

In 4.5 ml of methylene chloride were dissolved 200 mg (0.81 mmol) of 2-(p-toluenesulfonyloxy)-1,3-propanediol and 206 mg (0.91 mmol) of (2E,4E)-5-[4-(trifluoromethyl)phenyl]-2,4-pentadienal, and 15 mg of p-toluenesulfonic acid and 0.8 g of molecular sieves 4A were added to the solution, followed by stirring of the resulting mixture at 0° C. for 1 hour. An aqueous sodium hydrogencarbonate solution was added to the reaction mixture and the mixture was stirred for 10 minutes. Then, the molecular sieves were removed by filtration and the filtrate was extracted with methylene chloride. The oil obtained by evaporation of the solvent was separated by preparative thin layer chromatography of silica gel (developing solvent: 20% ethyl acetate-hexane) to obtain 107 mg (yield: 29%) of a trans isomer having less polarity and 153 mg (yield: 42%) of a cis isomer having higher polarity as an oil, respectively.

NMR spectrum (270 MHz, CDCl$_3$) of cis isomer δ ppm: 2.45 (3H, s), 3.99 (2H, br d, J=13.2 Hz), 4.19 (2H, br d, J=13.2 Hz), 4.45 (1H, br s), 5.09 (1H, d, J=4.6 Hz), 5.82 (1H, dd, J=15.2, 4.6 Hz), 6.57 (1H, dd, J=15.2, 10.5 Hz), 6.63 (1H, d, J=15.2 Hz), 6.82 (1H, dd, J=15.2, 10.5 Hz), 7.36 (2H, d, J=8.6 Hz), 7.48 (2H, d, J=8.6 Hz), 7.56 (2H, d, J=8.6 Hz), 7.85 (2H, d, J=8.6 Hz). TEST EXAMPLE 1

To mice (one group consisting of 10 mice), which were innoculated with 4 to 9×10$^6$ Candida albicans, were administered orally 20 mg/kg of preparations after 1, 4 and 24 hours, and thereafter the survival rate until 21 days after infection was examined. The results of comparison of the compound (I) of the present invention with commercially available Fluconazol are shown in Table 2. From the results, it is apparent that the compound (I) exhibits an excellent antifungal activity.

TABLE 2

| | Survival rate % | |
|---|---|---|
| Compound | 14 days | 21 days |
| Example 2 | 100 | 100 |
| 11 | 100 | 100 |
| 15 | 100 | 100 |
| 16 | 100 | 100 |
| 18 | 100 | 100 |
| 21 | 100 | 60 |
| 30 | 100 | 100 |

TABLE 2-continued

| | Survival rate % | |
|---|---|---|
| Compound | 14 days | 21 days |
| 32 | 100 | 100 |
| 35 | 100 | 100 |
| 37 | 100 | 100 |
| Fluconazol | 70 | 60 |

Preparation example 1

Capsule

| Compound of Examples 1 to 39 or 40 | 50 mg |
|---|---|
| Lactose | 128 mg |
| Corn starch | 70 mg |
| Magnesium stearate | 2 mg |
| | 250 mg |

The thus formulated powder was mixed and passed through a sieve of 60 mesh, and then the powder was encapsulated in No. 3 gelatin capsule of 250 mg to prepare a capsule.

Preparation example 2

Tablet

| Compound of Examples 1 to 39 or 40 | 50 mg |
|---|---|
| Lactose | 126 mg |
| Corn starch | 23 mg |
| Magnesium stearate | 1 mg |
| | 200 mg |

The thus formulated powder was mixed and wet-granulated using a corn starch sizing agent and dried, and then a 200 mg-tablet was made by means of a tablet making machine. If necessary, sugar coating can be applied to the tablet.

The compound having the general formula (I) or a pharmacologically acceptable salt thereof of the present invention has an excellent antifungal activity and is useful as an antifungal agent.

What is claimed is:

1. A triazole compound having the formula:

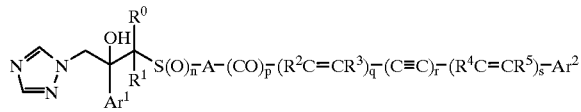

wherein $Ar^1$ represents an ungubstituted phenyl group or a phenyl group having 1 to 3 substituents selected form the group consisting of a halogen atom and a trifluoromethyl group;

$Ar^2$ represents an unsubstituted 5- or 6-membered aromatic heterocyclic group or a substituted 5- or 6-membered aromatic heterocyclic group having 1 to 3 substituents selected from the group consisting of an unsubstituted lower alkyl group, an unsubstituted lower alkoxy group, a halogen atom, a halo substituted lower alkyl group, a halo substituted lower alkoxy group, a nitro group, a cyano group, a —$S(O)_m R^6$ group, wherein $R^6$ represents an unsubstituted lower alkyl group or a halo substituted lower alkyl group and m represents 0, 1 or 2, or a —$NHCOR^7$ group, wherein $R^7$ represents a lower alkyl group, wherein said 5- or 6-membered heterocyclic group is selected from the group consisting of a furyl group, a thienyl group, a pyrrolyl group, a pyrazolyl groups an imidazolyl group, an oxazolyl group, a thiazolyl group, a pvridyl group, a pyrimidyl group and a pyrazyl group;

$R^0$ represents a hydrogen atom or a lower alkyl group;

$R^1$ represents a lower alkyl group;

$R^2$, $R^3$, $R^4$ and $R^5$ are the same or different and each is a hydrogen atom, an unsubstituted lower alkyl group or a halo substituted lower alkyl group and, where q or s or both q and s represent 2, each of $R^2$, $R^3$, $R^4$ and $R^5$ represents independently a group which is the same or different from the other $R^2$, $R^3$, $R^4$ and $R^5$ respectively;

n represents 0, 1 or 2;

p represents 0 or 1;

q, r and s each represent 0, 1 or 2; and

A represents a 1,3-dioxane group, or a pharmacologically acceptable salt thereof.

2. The triazole compound or a pharmacologically acceptable salt thereof according to claim 1, wherein $Ar^1$ is a phenyl group having 1 to 3 substituents selected from the group consisting of a halogen atom and a trifluoromethyl group.

3. The triazole compound or a pharmacologically acceptable salt thereof according to claim 1, wherein $Ar^1$ is a phenyl group having 1 or 2 substituents selected from the group consisting of a fluorine atom, a chlorine atom and a trifluoromethyl group.

4. The triazole compound or a pharmacologically acceptable salt thereof according to claim 1 2, or 3, wherein $Ar^2$ represents said unsubstituted 5- or 6-membered aromatic heterocyclic group.

5. The triazole compound or a pharmacologically acceptable salt thereof according to claim 1 2, or 3, wherein $Ar^2$ represents said substituted 5- or 6-membered aromatic heterocyclic group having 1 to 3 substituents selected from the group consisting of an unsubstituted lower alkyl group, a halogen atom, a halo substituted lower alkyl group, a halo substituted lower alkoxy group, a nitro group, a cyano group or a —$S(O)_m R^6$ group, wherein $R^6$ represents an unsubstituted or halo substituted lower alkyl group and m represents 0, 1 or 2.

6. The triazole compound or a pharmacologically acceptable salt thereof according to claim 1 2, or 3, wherein $Ar^2$ represents, said substituted 5- or 6-membered aromatic heterocyclic group having 1 or 2 substituents selected from the group consisting of an unsubstituted lower alkyl group, a halogen atom, a halo substituted lower alkyl group, a halo substituted lower alkoxy group, a nitro group, a cyano group or a —$S(O)_m R^6$ group, wherein $R^6$ represents an unsubstituted or halo substituted lower alkyl group and m represents 0, 1 or 2.

7. The triazole compound or a pharmacologically acceptable salt thereof according to claim 1, 2 or 3, wherein $Ar^2$ represents a pyridyl group or a thienyl group having 1 or 2 substituents selected from the group consisting of an unsubstituted lower alkyl group, a halogen atom, a halo substituted lower alkyl group, a halo substituted lower alkoxy group, a nitro group, a cyano group or a $S(O)_m R^6$ group, wherein $R^6$ represents an unsubstituted or halo substituted lower alkyl group and m represents 0, 1 or 2.

8. The triazole compound or a pharmacologically acceptable salt thereof according to claim 1, 2 or 3, wherein $R^1$ is a hydrogen atom, a methyl group, an ethyl group or a propyl group.

9. The triazole compound or a pharmacologically acceptable salt thereof according to claim 1, 2 or 3, wherein $R^1$ is a hydrogen atom, a methyl group or an ethyl group.

10. The triazole compound or a pharmacologically acceptable salt thereof according to claim 1, 2 or 3, wherein $R^1$ is a hydrogen atom or a methyl group.

11. The triazole compound or a pharmacologically acceptable salt thereof according to claim 1, 2 or 3, wherein $R^1$ is a methyl group, an ethyl group or a propyl group.

12. The triazole compound or a pharmacologically acceptable salt thereof according to claim 1, 2 or 3, wherein $R^1$ is a methyl group or an ethyl group.

13. The triazole compound or a pharmacologically acceptable salt thereof according to claim 1, 2 or 3, wherein $R^1$ is a methyl group.

14. The triazole compound or a pharmacologically acceptable salt thereof according to claim 1, 2 or 3, wherein $R^2$, $R^3$, $R^4$ and $R^5$ are the same or different and are a hydrogen atom, an unsubstituted lower alkyl group or a fluorine or chlorine substituted lower alkyl group.

15. The triazole compound or a pharmacologically acceptable salt thereof according to claim 1, 2 or 3, wherein $R^2$, $R^3$, $R^4$ and $R^5$ are the same or different and are a hydrogen atom, an unsubstituted methyl group, an unsubstituted ethyl group, an unsubstituted propyl group, a fluorine or chlorine substituted methyl group, a fluorine or chlorine substituted ethyl group or a fluorine or chlorine substituted propyl group.

16. The triazole compound or a pharmacologically acceptable salt thereof according to claim 1, 2 or 3, wherein $R^2$, $R^3$, $R^4$ and $R^5$ are the same or different and are a hydrogen atom, an unsubstituted methyl group, an unsubstituted ethyl group, a fluorine or chlorine substituted methyl group or a fluorine or chlorine substituted ethyl group.

17. The triazole compound or a pharmacologically acceptable salt thereof according to claim 1, 2 or 3, wherein $R^2$, $R^3$, $R^4$ and $R^5$ are the same or different and are a hydrogen atom or an unsubstituted methyl group or a fluorine or chlorine substituted methyl group.

18. The triazole compound or a pharmacologically acceptable salt thereof according to claim 2 or 3, wherein n is 0 or 1.

19. The triazole compound or a pharmacologically acceptable salt thereof according to claim 1, 2 or 3, wherein n is 0.

20. The triazole compound or a pharmacologically acceptable salt thereof according to claim 2 or 3, wherein p is 0.

21. The triazole compound or a pharmacologically acceptable salt thereof according to claim 2 or 3, wherein q, r and s are each 0 or 1.

22. An antifungal composition comprising an antifungal effective amount of the triazole compound or a pharmacologically acceptable salt thereof according to claim 1, 2 or 3 as an active ingredient in combination with a pharmaceutically acceptable carrier or diluent.

23. A method of treating a patient suffering from a *Candida albicans* mycotic disease comprising administering to the patient an effective anti-fungicidal amount of the triazole compound of claim 1 or a pharmacologically acceptable salt thereof.

24. The triazole compound or a pharamcologically acceptable salt thereof according to claim 1, wherein $Ar^1$ is an unsubstituted phenyl group or a phenyl group having 1 to 3 substituents selected from the group consisting of a halogen atom and a trifluoromethyl group;

$Ar^2$ represents an unsubstituted 5- or 6-membered aromatic heterocyclic group or a substituted 5- or 6-membered aromatic heterocyclic group having 1 to 3 substituents independently selected from the group consisting of an unsubstituted lower alkyl group, a halogen atom, a halo substituted lower alkyl group, a halo substituted lower alkoxy group, a nitro group, a cyano group and an $S(O)_m R^6$ group, wherein $R^6$ represents an unsubstituted lower alkyl group or a halo substituted lower alkyl group, wherein said 5- or 6-membered heterocyclic group is selected from the group consisting of a furyl group, a thienyl group, a pyrrolyl group, a pyrazolyl group, an imidazolyl group, an oxazolyl group, a thiazolyl group, a pyridyl group, a pyrimidyl group and a pyrazyl group;

m represents 0, 1 or 2;

$R^0$ is a hydrogen atom, a methyl group, an ethyl group or a propyl group;

$R^1$ is a methyl group, an ethyl group or a propyl group;

$R^2$, $R^3$, $R^4$ and $R^5$ are independently selected from the group consisting of a hydrogen atom, an unsubstituted lower alkyl group, a fluorine substituted lower alkyl group and a chlorine substituted lower alkyl group;

n is 0 or 1;

p is 0;

q, r and s are each 0 or 1; and

A is a 1,3-dioxane group.

25. The triazole compound or a pharmacologically acceptable salt thereof according to claim 24, wherein $R^2$, $R^3$, $R^4$ and $R^5$ are the same or different and are a hydrogen atom, an unsubstituted methyl group, an unsubstituted ethyl group, an unsubstituted propyl group or a fluorine or chlorine substituted methyl group, a fluorine or chlorine substituted ethyl group or a fluorine or chlorine substituted propyl group.

26. The triazole compound or a pharmacologically acceptable salt thereof according to claim 25, wherein $Ar^2$ represents an unsubstituted pyridyl group or a pyridyl group or a thienyl group having 1 or 2 substituents which are independently selected from the group consisting of an unsubstituted lower alkyl group, a halogen atom, a halo substituted lower alkyl group, a halo substituted lower alkoxy group, a nitro group, a cyano group or a —$S(O)_m R^6$ group, wherein $R^6$ represents an unsubstituted lower alkyl group or a halo substituted lower alkyl group and m represents 0, 1 or 2.

27. The triazole compound or a pharmacologically acceptable salt thereof according to claim 26, wherein $R^2$, $R^3$, $R^4$ and $R^5$ are the same or different and are a hydrogen atom, an unsubstituted methyl group or a fluorine or chlorine substituted methyl group; and n is 0.

28. The triazole compound or a pharmacologically acceptable salt thereof according to claim 27, wherein $R^0$ is a hydrogen atom or a methyl group;

$R^1$ is methyl.

29. The triazole compound or a pharmacologically acceptable salt thereof according to claim 1, wherein the triazole compound is (2R,3R)-2-(2,4-difluorophenyl)-3-[[trans-2-[(1E,3E)-4-[6-(2,2,3,3-tetrafluoropropoxy)-3-pyridyl]-1,3- butadien-1-yl]-1,3-dioxan-5-yl]thio]-1-(1H-1,2,4-triazol-5-yl)-2-butanol.

30. The antifungal composition according to claim 22, wherein the triazole compound is
(2R,3R)-2-(2,4-difluorophenyl)-3-[[trans-2-[(1E,3E)-4-[6-(2,2,3,3-tetrafluoropropoxy)-3-pyridyl]-1,3-butadien-1-yl]-1,3-dioxan-5-yl]thio]-1-(1H-1,2,4-triazol-5-yl)-2-butanol or pharmaceutically acceptable salts thereof.

31. The method according to claim 23, wherein the triazole compound is
(2R,3R)-2-(2,4-difluorophenyl)-3-[[trans-2-[(1E,3E)-4-[6-(2,2,3,3-tetrafluoropropoxy)-3-pyridyl]-1,3-butadien-1-yl]-1,3-dioxan-5-yl]thio]-1-(1H-1,2,4-triazol-5-yl)-2-butanol or pharmaceutically acceptable salts thereof.

32. The triazole compound or a pharmacologically acceptable salt thereof according to claim 1, wherein $Ar^2$ is selected from the group consisting of a furyl group, a thienyl group, a pyrrolyl group and a pyridyl group.

33. The triazole compound or a pharmacologically acceptable salt thereof according to claim 1, wherein $Ar^2$ is a thienyl group.

34. The triazole compound or a pharmacologically acceptable salt thereof according to claim 1, wherein $Ar^2$ is a pyridyl group.

35. The triazole compound or a pharmacologically acceptable salt thereof according to claim 25, wherein $Ar^2$ is selected from the group consisting of a furyl group, a thienyl group, a pyrrolyl group and a pyridyl group.

36. The triazole compound or a pharmacologically acceptable salt thereof according to claim 25, wherein $Ar^2$ is a thienyl group.

37. The triazole compound or a pharmacologically acceptable salt thereof according to claim 25, wherein $Ar^2$ is a pyridyl group.

38. The triazole compound or a pharmacologically acceptable salt thereof according to claim 1, wherein the compound is (2R,3R)-2-(2,4-difluorophenyl)-3-[[trans-2-[(E)-2-(3-pyridyl)vinyl]-1,3-dioxan-5-yl]thio]-1-(1H-1,2,4-triazol-1-yl)-2-butanol.

39. The triazole compound or a pharmacologically acceptable salt thereof according to claim 1, wherein the compound is (2R,3R)-3-[[trans-2-[(E)-2-(5-chloro-2-thienyl)vinyl]-1,3-dioxan-5-yl]thio]-2-(2,4-difluorophenyl)-1-(1H-1,2,4-triazol-1-yl)-2-butanol.

40. The triazole compound or a pharmacologically acceptable salt thereof according to claim 1, wherein the compound is (2R,3R)-3-[[trans-2-[(1E,3E)-4-(6-chloro-3-pyridyl)-1,3-butadien-1-yl]-1,3-dioxan-5-yl]thio]-2-(2,4-difluorophenyl)-1-(1H-1,2,4-triazol-1-yl)-2-butanol.

41. The triazole compound or a pharmacologically acceptable salt thereof according to claim 1, wherein $Ar^2$ is selected from the group consisting of chloropyridyl, (trifluoromethyl)pyridyl, (2,2,3,3-tetrafluoropropoxy) pyridyl, (trifluoromethyl)furyl, chlorothienyl and (trifluoromethyl)thienyl.

42. The triazole compound or a pharmacologically acceptable salt thereof according to claim 1, wherein $Ar^2$ is selected from the group consisting of 6-chloro-3-pyridyl, G-(trifluoromethyl)-3-pyridyl, 5-chloro-2-pyridyl, 6-(2,2,3,3-tetrafluoropropoxy)-3-pyridyl, 5-(trifluoromethyl)-2-turyl, 5-chloro-2-thienyl and 5-(trifluromethyl)-2-thienyl.

43. The method according to claim 28, wherein the triazole compound is selected from the group consisting of (2R,3R)-2-(2,4-difluorophenyl)-3-[[trans-2-[(E)-2-(3-pyridyl) vinyl]-1,3-dioxan-5-yl]thio]-1-(1H-1,2,4-triazol-1-yl)-2-butanol;

(2R,3R)-3-[[trans-2-[(E)-2-(5-chloro-2-thienyl)vinyl]-1,3-dioxan-5-yl]thio]-2-(2,4-difluorophenyl) -1-(1H-1,2,4-triazol-1-yl)-2-butanol;

(2R,3R)-3-[[trans-2-[(1E,3E)-4-(6-chloro-3-pyridyl)-1,3-butadien-1-yl]-1,3-dioxan-5-yl]thio]-2-(2,4-difluorophenyl) -1-(1H-1,2,4-triazol-1-yl)-2-butanol and (2R,3R)-2-(2,4-difluorophenyl)-3-[[trans-2-[(1E,3E)-4-[6-(2,2,3,3-tetrafluoropropoxy) -3-pyridyl]-1,3-butadien-1-yl]-1,3-dioxane-5-yl]thio]-1-(1H-1,2,4-triazol-5-yl)-2-butanol.

\* \* \* \* \*